(12) United States Patent
Jeschke et al.

(10) Patent No.: US 8,183,351 B2
(45) Date of Patent: May 22, 2012

(54) AVERMECTIN DERIVATIVES

(75) Inventors: Peter Jeschke, Bergisch Gladbach (DE); Gunter Karig, Hofheim am Taunus (DE); Robert Velten, Langenfeld (DE); Reiner Fischer, Monheim (DE); Olga Malsam, Rösrath (DE); Ulrich Görgens, Ratingen (DE); Christian Arnold, Langenfeld (DE); Erich Sanwald, Kiel (DE); Achim Harder, Köln (DE); Andreas Turberg, Haan (DE)

(73) Assignee: Bayer Cropscience AG, Monheim (DE)

( * ) Notice: Subject to any disclaimer, the term of this patent is extended or adjusted under 35 U.S.C. 154(b) by 419 days.

(21) Appl. No.: 12/377,748

(22) PCT Filed: Aug. 8, 2007

(86) PCT No.: PCT/EP2007/006991
§ 371 (c)(1),
(2), (4) Date: Apr. 28, 2009

(87) PCT Pub. No.: WO2008/019784
PCT Pub. Date: Feb. 21, 2008

(65) Prior Publication Data
US 2010/0234312 A1 Sep. 16, 2010

(30) Foreign Application Priority Data

Aug. 17, 2006 (DE) .......... 10 2006 038 632
Feb. 16, 2007 (DE) .......... 10 2007 007 750

(51) Int. Cl.
*C07H 17/08* (2006.01)
*A01N 43/04* (2006.01)
*A61K 31/70* (2006.01)

(52) U.S. Cl. .......... 536/6.5; 514/31
(58) Field of Classification Search .......... 536/6.5, 536/17, 7.1; 514/31
See application file for complete search history.

(56) References Cited

U.S. PATENT DOCUMENTS

| | | | |
|---|---|---|---|
| 4,024,163 A | 5/1977 | Elliott et al. |
| 4,183,948 A | 1/1980 | Huff |
| 4,199,569 A | 4/1980 | Chabala et al. |
| 4,201,861 A | 5/1980 | Mrozik et al. |
| 4,206,205 A | 6/1980 | Mrozik et al. |
| 4,260,838 A | 4/1981 | Lhonore et al. |
| 4,310,519 A | 1/1982 | Albers-Schonberg et al. |
| 5,023,241 A | 6/1991 | Linn et al. |
| 5,229,415 A | 7/1993 | Linn et al. |
| 5,229,416 A | 7/1993 | Meinke et al. |
| 5,981,500 A | 11/1999 | Bishop et al. |
| 2005/0239838 A1 | 10/2005 | Edgar et al. |

FOREIGN PATENT DOCUMENTS

| | | |
|---|---|---|
| DE | 195 03 827 A1 | 8/1996 |
| EP | 0235085 | 9/1987 |
| JP | 54-61197 A | 5/1979 |
| WO | 93/18779 | 9/1993 |
| WO | 94/15944 | 7/1994 |
| WO | 94/29328 | 12/1994 |
| WO | 95/03317 | 2/1995 |
| WO | 98/12179 | 3/1998 |
| WO | 99/67209 | 12/1999 |
| WO | 02/059078 | 1/2002 |
| WO | 02/12248 | 2/2002 |
| WO | 05/021569 | 3/2005 |

OTHER PUBLICATIONS

Capuano et al., "N-Funktionalisierte Ketenimine, II", Apr. 3, 1985.
Julia et al., Synthese et framentation de bicyclo (3.1.) hexanones-2 substituees. Jul. 28, 1966.
International Search Report for Application PCT/EP2007/006991, dated Jul. 29, 2008 (4 pages).
Ranu et al., "Significant Rate Acceleration of the aza-Michael Reaction in Water", Tetrahedron Letter 48 (2007) pp. 141-143.
Banks et al., "Avermectins and Flea Control: Structure-Activity Relationships and the Seclection of Selamectin for Develpment as an Endectocide for Companion Animals", Bioorganic & Medicinal Chemistry 8 (2000) pp. 2017-2025.
Bliard et al., "Synthese of C-2"β- and C-2"a-Fluoro Avermectin B1a", J. Chem. Soc., Chem. Commun., 1987, pp. 368-370. Bowman, "N-Subsitituted Amino-acids. Part II. The Reductive Alkylation of Amino-acids", 1950, pp. 1346-1349.
Campbell, "Ivermectin, an Antiparasitic Agent", Medicinal Research Reviews, vol. 13, No. 1, 61-79 (1993), John Wiley & Sons, Inc.
Dora, "Mectin and Selamectin" Chem. Pharmacology and Safety, 2002, vol. 30 Iss. 50 pp. 30-50.
Wardrop et al., "Template-Directed C-H Insertion: Synthese of the Dioxabicyclo[3.2.1]octane Core of the Zaragozic Acids", Organic Letters, 2001, vol. 3, No. 15, pp. 2261-2264.

(Continued)

*Primary Examiner* — Eric S. Olson
*Assistant Examiner* — Zhengfu Wang
(74) *Attorney, Agent, or Firm* — Baker Donelson Bearman, Caldwell & Berkowitz, PC

(57) ABSTRACT

Novel avermectin derivatives of the formula (I)

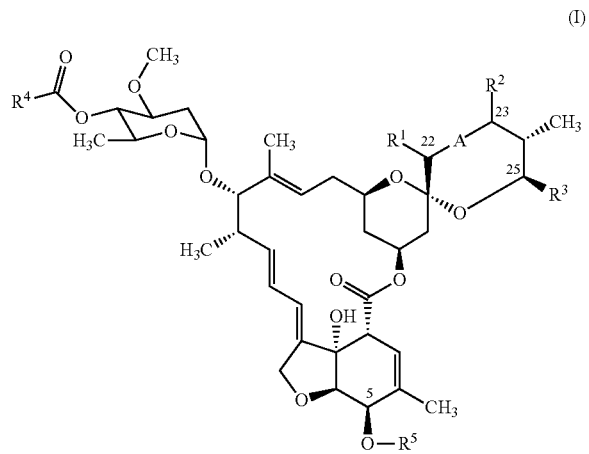

in which $-C_{22}R^1-A-C_{23}R^2$, $R^3$, $R^4$ and $R^5$ have the meanings given in the description, processes for preparing these compounds and their use for controlling animal pests, and also novel intermediates and their preparation.

17 Claims, No Drawings

OTHER PUBLICATIONS

Wardrop et al., "Template-directed C-H activation: development and application to the total syntheses of 7-episordidin", Tetrahedron: Asymmetry 14 (2003) pp. 929-940.

Kato et al., "Microbial Deracemization of a-Substituted Carboxylic Acids: Substrate Specificity and Mechanistic Investigation", J. Org. Chem. 2003, 68, pp. 7234-7242.

Dicale, "Ivermectin, A Broad Spectrum Antiparasitic", IC Drug, 2002, vol. 31, Iss. 13 pp. 607-611.

"Effectiveness of Ivermectin for Control of Arthropod Pests of Livestock", The Southwestern Entromologist, Supplement, 1985, vol. 7, pp. 34-42.

Capito et al., "Chiral oxazonline-1, 3-dithianes: new effective nitrogen-sulfur donating ligands in asymmetric catalysis", Tetrahedron: Asymmetry 16 (2005), pp. 3232-3240.

Elitropi et al., "(E) and (Z)-a-Hydroxy and a-Methoxyimino-4-nitro-1H-imidazole-1-acetic Acids and Esters, Spectral Properties, Conformations and Photoisomerization of the new Compounds", J. Heterocyclic Chem., 16, (1979) p. 1545.

Elliott et al., "Insecticidal Activity of the Pyrethrins and related Compounds VII.a Insecticidal dihalovinyl analogues of cis and trans chrysanthemates", Pestic. Sci. 1956, 6, pp. 537-542.

Goudie et al., "Doramectin—a potent novel endectocide", Veterinary Parasitology, 49 (1993) pp. 5-15.

Mrozik et al., "Avermectin Alycons1", J. Org. Chem., (1982), 47, pp. 489-492.

"Syntheses of Halogenated Pyrid-2-Yloxy A Lkanoic Acids by Means of the Snar React", 1981, vol. 25, Iss. 1, pp. 35-38.

Chabala et al., "Ivermectin, a New Broad-Spectrum Antiparasitic Agent", J. Med. Chem. 1980, 32, pp. 1134-1136.

McDermott et al., "N-Methylamino Acids in peptide Synthesis. II. A New Synthesis of N'Benzyloxycarbonyl, N-Methylamino Acids1", Can. J. Chem., 51, 1973, p. 1915.

"Cellulose-Supported Copper(0) Catalyst for Aza-Michael Addition", Synlett 2006, No. 14, pp. 2246-2250.

Lasota et al., "Abamectin as a pesticide for Agricultural Use", Acta Leidensia, 1990, 59, No. 1 and 2, pp. 217-225.

"Implications for Use in Arthropod Pest", Annual Review of Entomology, 1991, vol. 36, pp. 91-117, Lasota et al.

Putter et al., "Avermectins: novel insecticides acaricides and nematicides from a soil microorganizm", Experientia 37, Feb. 19, 1981, Merck Sharp and Dohme Research Laboratories.

Strong et al., "Avermectins in insect control and biology: a review", Bull. ent. Res. 77, 1987, pp. 357-389.

Strong, "Overview: the impact of avermectins on pastureland ecology", Veterinary parasitology, 48, 1993, pp. 3-17.

Sutherland, "Verterinary Use of Ivermectin", Acta Leidensia, 1990, 59, No. 1 and 2, pp. 211-216.

Parkkari et al., "Synthesis and CB1 receptor activities of novel arachidonyl alcohol derivatives", Bioorganic & Medicinal chemistry letters 14, 2004, pp. 3231-2334.

Wright, "Avermectins: action on target pest species", Department of Pure and Applied Biology, Imperial College Silwood Park, Ascot, Berks. SI5 7PY, U.K. vol. 15, 1987, p. 65.

Preparation of Avermectin B1 Monosaccharide and Avermectin B1 Aglycon, 2004, vol. 43 Iss. 1, pp. 28-29, Wu et al., Chinese J. of Pesticides.

Kontakte, "Monoalkylation of Amines", 1987 Iss. 3, 1987, pp. 8-11.

Tsukamoto et al., "Avermectin Chemistry and Action: Ester-and Ether-type Candidate Photoaffinity Probes", Bioorganic & Medicianl Chemistry 8, 2000, pp. 19-26.

AVERMECTIN DERIVATIVES

CROSS REFERENCE TO RELATED APPLICATIONS

This application is a §371 National Stage Application of PCT/EP2007/006991 filed Aug. 8, 2007 which claims priority to German Application 10 2006 038 632.9 filed August 17, 2006 and to German Application 10 2007 007 750.7 filed Feb. 16, 2007.

BACKGROUND OF THE INVENTION

1. Field of the Invention

The present application relates to novel avermectin derivatives, to processes for their preparation and to their use for controlling animal pests, especially arthropods, in particular insects, in veterinary medicine, hygiene, agriculture, forests and the protection of materials, and also to pesticides comprising avermectin derivatives. Furthermore, the present application relates to the use of novel avermectin derivatives as parasiticides against helminths, nematodes and trematodes in animals, and also to endo- and ectoparaciticides comprising avermectin derivatives.

2. Description of Related Art

Certain avermectin A1a derivatives are already known as insecticides or parasiticides, for example 4'-O-(4-amino-1,4-dioxobutyl)-4'-O-de(2,6-dideoxy-3-O-methyl-α-L-arabino-hexopyranosyl)-5-O-demethyl-22,23-dihydroavermectin A1a (R. A. Dybas, A. S. J. Green, British Crop Protection Conference-Pests and Dis., Proc. (1984), 3, 947-54) as insecticide, 4'-O-acetyl-4'-O-de(2,6-dideoxy-3-O-methyl-α-L-arabinohexopyranosyl)-5-O-demethyl- and 4'-O-(4-chlorobenzoyl)-4'-O-de(2,6-di-deoxy-3-O-methyl-α-L-arabinohexopyranosyl)-5-O-demethylavermectin A1a (U.S. Pat. No. 4,201,861, JP 54-06197) as insecticides and parasiticides and 4'-O-acetyl-4'-O-de(2,6-dideoxy-3-O-methyl-α-L-arabinohexopyranosyl)-5-O-demethyl-25-de(1-methylpropyl)-22,23-dihydro-25-(1-methylethyl)-avermectin A1a (EP 2 350 85 A1) and 4'-O-acetyl-25-cyclohexyl-4'-O-de(2,6-dideoxy-3-O-methyl-α-L-arabinohexopyranosyl)-5-O-demethyl-25-de(1-methylpropyl)-22,23-dihydroavermectin A1a (U.S. Pat. No. 5,981,500 A, WO 94/15944 A1) as parasiticides, in particular endo- and ectoparasiticides.

However, the action of these prior-art compounds is not in all aspects entirely satisfactory. In all areas of application, there is need for effective compounds, in particular at low application rates and concentrations. Accordingly, it is an object of the present invention to provide compounds displaying convincing activity against animal pests and parasites.

SUMMARY OF THE INVENTION

This invention now provides novel avermectin derivatives of the formula (I)

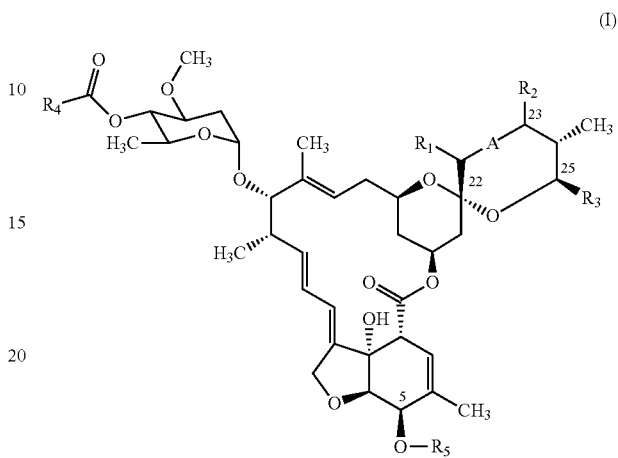

in which the grouping —$C_{22}R^1$-A-$C_{23}R^2$— represents —HC=CH—, —$H_2C$—CH(OH)— or —$H_2C$—$CH_2$—, $R^3$ represents sec-butyl, isopropyl or cyclohexyl, $R^5$ represents hydrogen, methyl or $C_{1-4}$-alkylcarbonyl, and $R^4$ represents optionally substituted $C_{2-6}$-alkyl, $C_{2-6}$-alkenyl, $C_{2-6}$-alkynyl, $C_{1-6}$-alkoxy-$C_{1-4}$-alkyl, $C_{1-4}$-alkoxy-$C_{1-4}$-alkoxy-$C_{1-4}$-alkyl, cycloalkyl, cycloalkenyl, cycloalkyl-$C_{1-4}$-alkyl, aryl, aryl-$C_{1-4}$-alkyl, hetaryl, hetaryl-$C_{1-4}$-alkyl, heterocyclyl or heterocyclyl-$C_{1-4}$-alkyl, or represents a radical selected from the radicals ($G^7$) to ($G^{14}$)

(G⁷)

B—C(R⁶)(R⁷)—

(G⁸)

B—X—C(R⁶)(R⁷)—

(G⁹)

[structure with R¹², R¹³, Y, X, R¹¹]

(G¹⁰)

[structure with R¹⁶, R¹⁷, Me, Me, cyclopropyl]

(G¹¹)

D—C(=N—O—R¹⁸)—

-continued

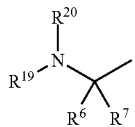
(G¹²)

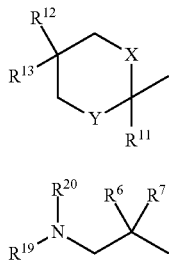
(G¹³)

(G¹⁴)

in which

B represents optionally $R^8$-, $R^9$- and $R^{10}$-substituted aryl, cycloalkyl, heterocyclyl, hetaryl or $NR^{19}R^{20}$, D represents optionally $R^8$-, $R^9$- and $R^{10}$-substituted aryl, cycloalkyl, heterocyclyl, hetaryl or $NR^{19}R^{20}$, $R^4$, however, not representing 4-chlorophenyl (known from U.S. Pat. No. 4,201,861 and JP 54-06197), $R^6$ represents hydrogen, halogen, in particular fluorine, cyano, optionally substituted alkyl alkenyl, alkynyl, cycloalkyl or heterocyclyl, $R^7$ represents hydrogen, halogen, in particular fluorine, cyano, optionally substituted alkyl, alkenyl, alkynyl or $R^6$ and $R^7$ together with the atom to which they are attached represent a 3-, 4-, 5-, 6- or 7-membered ring which is optionally substituted and/or optionally interrupted by oxygen, sulphur, nitrogen, sulphinyl or sulphonyl, or $R^6$ and $R^7$ together with the atom to which they are attached represent an optionally substituted exo-methylene bond, $R^8$ represents hydrogen, optionally substituted $C_{1-4}$-alkyl, $C_{3-6}$-cycloalkyl, $C_{1-4}$-haloalkyl, $C_{1-4}$-alkoxy, $C_{1-4}$-alkoxy-$C_{1-4}$-alkoxy, $C_{1-4}$-haloalkoxy, $C_{1-4}$-alkylthio, $C_{1-4}$-haloalkylthio, $C_{1-4}$-alkylsulphinyl, $C_{1-4}$-haloalkylsulphinyl, $C_{1-4}$-alkylsulphonyl, $C_{1-4}$-haloalkylsulphonyl, hetaryl, such as pyridyl or thienyl, halogen, nitro, cyano, amino, $C_{1-4}$-alkylamino, di-($C_{1-4}$-alkyl)-amino, or represents a radical selected from the group consisting of CO—OH, COO$^{(-)}$, COO—$C_{1-6}$-alkyl, NH—CHO, NH—CO—$C_{1-4}$-alkoxy, N($C_{1-4}$-alkyl)-CO—$C_{1-4}$-alkoxy, P(O)(OH)$_2$, P(O)O$^{(-)}$$_2$, CO—NH$_2$, CS—NH$_2$, C(=NH)—NH$_2$, C(=N—OH)—NH$_2$, CO—NH—$C_{1-4}$-alkyl, CO—N—($C_{1-4}$-alkyl)$_2$, CO—NH—$C_{1-4}$-alkoxy, CO—NH—CO—$C_{1-4}$-alkyl, CO—NH—CO—$C_{1-4}$-haloalkyl, CO—NH—CO—$C_{3-7}$-cycloalkyl, CO—NH—CO—$C_{1-4}$-alkoxy, CO—NH—CO-(aryl-$C_{1-2}$-alkyloxy), SO$_2$—OH, SO$_2$—O$^{(-)}$, SO$_2$—NH$_2$, SO$_2$—NH—$C_{1-4}$-alkyl, SO$_2$—N—($C_{1-4}$-alkyl)$_2$, CO—NH—SO$_2$—NH—$C_{1-4}$-alkyl, CO—NH—SO$_2$—N[di($C_{1-4}$-alkyl), CO—O—$C_{1-6}$-alkyl, $R^9$ represents hydrogen or optionally substituted $C_{1-4}$-alkyl, $C_{1-4}$-haloalkyl, $C_{1-4}$-alkoxy, $C_{1-4}$-haloalkoxy, $C_{1-4}$-alkylthio, $C_{1-4}$-alkylsulphinyl, $C_{1-4}$-alkylsulphonyl, halogen, nitro, cyano, formyl, $C_{1-4}$-alkylcarbonyl, amino, $C_{1-4}$-alkylamino, di-($C_{1-4}$-alkyl)-amino, optionally substituted aryl, optionally substituted hetaryl or optionally substituted heterocyclyl, $R^{10}$ represents hydrogen or optionally substituted $C_{1-4}$-alkyl, $C_{2-4}$-alkenyl, $C_{2-4}$-alkynyl, $C_{1-4}$-haloalkyl, $C_{1-4}$-alkylcarbonyl, $C_{1-4}$-alkoxycarbonyl, $R^{11}$ represents hydrogen, cyano or optionally substituted $C_{1-6}$-alkyl, $R^{12}$ and $R^{13}$ independently of one another represents hydrogen, hydroxyl, or optionally substituted $C_{1-4}$-alkyl, $C_{2-4}$-alkenyl, $C_{2-4}$-alkynyl, $C_{1-6}$-alkylcarbonyl, $C_{1-6}$-alkylamino, di-($C_{1-6}$-alkyl)-amino, $C_{1-6}$-alkylamino-$C_{1-4}$-alkyl, di-($C_{1-6}$alkyl)-amino-$C_{1-4}$-alkyl, $C_{1-6}$-alkoxy-$C_{1-4}$-alkyl, amino-$C_{1-4}$-alkyl, $C_{3-6}$-cycloalkyl, aryl, aryl-$C_{1-4}$-alkyl, hetaryl-$C_{1-4}$-alkyl, heterocyclyl, heterocyclyl-$C_{1-4}$-alkyl or hetaryl, or $R^{12}$ and $R^{13}$ together with the atom to which they are attached represent an optionally substituted 3-, 4-, 5-, 6- or 7-membered ring which may optionally be interrupted by oxygen, sulphur, nitrogen, sulphinyl or sulphonyl, or $R^{12}$ and $R^{13}$ together with the atom to which they are attached represent

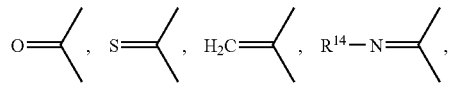

X represents oxygen, sulphur, sulphinyl, sulphonyl or N—$R^{14}$, where $R^{14}$ represents hydrogen or optionally substituted $C_{1-4}$-alkyl, Y represents oxygen, sulphur, sulphinyl, sulphonyl or N—$R^{15}$, where $R^{15}$ represents hydrogen, optionally substituted $C_{1-4}$-alkyl, $R^{16}$ represents methyl, chlorine, bromine or trifluoromethyl, $R^{17}$ represents methyl, chlorine or bromine, $R^{18}$ represents hydrogen or optionally substituted $C_{1-4}$-alkyl, aryl-$C_{1-4}$-alkyl or hetaryl-$C_{1-4}$-alkyl, $R^{19}$ and $R^{20}$ independently of one another represent hydrogen or optionally substituted $C_{1-4}$-alkyl, $C_{1-4}$-haloalkyl, $C_{1-4}$-alkoxycarbonyl, $C_{1-4}$-alkylcarbonyl, $C_{1-6}$-alkoxy-$C_{1-4}$-alkyl, $C_{1-6}$-alkylamino-$C_{1-4}$-alkyl, di-($C_{1-6}$-alkyl)-amino-$C_{1-4}$-alkyl, $C_{1-4}$-alkoxycarbamoyl, $C_{2-6}$-alkenyl, $C_{2-6}$-alkynyl, aryl-$C_{1-4}$-alkyl, hetaryl-$C_{1-4}$-alkyl, or $R^{19}$ and $R^{20}$ together with the nitrogen atom to which they are attached represent a cyclic amino group or represent a 3-, 4-, 5-, 6- or 7-membered ring which is optionally interrupted by oxygen, sulphur, nitrogen, sulphinyl or sulphonyl and/or which is optionally substituted by at least one, in particular 1, 2, 3 or 4, radical as defined in $R^8$, $R^9$ and $R^{10}$.

DETAILED DESCRIPTION OF A PREFERRED EMBODIMENT

The invention furthermore provides the preparation process described below which gives avermectin derivatives of the formula (I) according to the invention by converting compounds of the formula (II)

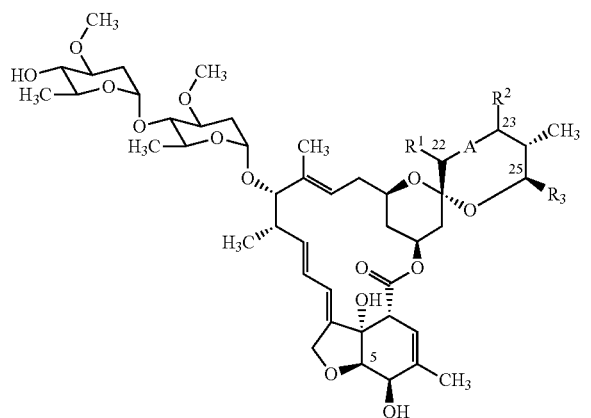

(II)

in which the grouping —$C_{22}R^1$-A-$C_{23}R^2$— and $R^3$ have the meaning mentioned above in a first reaction step in the presence of a diluent and in the presence of an acidic reaction auxiliary into corresponding compounds of the formula (III)

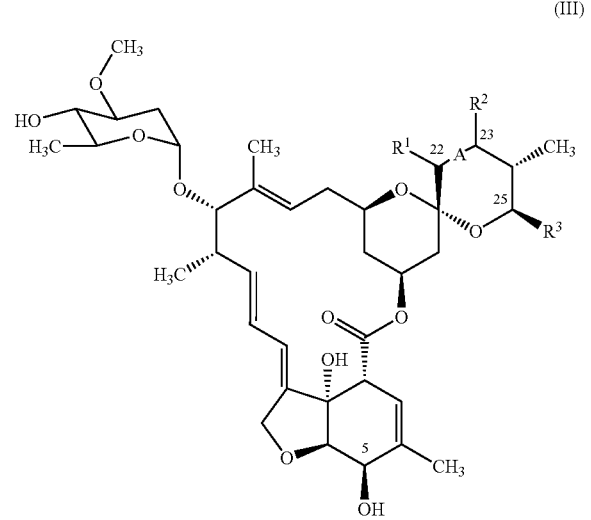

(III)

in which the grouping —$C_{22}R^1$-A-$C_{23}R^2$— and $R^3$ have the meaning mentioned above, and then converting these in a second reaction step, in the presence of a diluent and, if appropriate, in the presence of a basic reaction auxiliary with suitable protective groups into macrocyclic lactones of the formula (IV)

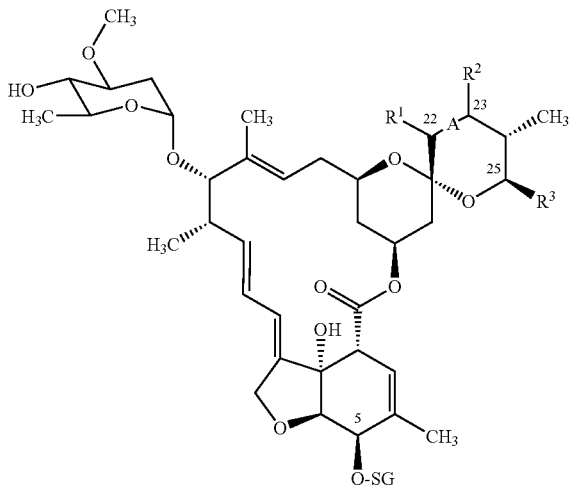

(IV)

in which the grouping —$C_{22}R^1$-A-$C_{23}R^2$— and $R^3$ have the meaning mentioned above, SG represents a suitable protective group radical, and then reacting these in a third reaction step, if appropriate in the presence of a diluent and if appropriate in the presence of a basic reaction auxiliary, with compounds of the formula (V)

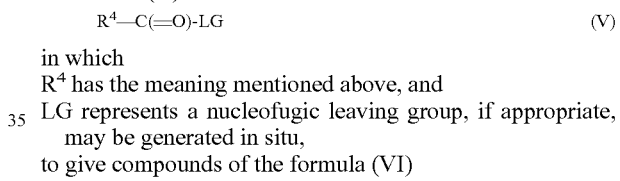

$$R^4\text{—}C(=O)\text{-}LG \qquad (V)$$

in which $R^4$ has the meaning mentioned above, and

LG represents a nucleofugic leaving group, if appropriate, may be generated in situ, to give compounds of the formula (VI)

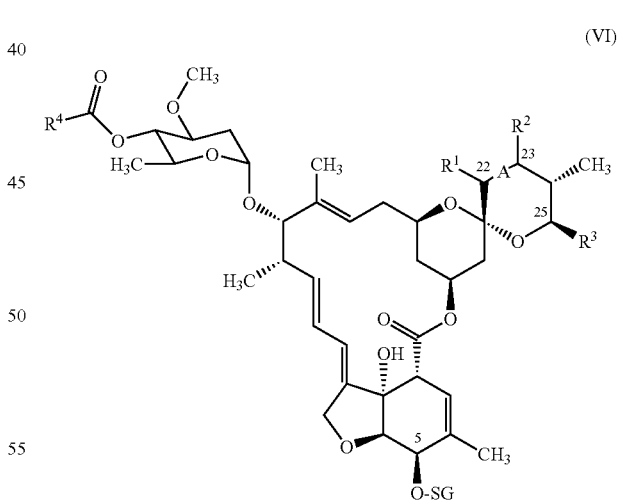

(VI)

in which the grouping —$C_{22}R^1$-A-$C_{23}R^2$— and $R^3$ have the meaning mentioned above, and SG represents a suitable protective group radical, and then reacting these in a fourth reaction step under the reaction conditions of a protective group deblocking, if appropriate in the presence of a diluent and if appropriate in the presence of a suitable acidic or basic reaction auxiliary.

According to the invention, alkyl is to be understood as meaning a straight-chain or branched alkyl having 1 to 6, in particular 1 to 4 and preferably 2 to 6 carbon atoms, such as, for example, methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl and 2-ethylbutyl. From among the alkyl radicals, particular preference is given to methyl, ethyl, n-propyl, isopropyl, n-butyl, isobutyl, sec-butyl and tert-butyl.

According to the invention, alkenyl is to be understood as meaning a straight-chain or branched alkenyl having preferably 2 to 6, in particular 2 to 4 carbon atoms, such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. From among the alkenyl radicals, preference is given to 2-propenyl, 2-butenyl and 1-methyl-2-propenyl.

According to the invention, alkynyl is to be understood as meaning a straight-chain or branched alkynyl having preferably 2 to 6, in particular 3 to 4 carbon atoms, such as, for example, 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl and 1-ethyl-1-methyl-2-propynyl. From among the alkynyl radicals, particular preference is given to ethynyl, 2-propynyl and 2-butynyl.

According to the invention, cycloalkyl is to be understood as meaning mono-, bi- and tricyclic cycloalkyl having preferably 3 to 10 carbon atoms, in particular 3, 5 or 7 carbon atoms, such as, for example, cyclopropyl, cyclobutyl, cyclopentyl, cyclohexyl, cycloheptyl, cyclooctyl, bicyclo[2.2.1]heptyl, bicyclo[2.2.2]octyl and adamantyl. From among the cycloalkyl radicals, particular mention may be made of cyclopropyl and cyclobutyl.

According to the invention, halocycloalkyl is to be understood as meaning mono-, bi- and tricyclic halocycloalkyl having preferably 3 to 10 carbon atoms, in particular 3, 5 or 7 carbon atoms, such as, for example, 1-fluorocyclopropyl, 2-fluorocyclopropyl or 1-fluorocyclobutyl.

According to the invention, a haloalkyl radical contains 1 to 4 carbon atoms, in particular 1 to 2 carbon atoms, and preferably 1 to 9, in particular 1 to 5, identical or different halogen atoms. Preference is given to fluorine, chlorine or bromine, in particular fluorine or chlorine. Trifluoromethyl, trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl and pentafluoro-tert-butyl may be mentioned by way of example. From among the haloalkyl radicals, preference is given to difluoromethyl, trifluoromethyl and 2,2-difluoroethyl.

According to the invention, alkoxy is to be understood as meaning a straight-chain or branched alkoxy having preferably 1 to 6 carbon atoms, in particular 1 to 4 carbon atoms, such as, for example, methoxy, ethoxy, n-propoxy, isopropoxy, n-butoxy, isobutoxy, sec-butoxy and tert-butoxy.

According to the invention, haloalkoxy is to be understood as meaning a straight-chain or branched haloalkoxy having preferably 1 to 6 carbon atoms, in particular 1 to 4 carbon atoms, such as, for example, difluoromethoxy, trifluoromethoxy, 2,2-difluoroethoxy, 1,1,2,2-tetrafluoroethoxy, 2,2,2-trifluoroethoxy and 2-chloro-1,1,2-trifluoroethoxy.

According to the invention, alkoxyalkoxy is to be understood as meaning a straight-chain or branched alkoxyalkoxy having preferably 2 to 6 carbon atoms, in particular 2 to 4 carbon atoms, such as, for example, methoxymethoxy, methoxyethoxy, methoxy-n-propoxy and ethoxyisopropoxy.

According to the invention, haloalkoxy is to be understood as meaning a straight-chain or branched haloalkoxy having preferably 1 to 6 carbon atoms, in particular 1 to 4 carbon atoms, such as, for example, difluoromethoxy, trifluoromethoxy, trichloromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy and 2-chloro-1,1,2-trifluoroethoxy.

According to the invention, alkoxyalkoxyalkoxy is to be understood as meaning a straight-chain or branched alkoxyalkoxyalkoxy having preferably 3 to 6 carbon atoms, in particular 3 to 4 carbon atoms, such as, for example, methoxymethoxyethoxy, methoxyethoxyethoxy and methoxyethoxy-n-propoxy.

According to the invention, alkylthio is to be understood as meaning a straight-chain or branched alkylthio having preferably 1 to 6 carbon atoms, in particular 1 to 4 carbon atoms, such as, for example, methylthio, ethylthio, n-propylthio, isopropylthio, n-butylthio, isobutylthio, sec-butylthio and tert-butylthio.

According to the invention, alkylsulphinyl is to be understood as meaning a straight-chain or branched alkylsulphinyl having preferably 1 to 6 carbon atoms, in particular 1 to 4 carbon atoms, such as, for example, methylsulphinyl, ethylsulphinyl, n-propylsulphinyl, isopropylsulphinyl, n-butylsulphinyl, isobutylsulphinyl, sec-butylsulphinyl and tert-butylsulphinyl.

According to the invention, alkylsulphonyl is to be understood as meaning a straight-chain or branched alkylsulphonyl having preferably 1 to 6 carbon atoms, in particular 1 to 4 carbon atoms, such as, for example, methylsulphonyl, ethylsulphonyl, n-propylsulphonyl, isopropylsulphonyl, n-butylsulphonyl, isobutylsulphonyl, sec-butylsulphonyl and tert-butylsulphonyl.

According to the invention, haloalkylthio is to be understood as meaning a straight-chain or branched haloalkylthio radical having preferably 1 to 6 carbon atoms, in particular 1 to 4 carbon atoms, such as, for example, difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoro-ethylthio and 2-chloro-1,1,2-trifluoroethylthio.

According to the invention, haloalkylsulphinyl is to be understood as meaning a straight-chain or branched haloalkylsulphinyl having preferably 1 to 6 carbon atoms, in particular 1 to 4 carbon atoms, such as, for example, difluoromethylsulphinyl, trifluoromethylsulphinyl, trichloromethylsulphinyl, chlorodifluoromethylsulphinyl, 1-fluoroethylsulphinyl, 2-fluoroethylsulphinyl, 2,2-difluoroethylsulphinyl, 1,1,2,2-tetrafluoroethylsulphinyl, 2,2,2-trifluoroethylsulphinyl and 2-chloro-1,1,2-trifluoroethylsulphinyl.

According to the invention, haloalkylsulphonyl is to be understood as meaning a straight-chain or branched haloalkylsulphonyl having preferably 1 to 6 carbon atoms, in particular 1 to 4 carbon atoms, such as, for example, difluoromethylsulphonyl, trifluoromethylsulphonyl, trichloromethylsulphonyl, chlorodifluoromethylsulphonyl, 1-fluoroethylsulphonyl, 2-fluoroethylsulphonyl, 2,2-difluoroethylsulphonyl, 1,1,2,2-tetrafluoroethylsulphonyl, 2,2,2-trifluoroethylsulphonyl and 2-chloro-1,1,2-trifluoroethylsulphonyl.

According to the invention, alkylcarbonyl is to be understood as meaning a straight-chain or branched alkyl carbon having preferably 1 to 6 carbon atoms, in particular 1 to 4 carbon atoms, such as, for example, methylcarbonyl, ethylcarbonyl, n-propylcarbonyl, isopropylcarbonyl, sec-butylcarbonyl and tert-butylcarbonyl.

According to the invention, optionally substituted cycloalkylcarbonyl is to be understood as meaning a mono-, bi- or tricyclic cycloalkylcarbonyl having preferably 3 to 10 carbon atoms, in particular 3, 5 or 7 carbon atoms, in the cycloalkyl moiety. Cyclopropylcarbonyl, cyclobutylcarbonyl, cyclopentyl-carbonyl, cyclohexylcarbonyl, cycloheptyl-carbonyl, cyclooctylcarbonyl, bicyclo[2.2.1]heptyl carbonyl, bicyclo[2.2.2]octylcarbonyl and adamantylcarbonyl may be mentioned by way of example.

According to the invention, alkoxycarbonyl is to be understood as meaning a straight-chain or branched alkoxycarbonyl having preferably 1 to 6 carbon atoms, in particular 1 to 4 carbon atoms, in the alkoxy moiety. Methoxycarbonyl, ethoxycarbonyl, n-propoxycarbonyl, isopropoxycarbonyl, sec-butoxycarbonyl and tert-butoxycarbonyl may be mentioned by way of example.

According to the invention, aryl represents, for example, a mono-, di- or polycyclic aromatic radical, such as phenyl, naphthyl, tetrahydronaphthyl, indanyl and fluorenyl. From among the aryl radicals, preference is given to phenyl and naphthyl, in particular phenyl.

According to the invention, optionally substituted arylalkyl refers to an arylalkyl radical which is optionally substituted at the aryl and/or alkyl moiety, the aryl moiety preferably having 6 or 10 carbon atoms, such as phenyl or naphthyl, in particular 6 carbon atoms, such as phenyl, and the alkyl moiety preferably having 1 to 4, in particular 1 or 2, carbon atoms and being straight-chain or branched. From among the arylalkyl radicals, preference is given to benzyl and 1-phenylethyl.

According to the invention, hetaryl is to be understood as meaning 5- to 7-membered rings having preferably 1 to 3, in particular 1 or 2, identical or different heteroatoms, that is oxygen, sulphur or nitrogen or other suitable atoms. Preferred hetaryl radicals are furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl.

According to the invention, hetarylalkyl is to be understood as meaning 5- to 7-membered rings having preferably 1 to 3, in particular 1 or 2, identical or different heteroatoms. Preferred hetarylalkyl radicals are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinyl-methyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

According to the invention, heterocyclyl is to be understood as meaning saturated or partially unsaturated 3- to 7-membered monocyclic rings having preferably 1 to 3, in particular 1 or 2, identical or different heteroatoms, that is oxygen, sulphur or nitrogen or other suitable atoms, or saturated or partially unsaturated bicyclic ring systems comprising 8 to 14 atoms and containing, either in one ring or in both rings independently of one another, 1 to 5 identical or different heteroatoms selected from the group consisting of oxygen, sulphur and nitrogen. Preferred heterocyclyl radicals are piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, pyrrolidinonyl, pyrrolidindionyl, morpholinonyl, piperazinonyl and oxepanyl.

The groups according to the invention mentioned above and the radicals in the general formulae are optionally substituted, in which case they have at least one, preferably 1 to 3, particularly preferably 1 to 2, identical or different substituents. It is possible for two identical or different substituents to be present at the same atom.

By way of example and at the same time by way of preference, the following substituents may be mentioned:

alkyl having preferably 1 to 4 carbon atoms, such as methyl, ethyl, n-propyl, isopropyl, n-butyl, isobutyl, sec-butyl and tert-butyl, particularly preferably having 1 to 2 carbon atoms;

alkoxy having preferably 1 to 4 carbon atoms, such as methoxy, ethoxy, n-propoxy, isopropoxy, n-butoxy, isobutoxy, sec-butoxy and tert-butoxy, particularly preferably having 1 to 2 carbon atoms;

alkylthio having preferably 1 to 4 carbon atoms, such as methylthio, ethylthio, n-propylthio, isopropylthio, n-butylthio, isobutylthio, sec-butylthio and tert-butylthio, particularly preferably having 1 to 2 carbon atoms; haloalkyl having preferably 1 to 5 halogen atoms, in particular 1 to 3 halogen atoms, where the halogen atoms are identical or different and are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino;

monoalkyl- and dialkylamino, having preferably 1 to 4 carbon atoms per alkyl group, such as methylamino, methylethylamino, dimethylamino, n-propylamino, isopropylamino, methyl-n-butyl-amino, particularly preferably having 1 or 2 carbon atoms; alkylcarbonyl radicals, such as methylcarbonyl; alkoxycarbonyl having preferably 2 to 4 carbon atoms, in particular 2 to 3 carbon atoms, such as methoxycarbonyl and ethoxycarbonyl; alkylsulphinyl having 1 to 4, in particular 1 to 2, carbon atoms; haloalkylsulphinyl having 1 to 4, in particular 1 to 2, carbon atoms and 1 to 5 haloatoms, such as trifluoromethylsulphinyl; haloalkylsulphonyl having 1 to 4, in particular 1 to 2, carbon atoms and 1 to 5 halogen atoms, such as trifluoromethylsulphonyl, perfluoro-n-butylsulphonyl, perfluoroisobutylsulphonyl; arylsulphonyl having preferably 6 or 10 arylcarbon atoms, such as phenylsulphonyl; acyl, aryl, aryloxy, which for their part may carry one of the substituents mentioned above, and also the formimino radical (—HC=N—O-alkyl).

According to the invention, mono- or dialkylamino groups have a straight-chain or branched alkyl having preferably 1 to 6, in particular 1 to 4, carbon atoms and are optionally substituted. Examples of substituted mono- or dialkylamino groups which may be mentioned are methylamino, ethylamino, dimethylamino, diethylamino, di-n-propylamino, diisopropylamino and dibutylamino According to the invention, the alkoxyalkyl group in the mono- or dialkoxyalkylamino groups according to the invention has a straight-chain or branched alkyl having preferably 2 to 6, in particular 2 to 4, carbon atoms. Mono- or dialkoxyalkylamino groups are, for example, methoxymethylamino, methoxyethylamino, di(methoxymethyl)amino or di(methoxyethyl)amino.

Cyclic amino groups which are suitable according to the invention are saturated and/or unsaturated aromatic or aliphatic ring systems having at least one nitrogen atom as heteroatom, which may be a ring system or a plurality of condensed ring systems, and which optionally contain further heteroatoms, such as, for example, one or two nitrogen, oxygen and/or sulphur atoms. The cyclic amino groups according to the invention may also have or be at least one spiro ring or bridged ring system. The number of atoms forming cyclic amino groups is not limited; in the case of a one-ring system, for example, they consist of 3 to 8 atoms, and in the case of a two-ring system of 7 to 11 atoms.

Cyclic amino groups according to the invention having saturated and unsaturated monocyclic groups having a nitrogen atom as heteroatom are, for example, 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; cyclic amino groups according to the invention having saturated and unsaturated monocyclic groups having at least two nitrogen atoms as heteroatoms are, for example, 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; cyclic amino groups according to the invention having saturated and unsaturated monocyclic groups having one or two oxygen atoms and one to three nitrogen atoms as heteroatoms are, for example, oxazolidin-3-yl, 2,3-dihydroisoxazol-2-yl, isoxazol-2-yl, 1,2,3-oxadiazin-2-yl, morpholino; cyclic amino groups according to the invention having saturated and unsaturated monocyclic groups having one to three nitrogen atoms and one to two sulphur atoms as heteroatoms are, for example, thiazolidin-3-yl, isothiazolin-2-yl, thiomorpholino, or dioxothiomorpholino; cyclic amino groups according to the invention having saturated and unsaturated condensed cyclic groups are, for example, indol-1-yl, 1,2-dihydrobenzimidazol-1-yl, perhydropyrrolo[1,2-a]pyrazin-2-yl; a cyclic amino group according to the invention having spirocyclic groups is, for example, 2-azaspiro[4,5]decan-2-yl; a cyclic amino group according to the invention having bridged heterocyclic groups is, for example, 2-azabicyclo[2,2,1]heptan-7-yl.

Furthermore, it has been found that the compounds of the formula (I) according to the invention have pronounced biological properties and are suitable especially for controlling animal pests, in particular insects, arachnids and nematodes, encountered in agriculture, in forests, in the protection of stored products and materials and in the hygiene sector. In addition, the compounds of the formula (I) according to the invention are also suitable for controlling endo- and ectoparasites in veterinary medicine.

If appropriate, depending on the nature of the substituents, the compounds of the formula (I) may be present as geometrically and/or optically active isomers or corresponding isomer mixtures of varying compositions. Accordingly, the invention relates both to the pure isomers and to the isomer mixtures.

The formula (I) provides a general definition of the compounds according to the invention.

Preferred groups, groupings, substituents and ranges of the radicals listed in the formulae mentioned above and below are illustrated below.

The grouping —$C_{22}R^1$-A-$C_{23}R^2$— preferably represents —HC=CH— or —$H_2$C—$CH_2$—, $R^3$ preferably represents sec-butyl or isopropyl, $R^5$ preferably represents hydrogen and $R^4$ preferably represents optionally substituted $C_{2-6}$-alkyl, $C_{1-6}$-haloalkyl, in particular 2,2,2-trifluoroethyl or 1-fluoroethyl; $c_{3-6}$-cycloalkyl, in particular cyclopropyl, 1-cyanocyclopropyl, 1-methyl-cyclopropyl, cyclobutyl or cyclopentyl; $C_{3-6}$-cycloalkenyl, in particular cyclopentenyl; $C_{3-6}$-halocycloalkyl, in particular 2,2-dichlorocyclopropyl or 1-fluorocyclopropyl; cycloalkyl-$C_{1-4}$-alkyl; amino-$C_{1-4}$-alkyl, in particular aminomethyl, aminoethyl, aminopropyl or aminobutyl; $C_{1-6}$-alkylamino-$C_{1-4}$-alkyl, in particular N-methylaminomethyl, N-methylaminoethyl, N-methylaminopropyl, N-methylaminobutyl; di-($C_{1-6}$-alkyl)-amino-$C_{1-4}$-alkyl, in particular N,N-dimethylaminomethyl, N,N-dimethylaminoethyl, N,N-dimethylaminopropyl, N,N-dimethylaminobutyl, N-ethyl-N-propylaminomethyl, N-ethyl-N-propylaminoethyl; $C_{1-6}$-alkoxy-$C_{1-4}$-alkyl, in particular methoxyethyl, ethoxymethyl, methoxyethyl, ethoxyethyl, methoxypropyl, ethoxypropyl, methoxybutyl, ethoxybutyl; aryl, in particular phenyl, except for 4-chlorophenyl (known from U.S. Pat. No. 4,201,861, JP 54-06197); aryl-$C_{1-4}$-alkyl, in particular benzyl or phenethyl; heterocyclyl, in particular 2-oxopyrrolidinyl or pyrrolidinyl; heterocyclylmethyl, in particular N-(2,5-dioxopyrrolidinyl)methyl, 2-oxopiperazinyl-methyl, piperidinylmethyl, N-(3-oxomorpholinyl) methyl; hetaryl, in particular pyridyl, pyrimidyl, pyrazinyl, pyrazolyl, thiazolyl, thienyl, furyl; hetaryl-$C_{1-4}$-alkyl, in particular pyridylmethyl, pyridylethyl, pyrazinylmethyl, pyrimidylmethyl, thiazolylmethyl, triazolylmethyl, pyrazolylmethyl, pyrrolylmethyl, furylmethyl, thienylmethyl, triazolinonemethyl, oxadiazolylmethyl, imidazolylmethyl, isoxazolylmethyl; where substitutents are selected from the group consisting of fluorine, chlorine, bromine or iodine, $C_{1-4}$-alkyl, in particular methyl, ethyl, isopropyl, $C_{3-6}$-cycloalkyl, in particular cyclopropyl, cyclobutyl, cyclopentyl or cyclohexyl, $C_{3-6}$-cycloalkoxy, in particular cyclopropoxy, cyclobutoxy, cyclopentoxy or cyclohexoxy, $C_{3-6}$-cycloalkyl-$C_{1-2}$-alkoxy, in particular cyclopropylmethoxy or cyclopropylethoxy $C_{1-4}$-haloalkyl, in particular trifluoromethyl, amino, hydroxyl, nitro, cyano, $SO_2OH$, COOH, formyl, $C_{1-4}$-alkoxy, in particular methoxy, ethoxy, isopropoxy, $C_{1-2}$-alkylenedioxy, in particular methylenedioxy or ethylenedioxy, alkyleneoxy, in particular $H_2C$=C($CH_3$)—O—, haloalkdioxy, $C_{1-4}$-haloalkoxy, in particular trifluoromethoxy, difluoromethoxy, tetrafluoroethoxy, $C_{1-4}$-alkylthio, in particular methylthio, $C_{1-4}$-alkylsulphinyl, in particular methylsulphinyl, $C_{1-4}$-alkylsulphonyl, in particular methylsulphonyl, $C_{1-4}$-haloalkylthio, in particular trifluoromethylthio, $C_{1-4}$- haloalkylsulphoxyl, in particular trifluoromethylsulphoxyl, $C_{1-4}$-haloalkylsulphonyl, in particular trifluoromethylsulphonyl, $C_{1-4}$-alkylamino, in particular methylamino, di-($C_{1-4}$-alkyl)-amino, in particular N,N-dimethylamino, N,N-diethylamino, $C_{1-4}$-alkylcarbonyl, in particular methylcarbonyl, ethylcarbonyl, $C_{3-6}$-cycloalkylcarbonyl, in particular cyclopropylcarbonyl, phenylcarbonyl, $C_{1-4}$-alkoxycarbonyl, in particular methoxycarbonyl, ethoxycarbonyl, $C_{1-4}$-alkoxy-$C_{1-4}$-alkyl, in particular methoxymethyl, ethoxy methyl, $C_{1-4}$-alkoxy-$C_{1-4}$-alkoxy-$C_{1-4}$-alkyl, in particular methoxyethoxymethyl, ethoxyethoxymethyl, or represents a radical $R^4$ selected from among the radicals ($G^7$-1) to ($G^7$-45)

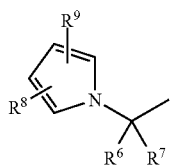

(G⁷-1)

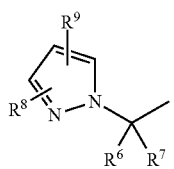

(G⁷-2)

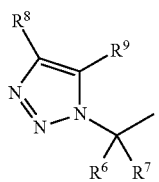

(G⁷-3)

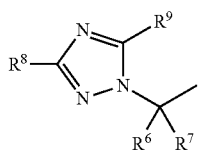

(G⁷-4)

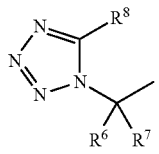

(G⁷-5)

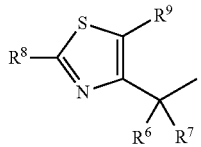

(G⁷-6)

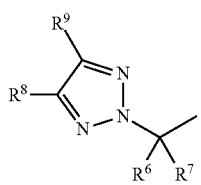

(G⁷-7)

-continued

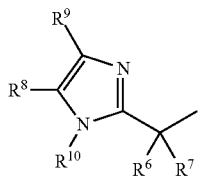

(G⁷-8)

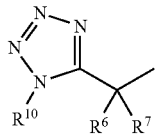

(G⁷-9)

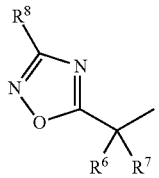

(G⁷-10)

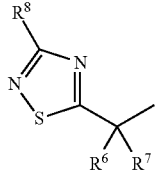

(G⁷-11)

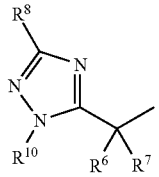

(G⁷-12)

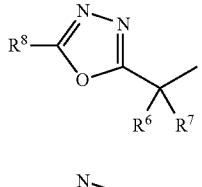

(G⁷-13)

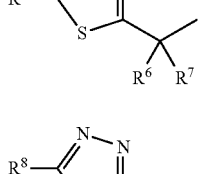

(G⁷-14)

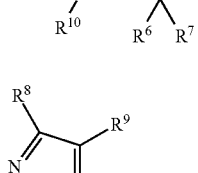

(G⁷-15)

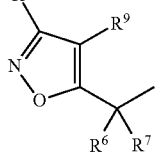

(G⁷-16)

-continued
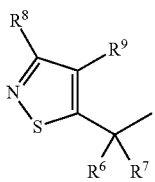
(G⁷-17)
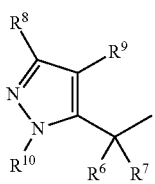
(G⁷-18)
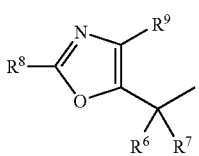
(G⁷-19)
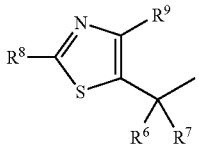
(G⁷-20)
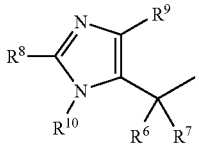
(G⁷-21)
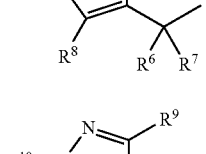
(G⁷-22)
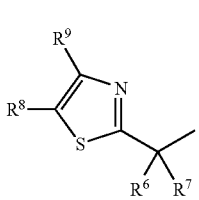
(G⁷-23)
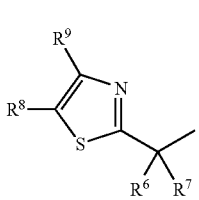
(G⁷-24)
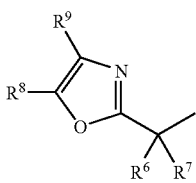
(G⁷-25)
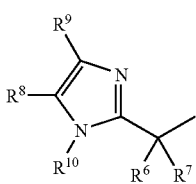
(G⁷-26)
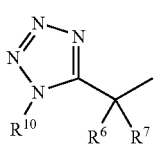
(G⁷-27)
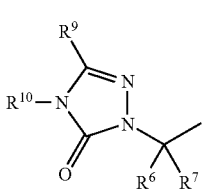
(G⁷-28)
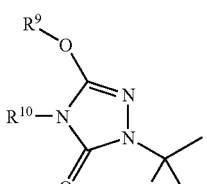
(G⁷-29)
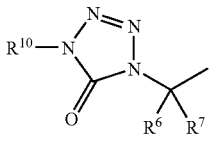
(G⁷-30)
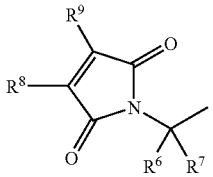
(G⁷-31)
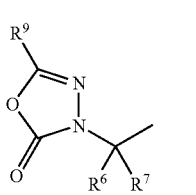
(G⁷-32)

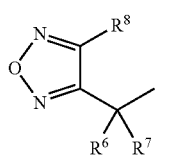 (G⁷-33)
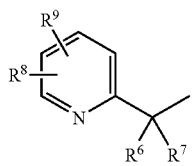 (G⁷-34)
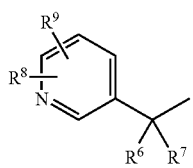 (G⁷-35)
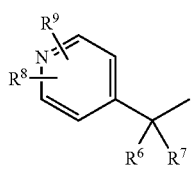 (G⁷-36)
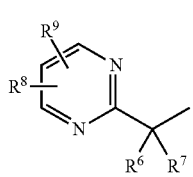 (G⁷-37)
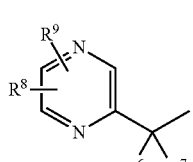 (G⁷-38)
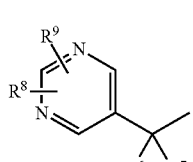 (G⁷-39)
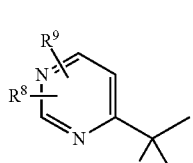 (G⁷-40)
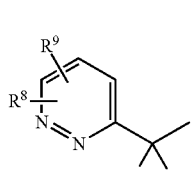 (G⁷-41)
 (G⁷-42)
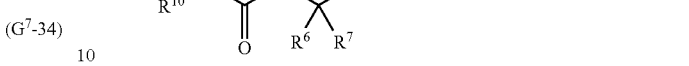 (G⁷-43)
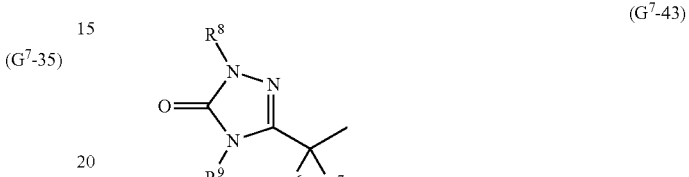 (G⁷-44)
 (G⁷-45)
or represents a radical selected from among the radicals (G⁸-1) to (G⁸-6)
 (G⁸-1)
 (G⁸-2)
 (G⁸-3)
 (G⁸-4)

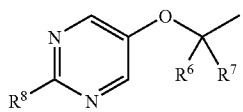 (G⁸-5)

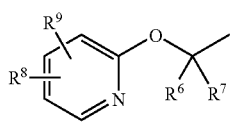 (G⁸-6)

in which $R^6$ and $R^7$ together with the carbon to which they are attached are selected from among the groupings (B-1) to (B-11) and

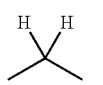 B-1

 B-2

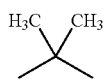 B-3

 B-4

 B-5

 B-6

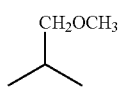 B-7

 B-8

 B-9

 B-10

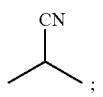 B-11 and $R^8$ preferably represents hydrogen, $C_{1-4}$-alkyl, in particular methyl, ethyl or propyl; $C_{1-4}$-haloalkyl, in particular trifluoromethyl or difluoromethyl; $C_{1-4}$-alkoxy, in particular methoxy, ethoxy; $C_{3-6}$-cycloalkyl, in particular cyclopropyl; $C_{1-4}$-alkoxy-$C_{1-4}$-alkoxy, in particular methoxyethoxy, ethoxyethoxy; $C_{1-4}$-haloalkoxy, in particular trifluoromethoxy or difluoromethoxy; $C_{1-4}$-alkylthio, in particular methylthio; $C_{1-4}$-alkylsulphinyl, in particular methylsulphinyl; $C_{1-4}$-alkylsulphonyl, in particular methylsulphonyl; $C_{1-4}$-haloalkylthio, in particular trifluoromethylthio; $C_{1-4}$-haloalkylsulphinyl, in particular trifluoromethylsulphinyl; $C_{1-4}$-haloalkylsulphonyl, in particular trifluoromethylsulphonyl; hetaryl, in particular pyridyl; halogen, in particular fluorine, chlorine, bromine or iodine; nitro; cyano; amino; $C_{1-4}$-alkylamino, in particular methylamino, ethylamino, di-($C_{1-4}$-alkyl)-amino, in particular dimethylamino, diethylamino, or preferably represents a radical from the group consisting of CO—OH; COO⁽⁻⁾; COO—$C_{1-6}$-alkyl; P(O)(OH)₂; P(O)O⁽⁻⁾₂; CO—NH₂; CS—NH₂; C(=NH)—NH₂; C(=N—OH)—NH₂; CO—NH—$C_{1-4}$-alkyl, in particular CO—NHCH₃; CO—N—($C_{1-4}$-alkyl)₂, in particular CO—N(CH₃)₂; CO—NH—$C_{1-4}$-alkoxy, in particular CO—NHOCH₃; CO—NH—CO—$C_{1-4}$-alkyl, in particular CO—NH—COCH₃; CO—NH—CO—$C_{1-4}$-haloalkyl, in particular CO—NH—COCF₃; CO—NH—CO—$C_{3-7}$-cycloalkyl, in particular CO—NH—CO-cyclopropyl; CO—NH—CO—$C_{1-4}$-alkoxy, in particular CO—NH—COOCH₃; CO—NH-00-(aryl-$C_{1-2}$-alkyloxy), in particular CO—NH-00-O-benzyl; SO₂—OH, SO₂—O⁽⁻⁾; SO₂—NH₂, SO₂—NH—$C_{1-4}$-alkyl, in particular SO₂—NHCH₃, SO₂—N—($C_{1-4}$-alkyl)₂; in particular SO₂—N(CH₃)₂; CO—NH—SO₂—NH—$C_{1-4}$-alkyl, in particular CO—NH—SO₂—NHCH₃;

CO—NH—SO₂—N[di($C_{1-4}$-alkyl), in particular CO—NH—SO₂—N(CH₃)₂; and $R^9$ preferably represents hydrogen; $C_{1-4}$-alkyl, in particular methyl, ethyl, n-propyl, isopropyl, butyl; $C_{1-4}$-haloalkyl in particular trifluoromethyl or difluoromethyl; $C_{1-4}$-alkoxy, in particular methoxy, ethoxy; $C_{1-4}$-haloalkoxy, in particular trifluoromethoxy or difluoromethoxy; $c_{1-4}$-alkylthio, in particular methylthio; $c_{1-4}$-alkylsulphinyl, in particular methylsulphinyl; $c_{1-4}$-alkylsulphonyl, in particular methylsulphonyl; halogen, in particular fluorine, chlorine, bromine or iodine; nitro; cyano; formyl; $C_{1-4}$-alkylcarbonyl, in particular acetyl; amino; $C_{1-4}$-alkylamino, in particular methylamino, ethylamino; di-($C_{1-4}$-alkyl)-amino, in particular dimethylamino, diethylamino; optionally substituted aryl, in particular phenyl, 2-, 3- or 4-chlorophenyl; optionally substituted pyridyl, in particular 3-chloropyrid-2-yl, 2-bromopyrid-2-yl, optionally substituted heterocyclyl, in particular piperidinyl, piperazinyl or morpholinyl; and $R^{10}$ preferably represents $C_{1-4}$-alkyl, in particular methyl, ethyl, n-propyl, isopropyl, butyl; $C_{1-4}$-haloalkyl, in particular trifluoromethyl or difluoromethyl; $C_{1-4}$-alkyl-carbonyl, in particular acetyl; $C_{1-4}$-alkoxycarbonyl, in particular methoxycarbonyl, ethoxycarbonyl, tert-butoxycarbonyl, or $R^4$ represents a radical selected from the radicals (G⁹-1) to (G⁹-5)

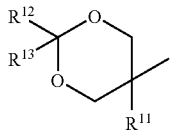 (G⁹-1)

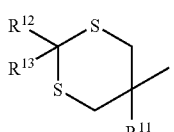 (G⁹-2)

-continued

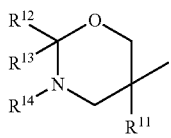
(G⁹-3)

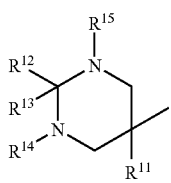
(G⁹-4)

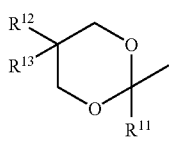
(G⁹-5)

in which
$R^{11}$ represents hydrogen, cyano, $C_{1-4}$-alkyl, in particular methyl, ethyl, n-propyl, n-butyl, isopropyl, isobutyl or sec-butyl, and $R^{12}$ and $R^{13}$ independently of one another preferably represent hydrogen, $C_{1-4}$-alkyl, in particular methyl, ethyl, n-propyl, n-butyl, isopropyl, isobutyl or sec-butyl; $C_{2-4}$-alkenyl, in particular 1-propenyl; $C_{2-4}$-alkynyl, in particular 1-propynyl; $C_{1-6}$-alkoxy-$C_{1-4}$-alkyl, in particular methoxyethyl or ethoxyethyl; amino-$C_{1-4}$-alkyl, in particular aminomethyl, aminoethyl, aminopropyl or aminobutyl; $C_{1-6}$-alkylamino-$C_{1-4}$-alkyl, in particular methylaminomethyl; di-($C_{1-6}$-alkyl)-amino-$C_{1-4}$-alkyl, in particular N,N-dimethylaminomethyl, hydroxymethyl; aryloxy-$C_{1-4}$-alkyl, in particular benzyloxymethyl; $C_{1-6}$-alkylcarbonyl, in particular acetyl; optionally substituted aryl, in particular optionally substituted phenyl; aryl-$C_{1-4}$-alkyl, in particular benzyl or phenethyl, hetaryl, in particular pyridyl, pyrimidyl, pyrazinyl, pyrazolyl, thiazolyl, thienyl, furyl; hetaryl-$C_{1-4}$-alkyl, in particular pyridylmethyl, pyridylethyl, pyrazinylmethyl, pyrimidylmethyl, thiazolylmethyl which may optionally be substituted by at least one substituent selected from the group consisting of fluorine, chlorine, bromine and iodine, $C_{1-4}$-alkyl, in particular methyl, ethyl, isopropyl, $C_{3-6}$-cycloalkyl, in particular cyclopropyl, cyclobutyl, cyclopentyl or cyclohexyl, $C_{3-6}$-cycloalkoxy, in particular cyclopropoxy, cyclobutoxy, cyclopentoxy or cyclohexoxy, $C_{3-6}$-cycloalkyl-$C_{1-2}$-alkoxy, in particular cyclopropylmethoxy or cyclopropylethoxy, $C_{1-4}$-haloalkyl, in particular trifluoromethyl, amino, hydroxyl, nitro, cyano, $SO_2OH$, $COOH$, formyl, $C_{1-4}$-alkoxy, in particular methoxy, ethoxy, isopropoxy, $C_{1-2}$-alkylenedioxy, in particular methylenedioxy or ethylenedioxy, alkyleneoxy, in particular $H_2C=C(CH_3)-O-$, haloalkdioxy, $C_{1-4}$-haloalkoxy, in particular trifluoromethoxy, difluoromethoxy, tetrafluoroethoxy, $C_{1-4}$-alkylthio, in particular methylthio, $C_{1-4}$-alkylsulphinyl, in particular methylsulphinyl, $C_{1-4}$-alkylsulphonyl, in particular methylsulphonyl, $C_{1-4}$-haloalkylthio, in particular trifluoromethylthio, $C_{1-4}$-haloalkylsulphoxyl, in particular trifluoromethylsulphoxyl, $C_{1-4}$-haloalkylsulphonyl, in particular trifluoromethylsulphonyl, $C_{1-4}$-alkylamino, in particular methylamino, di-($C_{1-4}$-alkyl)-amino, in particular N,N-dimethylamino, N,N-diethylamino, $C_{1-4}$-alkylcarbonyl, in particular methylcarbonyl, ethylcarbonyl, $C_{3-6}$-cycloalkylcarbonyl, in particular cyclopropylcarbonyl, phenylcarbonyl, $C_{1-4}$-alkoxycarbonyl, in particular methoxycarbonyl, ethoxycarbonyl; and $R^{13}$ preferably represents hydrogen, $C_{1-4}$-alkyl, in particular methyl, ethyl, n-propyl, n-butyl, isopropyl, isobutyl or sec-butyl, $C_{2-4}$-alkenyl, in particular 1-propenyl, $C_{2-4}$-alkynyl, in particular 1-propynyl, $C_{1-6}$-alkoxy-$C_{1-4}$-alkyl, in particular methoxyethyl or ethoxyethyl, $C_{1-6}$-alkylamino-$C_{1-4}$- alkyl, in particular methylaminomethyl, di-($C_{1-6}$-alkyl)-amino-$C_{1-4}$-alkyl, in particular N,N-dimethylaminomethyl, hydroxymethyl, aryloxy-$C_{1-4}$-alkyl, in particular benzyloxymethyl, $C_{1-6}$-alkylcarbonyl, in particular acetyl, optionally substituted aryl, in particular optionally substituted phenyl, optionally substituted aryl-$C_{1-4}$-alkyl, in particular optionally substituted benzyl, optionally substituted hetaryl, in particular pyridyl; and $R^{14}$ preferably represents hydrogen, $C_{1-4}$-alkyl, in particular methyl, ethyl, n-propyl, n-butyl, isopropyl, isobutyl or sec-butyl;

$R^{15}$ preferably represents hydrogen, $C_{1-4}$-alkyl, in particular methyl, ethyl, n-propyl, n-butyl, isopropyl, isobutyl or sec-butyl;

or $R^4$ represents a radical selected from the radicals ($G^{16}$-1) to ($G^{10}$-3)

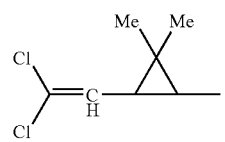
(G¹⁰-1)

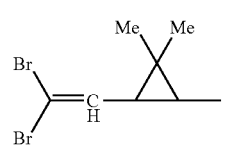
(G¹⁰-2)

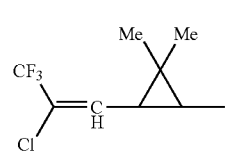
(G¹⁰-3)

or $R^4$ represents a radical ($G^{11}$-1)

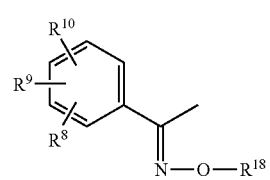
(G¹¹-1)

in which the radicals $R^8$, $R^9$, $R^{10}$ have the meaning mentioned above; and $R^{18}$ preferably represents optionally substituted $C_{1-4}$-alkyl, in particular methyl, ethyl;

or $R^4$ represents a radical ($G^{12}$-1) or ($G^{14}$-1)

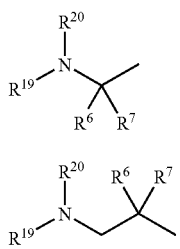
(G¹²-1)

(G¹⁴-1)

in which R⁶ and R⁷ have the meaning mentioned above; and R¹⁹ and R²⁰ independently of one another preferably represent hydrogen or optionally substituted $C_{1-4}$-alkyl, in particular methyl, ethyl, $C_{1-4}$-alkoxycarbonyl, in particular tert-butyloxycarbonyl, $C_{1-4}$-alkylcarbonyl, in particular acetyl, or R¹⁹ and R²⁰ together with the nitrogen atom to which they are attached preferably represent optionally substituted pyrrolidine, morpholine, thiomorpholine, 2,6-dimethylmorpholine, 3-oxomorpholine, optionally substituted piperidine, in particular tert-butyloxycarbonylamino-substituted or amino-substituted piperidine, optionally substituted piperazine, in particular tert-butyloxycarbonyl-substituted piperazine, N-benzylpiperazine, methyl-substituted piperazine or 2,5-diketomorpholine.

Particularly preferred groups, groupings, substituents and ranges of the radicals given in the formulae mentioned above and below are illustrated below.

Grouping —C₂₂R¹-A-C₂₃R²— particularly preferably represents —HC═CH— or —H₂C—CH₂—, R³ particularly preferably represents sec-butyl or isopropyl,
R⁵ particularly preferably represents hydrogen and
R⁴ particularly preferably represents a radical selected from the group consisting of ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, 2-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl and 2-ethylbutyl; cyclopropyl, 1-methylcyclobutyl, 1-cyanocyclopropyl, 1-fluorocyclopropyl, cyclopentyl, cyclopentenyl, cyclohexyl, methoxymethyl, methoxyethyl, ethoxymethyl, ethoxyethyl, methoxypropyl, ethoxypropyl, methoxybutyl, ethoxybutyl, 2-fluoroethyl, 3,3,3-trifluoroethyl, 2,2-dichlorocyclopropyl, aminomethyl, aminoethyl, aminopropyl, aminobutyl, N-methylaminomethyl, N-methylaminoethyl, N-methylaminopropyl, N-methylaminobutyl, N,N-dimethylaminomethyl, N,N-dimethylaminoethyl, N,N-dimethylaminopropyl, N,N-dimethylaminobutyl, N-ethyl-N-propylaminomethyl, N-ethyl, N-propylaminoethyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, thiazolylmethyl, 1,2,3-triazolyl-1-ylmethyl, 1,2,3-triazolyl-1-yl-2-ethyl, N-pyrazolylmethyl, N-pyrrolylmethyl, N-methylpyrrol-2-ylmethyl, furylmethyl, thien-3-ylmethyl, pyrid-2-ylmethyl, pyrid-3-ylmethyl, 1,2,3,4-tetrazol-1-ylmethyl which may optionally be substituted by at least one substituent selected from the group consisting of fluorine, chlorine, bromine, iodine, methyl, ethyl, cyclopropyl, cyclopropoxy, cyclopropylmethyl, trifluoromethyl, amino, hydroxyl, nitro, cyano, SO₂OH, COOH, formyl, methoxy, ethoxy, isopropoxy, methylenedioxy, ethylenedioxy, difluoromethoxy, tetrafluoroethoxy, trifluoromethoxy, methylthio, methylsulphonyl, trifluoromethylthio, trifluoromethylsulphoxyl, methylamino, N,N-dimethylamino, methylcarbonyl, cyclopropylcarbonyl, methoxycarbonyl, methoxyethoxymethyl, with the proviso that R⁴ does not represent 4-chlorophenyl, or R⁴ represents a radical selected from the radicals below

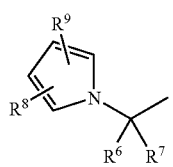
(G⁷-1)

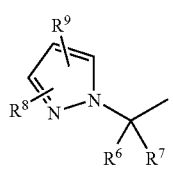
(G⁷-2)

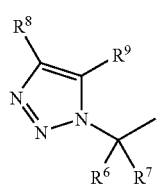
(G⁷-3)

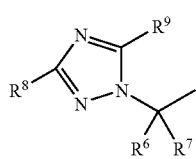
(G⁷-4)

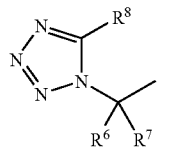
(G⁷-5)

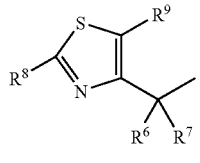
(G⁷-6)

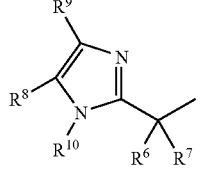
(G⁷-8)

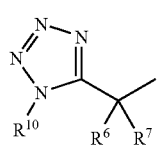
(G⁷-9)

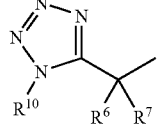

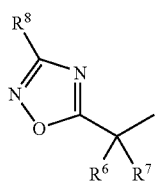 (G⁷-10)
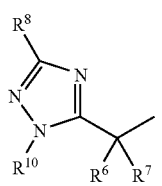 (G⁷-12)
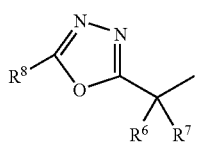 (G⁷-13)
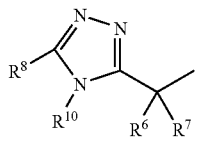 (G⁷-15)
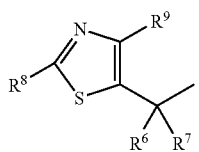 (G⁷-17)
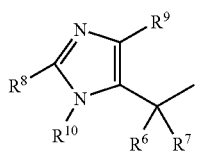 (G⁷-21)
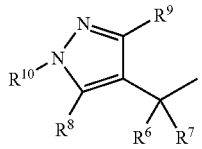 (G⁷-22)
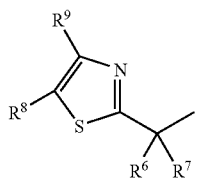 (G⁷-24)
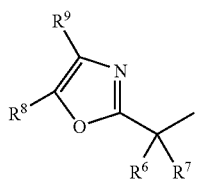 (G⁷-25)
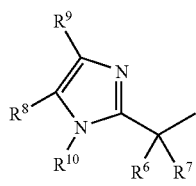 (G⁷-26)
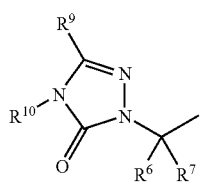 (G⁷-28)
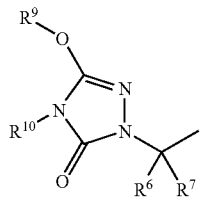 (G⁷-29)
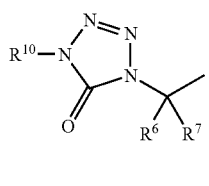 (G⁷-30)
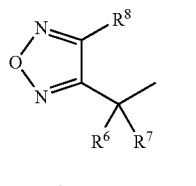 (G⁷-33)
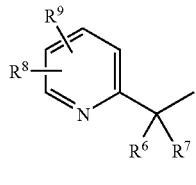 (G⁷-34)
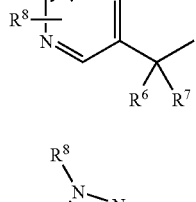 (G⁷-35)
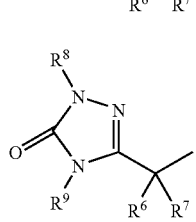 (G⁷-43)

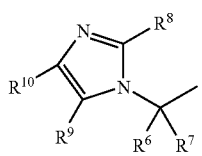
(G⁷-44)

or represents a radical (G¹²-1) or (G¹⁴-1)

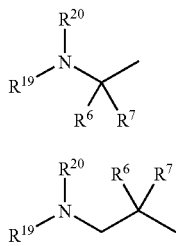

(G¹²-1)

(G¹⁴-1)

in which
R⁶ and R⁷ together with the carbon to which they are attached are particularly preferably selected from the groupings (B-1), (B-2), (B-3), (B-9) and (B-10)

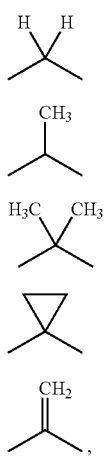

B-1

B-2

B-3

B-9

B-10

R⁸ represents hydrogen, methyl, trifluoromethyl, difluoromethyl, methoxy, methoxyethoxy, trifluoromethoxy, difluoromethoxy, methylthio, methylsulphinyl, methylsulphonyl, trifluoromethylthio, trifluoromethylsulphinyl, trifluoromethylsulphonyl, cyclopropyl, pyridyl, thienyl, fluorine, chlorine, bromine, iodine, nitro, cyan, amino, methylamino, dimethylamino, diethylamino or is selected from the group consisting of CO—OH, COO$^{(-)}$, COO—$C_{1-6}$-alkyl, CO—NH$_2$, CS—NH$_2$, C(=NH)—NH$_2$, C(=N—OH)—NH$_2$, CO—NHCH$_3$, CO—N(CH$_3$)$_2$, CO—NHOCH$_3$, CO—NH—COCH$_3$, CO—NH—COOCH$_3$, CO—NH—CO—O-benzyl, SO$_2$—OH, SO$_2$—O$^{(-)}$, SO$_2$—NH$_2$, SO$_2$—NHCH$_3$, SO$_2$—N(CH$_3$)$_2$, CO—NH—SO$_2$—NHCH$_3$, CO—NH—SO$_2$—N(CH$_3$)$_2$;
R⁹ represents hydrogen, methyl, trifluoromethyl, methoxy, trifluoromethoxy, methylthio, methylsulphinyl, methylsulphonyl, fluorine, chlorine, bromine, iodine, nitro, cyano, formyl, acetyl, amino, methylamino, dimethylamino, diethylamino, phenyl, 2-, 3- or 4-chlorophenyl, 3-chloropyrid-2-yl, pyrid-4-yl, or 2-bromopyrid-2-yl; and
R¹⁰ represents hydrogen, methyl, ethyl, n-propyl, isopropyl, butyl, trifluoromethyl, difluoromethyl, acetyl, methoxycarbonyl, ethoxycarbonyl or tert-butoxycarbonyl,
or R⁴ represents a radical (G⁹-1)

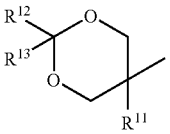
(G⁹-1)

in which R¹¹ represents methyl, and
R¹² and R¹³ independently of one another represent hydrogen, methyl, ethyl, n-propyl, n-butyl, isopropyl, 1-propenyl, methoxyethyl, ethoxyethyl, methylaminomethyl, N,N-dimethylaminomethyl, hydroxymethyl, benzyloxymethyl, acetyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, thiazolylmethyl which may optionally be substituted by at least one substituent selected from the group consisting of fluorine, chlorine, bromine, iodine, methyl, ethyl, isopropyl, cyclopropyl, cyclopropoxy, cyclopropylmethoxy, trifluoromethyl, amino, hydroxy, nitro, cyano, SO$_2$OH, COOH, formyl, methoxy, ethoxy, isopropoxy, methylenedioxy, ethylenedioxy, difluoromethoxy, tetrafluoroethoxy, trifluoromethoxy, methylthio, methylsulphonyl, trifluoromethylthio, trifluoromethylsulphoxyl, methylamino, N,N-dimethylamino, methylcarbonyl, cyclopropylcarbonyl, methoxycarbonyl, and
R¹⁹ and R²⁰ independently of one another represent hydrogen or optionally substituted $C_{1-4}$-alkyl, in particular methyl; $C_{1-4}$-alkoxycarbonyl, in particular tert-butyloxycarbonyl; $C_{1-4}$-alkylcarbonyl, in particular acetyl, or
R¹⁹ and R²⁰ together with the nitrogen atom to which they are attached represent optionally substituted pyrrolidine, morpholine, 2,6-dimethylmorpholine, 3-oxomorpholine; optionally substituted piperidine, in particular tert-butyloxycarbonylamino-substituted piperidine or amino-substituted piperidine; optionally substituted piperazine, in particular tert-butyloxycarbonyl-substituted piperazine or methyl-substituted piperazine Very particularly preferred groups, groupings, substituents and ranges of the radicals given in the formulae mentioned above and below are illustrated below.
The grouping —C$_{22}$R¹-A-C$_{23}$R²— very particularly preferably represents —HC=CH— or —H$_2$C—CH$_2$—,
R³ very particularly preferably represents sec-butyl, R⁵ very particularly preferably represents hydrogen and
R⁴ very particularly preferably represents a radical selected from the group consisting of ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, 2-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl and 2-ethylbutyl; cyclopropyl, 1-methylcyclobutyl, cyanocyclopropyl, 1-fluorocyclopropyl, aminomethyl, aminoethyl, N-methylaminomethyl, N-methylaminoethyl, N,N- dimethylaminomethyl, N,N-dimethylaminoethyl, cyclohexyl, methoxymethyl, methoxyethyl, 2-fluoroethyl, 3,3,3-trifluoroethyl, 2,2-dichlorocyclopropyl, phenethyl, pyridylmethyl, pyridylethyl, pyrazinylmethyl, pyrimidylmethyl, 1,2,3-triazol-1-ylmethyl, N-pyrazolylmethyl, N-pyrrolylmethyl, N-methylpyrrol-2-ylmethyl, 1,2,3,4-tetrazol-1-ylmethyl, which may optionally be substituted by at least one substituent selected from the group consisting of fluorine, chlorine, bromine, iodine, methyl, trifluoromethyl, amino, hydroxyl, $SO_2OH$, COOH, formyl, methoxy, trifluoromethoxy, difluoromethoxy, methylamino, N,N-dimethylamino, methylcarbonyl, cyclopropylcarbonyl, methoxycarbonyl, or represents a radical selected from the radicals below

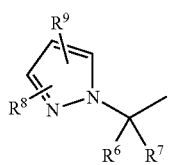
(G$^7$-2)

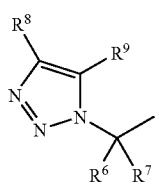
(G$^7$-3)

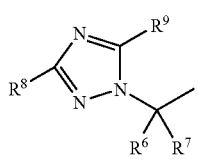
(G$^7$-4)

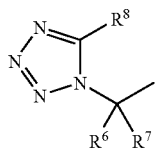
(G$^7$-5)

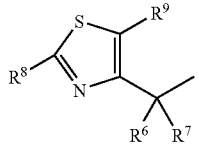
(G$^7$-6)

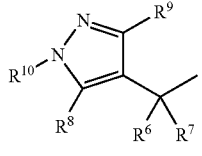
(G$^7$-22)

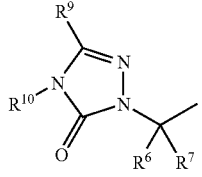
(G$^7$-28)

-continued

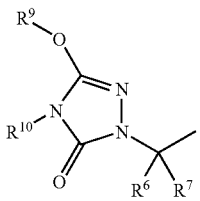
(G$^7$-29)

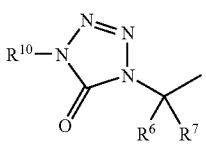
(G$^7$-30)

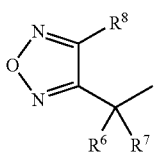
(G$^7$-33)

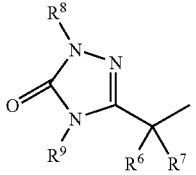
(G$^7$-43)

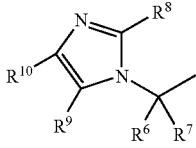
(G$^7$-44)

or represents a radical (G$^{12}$-1) or (G$^{14}$-1)

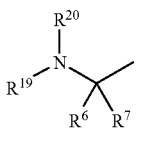
(G$^{12}$-1)

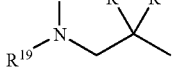
(G$^{14}$-1)

in which

R$^6$ and R$^7$ together with the carbon atom to which they are attached are very particularly preferably selected from the groupings (B-1), (B-2) (B-3) and (B-9)

B-1

B-2

-continued

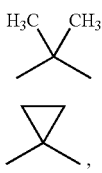

B-3

B-9

$R^8$ represents hydrogen, methyl, trifluoromethyl, methoxy, trifluoromethoxy, fluorine, chlorine, bromine, iodine, methylamino or dimethylamino or is selected from the group consisting of CO—NH$_2$, CO—NHCH$_3$, CO—N(CH$_3$)$_2$, CO—NHOCH$_3$, CO—NH—COCH$_3$, CO—NH—COOCH$_3$, CO—NH—CO—O-benzyl, SO$_2$—NH$_2$, SO$_2$—NHCH$_3$, SO$_2$—N(CH$_3$)$_2$, CO—NH—SO$_2$—NHCH$_3$, CO—NH—SO$_2$—N(CH$_3$)$_2$;

$R^9$ represents hydrogen, methyl, trifluoromethyl, methoxy, trifluoromethoxy, fluorine, chlorine, bromine, iodine, acetyl, methylamino, dimethylamino, diethylamino, phenyl, 4-chlorophenyl, pyrid-4-yl, $R^{10}$ represents methyl, acetyl, methoxycarbonyl, tert-butoxycarbonyl, or very particularly preferably represents a radical from groups (G$^3$) and (G$^9$) below

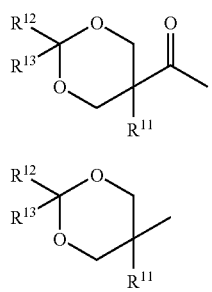

in which $R^{11}$ represents methyl, and $R^{12}$ and $R^{13}$ independently of one another represent methyl, methoxyethyl, methylaminomethyl, or $R^{12}$ represents hydrogen, and $R^{13}$ represents methyl, ethyl, n-propyl, 1-propenyl, methoxyethyl, ethoxyethyl, methylaminomethyl, N,N-dimethylaminomethyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, thiazolylmethyl which may optionally be substituted by at least one substituent selected from the group consisting of fluorine, chlorine, bromine, iodine, methyl, ethyl, isopropyl, cyclopropyl, cyclopropoxy, cyclopropylmethoxy, trifluoromethyl, amino, hydroxyl, nitro, cyano, SO$_2$OH, COOH, formyl, methoxy, ethoxy, isopropoxy, methylenedioxy, ethylenedioxy, difluoromethoxy, tetrafluorethoxy, trifluoromethoxy, difluoromethoxy, methylthio, methylsulphonyl, trifluoromethylthio, trifluoromethylsulphoxyl, methylamino, N,N-dimethylamino, methylcarbonyl, cyclopropylcarbonyl, methoxycarbonyl.

$R^{19}$ and $R^{20}$ independently of one another represent hydrogen, methyl, ethyl, tert-butyloxycarbonyl, acetyl, or $R^{19}$ and $R^{20}$ together with the nitrogen atom to which they are attached represent pyrrolidine, morpholine, 2,6-dimethylmorpholine, 3-oxomorpholine, piperidine, tert-butyloxycarbonylamino-substituted piperidine or 4-amino-substituted piperidine, piperazine, tert-butyloxycarbonyl-substituted piperazine or 4-methyl-substituted piperazine The general or preferred radical definitions or illustrations given above apply to end products according to the invention and likewise to starting materials and intermediates. These radical definitions can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

Depending, if appropriate, on the nature of the substituents, inter alia, the compounds of the formula (I) may be present as stereoisomers, i.e. as geometrical and/or optical isomers or isomer mixtures of varying compositions. According to the invention, the formula (I) thus includes both the pure stereoisomers and any mixtures of these isomers, which are thus also provided by the invention.

The invention also relates to compounds of the formula (I) which may be present in the form of an acid addition salt. Acids which are used for forming such a salt are generally known and are, for example, inorganic acids, such as hydrochloric acid, hydrobromic acid, nitric acid, sulphuric acid, phosphoric acid, or organic acids, such as formic acid, acetic acid, propionic acid, malonic acid, oxalic acid, fumaric acid, adipic acid, stearic acid, tartaric acid, oleic acid, methanesulphonic acid, benzenesulphonic acid, benzenecarboxylic acid or toluenesulphonic acid.

Suitable salts of the compounds of the formula (I) which may be mentioned are customary salts, i.e. salts with various bases and salts with added acids which are not toxic. Preference is given to salts with inorganic bases, such as alkali metal salts, for example sodium salts, potassium salts or caesium salts, alkaline earth metal salts, for example calcium salts or magnesium salts, ammonium salts, salts with organic bases, and also with organic amines, for example triethylammonium, pyridinium, picolinium, ethanolammonium, triethanolammonium, dicyclohexylammonium- or N,N'-dibenzyl-ethylenediammonium salts, salts with inorganic acids, for example hydrochlorides, hydrobromides, dihydrogensulphates or trihydrogenphosphates, salts with organic carboxylic acids or organic sulphonic acids, for example formates, acetates, trifluoroacetates, maleates, tartrates, methanesulphonates, benzenesulphonates, benzoates or para-toluenesulphonates, salts with basic amino acids or acidic amino acids, for example arginates, aspartates or glutamates.

If, to prepare the novel avermectin derivatives according to the invention, for example abarmectin as compound of the formula (II) and for example cyclopropylcarboxylic acid as compound of the formula (V) are reacted in the presence of a basic reaction auxiliary, the abovementioned preparation process, which proceeds over four reaction steps, can be represented by the reaction scheme below:

Reaction scheme I
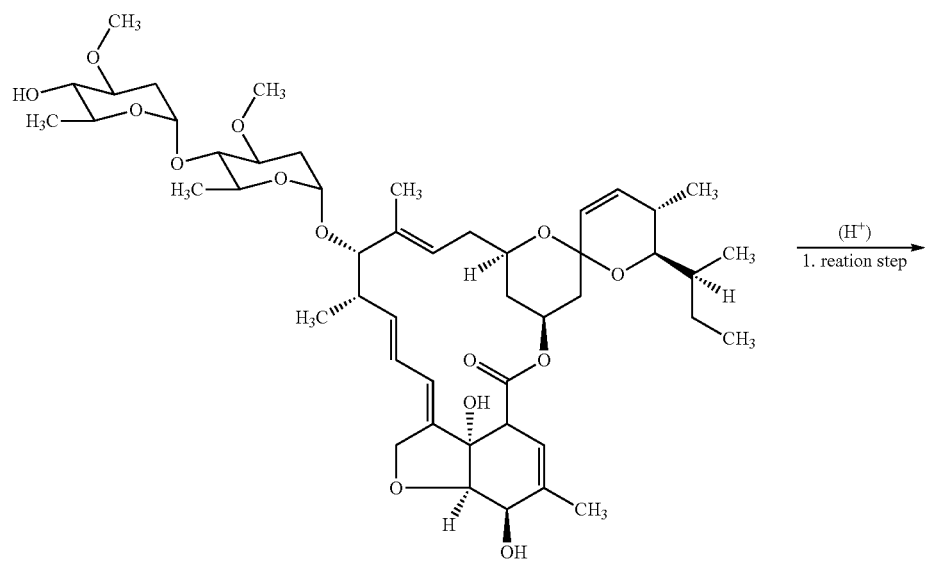
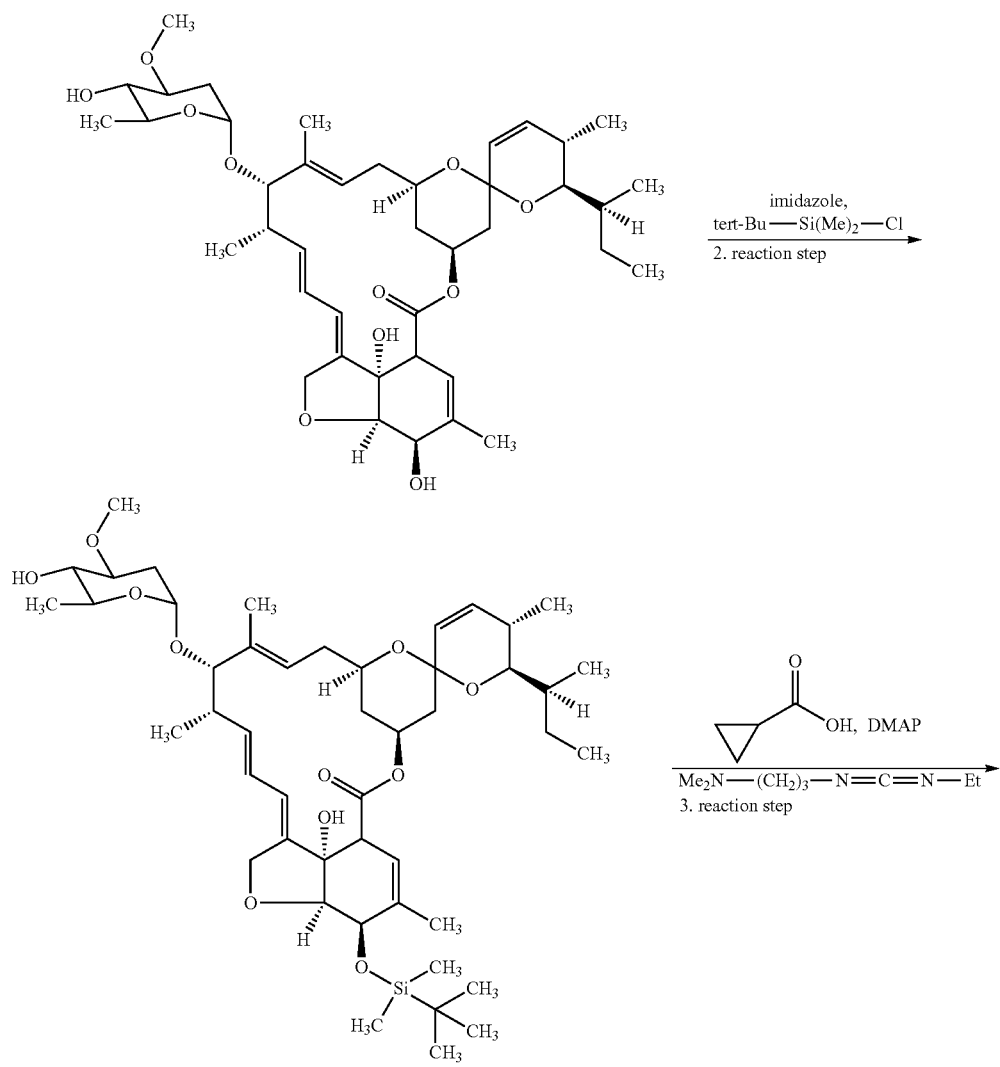

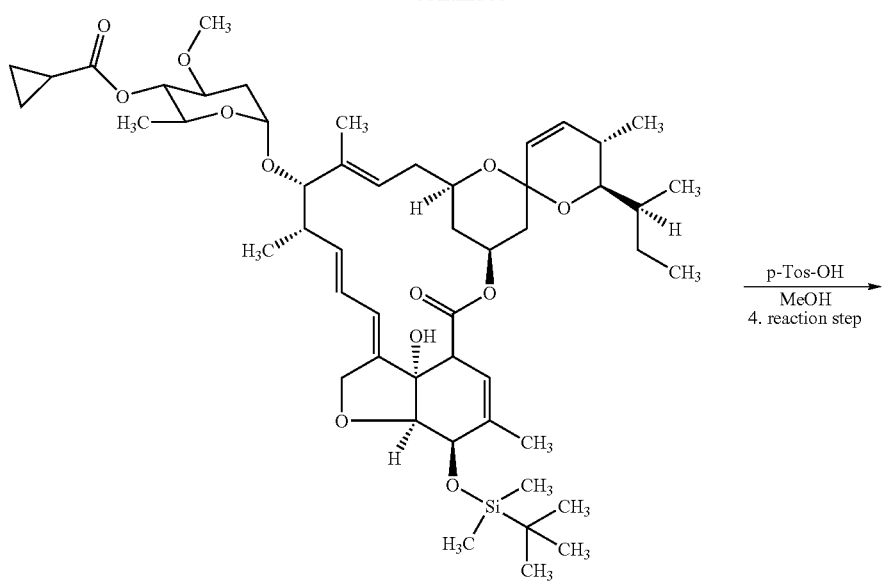
$\xrightarrow[\text{4. reaction step}]{\text{p-Tos-OH} \atop \text{MeOH}}$
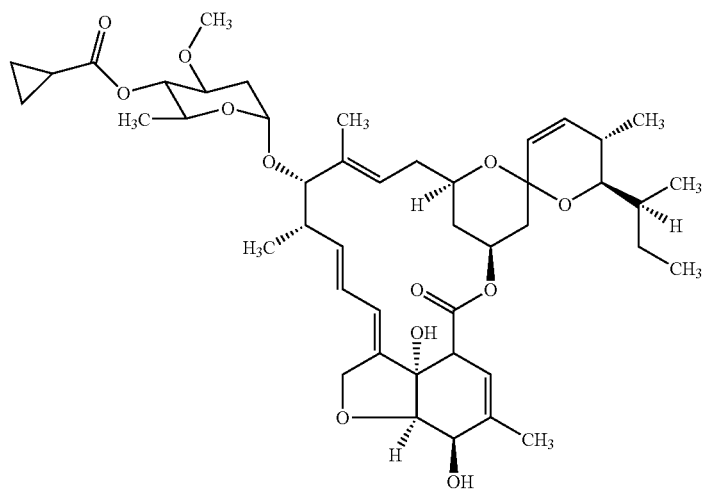

Suitable for use as starting materials of the formula (II) are macrocyclic lactones, in particular avermectins and derivatives thereof. Avermectins can be isolated from the microorganism *Strepomyces avermitilis* as microbial metabolites (cf. U.S. Pat. No. 4,310,519) and essentially occurs as a mixture comprising eight components $A_{1a}$, $A_{1b}$, $A_{2a}$, $A_{2b}$, $B_{1a}$, $B_{1b}$, $B_{2a}$ and $B_{2b}$, (I. Putter et al., Experentia (1981) 37, p. 963, Birkhäuser Verlag, Switzerland). Other suitable starting materials include avermectins isolated as microbial metabolites and also synthetic derivatives of the macrocyclic lactones, such as, in particular, 22,23-dihydroavermectin $B_1$ (ivermectin $B_1$). Particularly suitable starting materials according to the invention are substance mixtures of macrocyclic lactones of the formula (II)

The macrocyclic lactones carrying an isopropyl radical in the $C_{25}$-position, which are marked with the "b" in the table above, do not necessarily have to be separated from the lactones carrying a sec-butyl group in the $C_{25}$-position, which are marked with the "a" in the table above. What is isolated is generally a mixture of both lactones consisting of >80% of sec-butyl derivatives ($B_{1a}$) and <20% of isopropyl derivative ($B_{1b}$), which mixture is a suitable starting material according to the invention. Also suitable for use as starting material is a mixture consisting of >80% of sec-butyl derivatives ($B_{2a}$) and <20% of isopropyl derivative ($B_{2b}$) or >80% of sec-butyl derivatives ($A_{1a}$) and <20% of isopropyl derivative ($A_{1b}$).

Additionally, in the case of stereoisomers, the substituents in the $C_{13}$- and $C_{23}$-positions may be arranged either in an α-

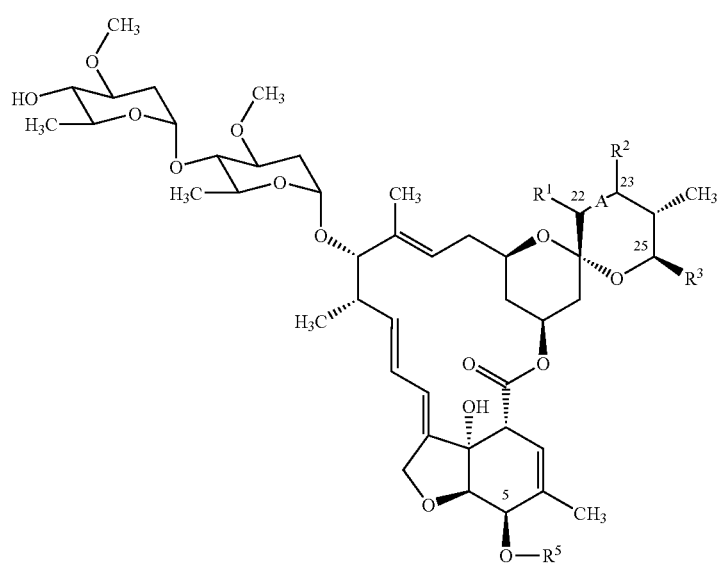

(II)

in which the radicals $R^1$, $R^2$, $R^3$ and $R^5$ have the meanings stated in the table below (Table 1).

TABLE 1

| Macrocyclic lactones of the formula (II) | —$C_{22}R^1$—A—$C_{23}R^2$— | $R^3$ | $R^5$ |
|---|---|---|---|
| avermectin $A_{1a}$ | —HC═CH— | sec-butyl | methyl |
| avermectin $A_{1b}$ | —HC═CH— | iso-propyl | methyl |
| avermectin $A_{2a}$ | —H$_2$C—CH(OH)— | sec-butyl | methyl |
| avermectin $A_{2b}$ | —H$_2$C—CH(OH)— | iso-propyl | methyl |
| avermectin $B_{1a}$ | —HC═CH— | sec-butyl | h |
| avermectin $B_{1b}$ | —HC═CH— | iso-propyl | h |
| avermectin $B_{2a}$ | —H$_2$C—CH(OH)— | sec-butyl | h |
| avermectin $B_{2b}$ | —H$_2$C—CH(OH)— | iso-propyl | h |
| 22,23-dihydroavermectin $B_{1a}$ (=ivermectin $B_1$) | —H$_2$C—CH$_2$— | sec-butyl | h |
| 22,23-dihydroavermectin $B_{1b}$ (=ivermectin $B_1$) | —H$_2$C—CH$_2$— | iso-propyl | h |
| doramectin | —HC═CH— | cyclohexyl | h |

In general, the avermectins and 22,23-dihydroavermectin $B_1$ (ivermectin $B_1$) of the formula (II) are employed as mixtures. Particular mention may be made here of abamectin, which essentially comprises the avermectins $B_1$ and their hydrogenation products, the 22,23-dihydroavermectins $B_1$ (ivermectin $B_1$).

or in a β-orientation in the ring system, i.e. they may be above or below the molecular plane. In each case, the invention takes into account all stereoisomers.

From the class of the macrocyclic lactones the use of abamectin or 22,23-dihydroavermectin $B_1$ (ivermectin $B_1$) as pesticides and endoparaciticides is known and is the subject of numerous reviews, for example B. D. J. Wright "Avermectins: action on target pest species", Biochem. Soc. Trans. (1987) 15, 65-67; L. Strong, T. A. Brown, "Avermectins in insect control and biology: a review", Bull. Entomol. Res. (1987), 77, 357-389; J. A. Lasota, R. A. Dybas, "Abamectin as a pesticide for agricultural use", Acta Leidensia (1990), 59, 217-225; J. A. Lasota, R. A. Dybas, "Avermectins, a novel class of compounds: implications for use in arthropod pest control", Ann. Rev. Entomol. (1991) 36, 91-117; L. Strong "Overview: the impact of avermectins on pastureland ecology", Vet. Parasitol. (1993), 48, 3-17; W. "Ivermectin and Abamectin" (Ed. C. Campbell), Springer-Verlag, New York, N.Y. 1989; I. H. Sutherland, "Veterinary use of ivermectin", Acta Leidensia (1990) 59, 211-216; A. Datry, M. Thellier "Ivermectin, a broad spectrum antiparasitic drug", Presse medicale (Paris, France: 1983) (2002) 31, 607-611; R. O. Drummond "Effectiveness of ivermectin for control of arthropod pests of livestock", (1985) 7, 34-42; W. C. Campbell "Ivermectin, an antiparasitic agent" Med. Res. Rev.

(1993), 13, 61-79; G. A. Conder "Chemistry, pharmacology and safety: doramectin and selamectin" Macrocyclic Lactones in Antiparasitic Therapy (2002), 30-50; A. C. Goudie et al., "Doramectin—a potent novel endectozide", Vet. Parasitol. 1993, 49, 5-15).

Some compounds of the formula (III) are known and can be prepared according to methods described here or known from the literature.

Known compounds of the formula (III) are, for example, compounds in which a) —$C_{22}R^1$-A-$C_{23}R^2$— represents —HC=CH— and $R^3$ represents sec-butyl (JP 54-061198, EP 0 004 812, J. C. Chabala et al. J. Med. Chem. (1980), 23, 1134-1136, U.S. Pat. No. 4,201,861, H. Mrozik et al., J. Org. Chem. (1982), 47, 489-492, EP 0 411 897, WO 2002/012248, Q. Wu et al., Nongyao (2004), 43, 28-29, CN 1502239) or $R^3$ represents isopropyl (WO 93/018779, J. C. Chabala et al. J. Med. Chem. (1980), 23, 1134-1136) or $R^3$ represents cyclohexyl (U.S. Pat. No. 5,981,500, WO 94/015944); or b) —$C_{22}R^1$-A-$C_{23}R^2$— represents —$H_2C$—$CH_2$— and $R^3$ represents sec-butyl (JP 54-061198, U.S. Pat. No. 4,199,569, EP 0 004 812, J. C. Chabala et al. J. Med. Chem. (1980), 23, 1134-1136, WO 93/018779, WO 94/015944, U.S. Pat. No. 5,981,500, WO 2002/012248) or $R^3$ represents isopropyl (EP 0 411 897, J. C. Chabala et al. J. Med. Chem. (1980), 23, 1134-1136, WO 93/018779) or $R^3$ represents cyclohexyl (U.S. Pat. No. 5,981,500, WO 94/015944, WO 94/029328, WO 95/003317); or c) —$C_{22}R^1$-A-$C_{23}R^2$— represents —$H_2C$—CH(OH)— and $R^3$ represents sec-butyl (JP 54-061198, U.S. Pat. No. 4,199,569, J. C. Chabala et al. J. Med. Chem. (1980), 23, 1134-1136, U.S. Pat. No. 4,201,861, EP 0 004 812, U.S. Pat. No. 4,206,205, H. Mrozik et al., J. Org. Chem. (1982), 47, 489-492) or $R^3$ represents isopropyl (J. C. Chabala et al. J. Med. Chem. (1980), 23, 1134-1136) or $R^3$ represents cyclohexyl (WO 94/029328).

Suitable acidic reaction auxiliaries are all mineral acids, organic acids or Lewis acids. Preferred mineral acids are hydrohalic acids, such as hydrofluoric acid, hydrochloric acid, hydrobromic acid or hydroiodic acid, sulphuric acid, phosphoric acid, phosphorous acid, nitric acid. Preferred organic acids are formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid. Preferred Lewis acids are aluminium(III) chloride, boron trifluoride or its etherate, titanium(V) chloride, tin(V) chloride.

The first reaction step is preferably carried out in the presence of mineral acids, in particular sulphuric acid.

For preparing compounds of the formula (IV) in which $R^4$ represents, for example, hydrogen, substituted methyl ethers and ethers, substituted ethyl ethers, substituted benzyl ethers, silyl ethers, esters, carbonates or sulphonates, for example, may be used as suitable protective groups for hydroxyl groups (cf. Greene T. W., Wuts P. G. W. in Protective Groups in Organic Synthesis; John Wiley & Sons, Inc. 1999, "Protection for the hydroxyl group including 1,2- and 1,3-diols").

Substituted methyl ether protective groups are, for example, methoxymethyl ether (MOM), methylthiomethyl ether (MTM), (phenyldimethylsilyl)methoxymethyl ether (SNOM-OR), benzyloxymethyl ether (BOM-OR), para-methoxybenzyloxymethyl ether (PMBM-OR), para-nitrobenzyloxymethyl ether, ortho-nitrobenzyloxymethyl ether (NBOM-OR), (4-methoxyphenoxy)-methyl ether (p-aOM-OR), guaiacolmethyl ether (GUM-OR), tert-butoxymethyl ether, 4-pentyloxy-methyl ether (POM-OR), silyloxymethyl ether, 2-methoxyethoxymethyl ether (MEM-OR), 2,2,2-trichloroethoxymethyl ether, bis(2-chloroethoxy)methyl ether, 2-(trimethylsilyl)ethoxymethyl ether (SEM-OR) or methoxymethyl ether (MM-OR).

Ether protective groups are, for example, tetrahydropyranyl ether (THP-OR), 3-bromotetra-hydropyranyl ether (3-BrTHP-OR), tetrahydrothiopyranyl ether, 1-methoxycyclohexyl ether, 2- and 4-picolyl ether, 3-methyl-2-picolyl-N-oxide ether, 2-quinolinylmethyl ether (Qm-OR), 1-pyrenylmethyl ether, diphenylmethyl ether (DPM-OR), para,para'-dinitrobenzhydryl ether (DNB-OR), 5-dibenzosuberyl ether, triphenylmethyl ether (Tr-OR), alpha-naphthyldiphenylmethyl ether, para-methoxyphenyldiphenylmethyl ether (MMTrOR), di(para-methoxyphenyl)phenylmethyl ether (DMTr-OR), tri(para-methoxyphenyl)phenylmethyl ether (TMTr-OR), 4-(4'-bromophenacyloxy)phenyldiphenylmethyl ether, 4,4',4''-tris(4,5-dichlorophthalimidophenyl)methyl ether (CPTr-OR), 4,4',4''-tris(benzoyloxyphenyl)methyl ether (TBTr-OR), 4,4'-dimethoxy-3''-[N-(imidazolylmethyl)]-trityl ether (IDTr-OR), 4,4'-dimethoxy-3''-[N-(imidazolylethyl)carbamoyl]trityl ether (IETr-OR), 1,1-bis(4-methoxyphenyl)-1'-pyrenylmethyl ether (Bmpm-OR), 9-anthryl ether, 9-(9-phenyl)-xanthenyl ether (Pixyl-OR), 9-(9-phenyl-10-oxo)anthryl ether (tritylone ether), 4-methoxy-tetrahydropyranyl ether (MTHP-OR), 4-methoxytetrahydrothiopyranyl ether, 4-methoxy-tetrahydrothiopyranyl S,S-dioxide, 1-[(2-chloro-4-methyl)phenyl]-4-methoxypiperidin-4-yl ether (CTMP-OR), 1-(2-fluorophenyl)-4-methoxypiperidin-4-yl ether (Fpmp-OR), 1,4-dioxan-2-yl ether, tetrahydrofuranyl ether, tetrahydrothiofuranyl ether, 2,3,3a,4,5,6,7,7a-octahydro-7,8,8-trimethyl-4,7-methanebenzofuran-2-yl ether (MBF-OR), tert-butyl ether, allyl ether, propargyl ether, para-chloro-phenylether, para-methoxyphenyl ether, para-nitrophenyl ether, para-2,4-dinitrophenyl ether (DNP-OR), 2,3,5,6-tetrafluoro-4-(trifluoromethyl)phenyl ether or benzyl ether (Bn-OR).

Substituted ethyl ether protective groups are, for example, 1-ethoxyethyl ether (EE-OR), 1-(2-chloroethoxy)ethyl ether (CEE-OR), 1-[2-(trimethylsilyl)ethoxy]ethyl ether (SEE-OR), 1-methyl-1-methoxyethyl ether (MIP-OR), 1-methyl-1-benzyloxyethyl ether (MBE-OR), 1-methyl-1-benzyloxy-2-fluoroethyl ether (MIP-OR), 1-methyl-1-phenoxyethyl ether, 2,2,2-trichloroethyl ether, 1,1-dianisyl-2,2,2-trichloroethyl ether (DATE-OR), 1,1,1,3,3,3-hexafluoro-2-phenylisopropyl ether (HIP-OR), 2-trimethylsilylethyl ether, 2-(benzylthio)ethyl ether or 2-(phenylselenyl)ethyl ether.

Substituted benzyl ether protective groups are, for example, para-methoxybenzyl ether (MPM-OR), 3,4-dimethoxybenzyl ether (DMPM-OR), ortho-nitrobenzyl ether, para-nitrobenzyl ether, para-halo-benzyl ethers, 2,6-dichlorobenzyl ether, para-aminoacylbenzyl ether (PAB-OR), para-azidobenzyl ether (Azb-OR), 4-azido-3-chlorobenzyl ether, 2-trifluoromethylbenzyl ether, or para-(methylsulphinyl)benzyl ether (Msib-OR).

Silyl ether protective groups are, for example, trimethylsilyl ether (TMS-OR), triethylsilyl ether (TES-OR), triisopropylsilyl ether (TIPS-OR), dimethylisopropylsilyl ether (IPDMS-OR), diethyliso-propylsilyl ether (DEIPS-OR), dimethylhexylsilyl ether (TDS-OR), tert-butyldimethylsilyl ether (TBDMS-OR), tert-butyldiphenylsilyl ether (TBDPS-OR), tribenzylsilyl ether, tri-para-xylylsilyl ether, triphenylsilyl ether (TPS-OR), diphenylmethylsilyl ether (DPMS-OR), di-tert-butylmethylsilyl ether (DTBMS-OR), tris(trimethylsilyl)silyl ether (sisyl ether), (2-hydroxylstyryl) dimethylsilyl ether (HSDMS-OR), (2-hydroxylstyryl) diisopropylsilyl ether (HSDIS-OR), tertbutylmethoxyphenylsilyl ether (TBMPS-OR) or tert-butoxydiphenylsilyl ether (DPTBOS-OR).

Ester protective groups are, for example, formate esters, benzoylformate esters, acetate esters (Ac-OR), chloroacetate esters, dichloroacetate esters, trichloroacetate esters, trifluoroacetate esters, (TFA-OR), methoxyacetate esters, triphenylmethoxyacetate esters, phenoxyacetate esters, para-chlorophenoxyacetate esters, phenylacetate esters, diphenylacetate esters (DPA-OR), nicotinate esters, 3-phenylpropionate esters, 4-pentoate esters, 4-oxopentoate esters (levulinates), (Lev-OR), 4,4-(ethylenedithio)pentanoate esters (LevS-OR), 5-[3-bis(4-methoxyphenyl)hydroxymethoxyphenoxy]levulinate esters, pivalate esters (Pv-OR), 1-adamantanoate esters, crotonate esters, 4-methoxycrotonate esters, benzoate esters (Bz-OR), para-phenylbenzoate esters, 2,4,6-trimethyl-benzoate esters (mesitoates), 4-(methylthiomethoxy)butyrate esters (MTMB-OR), or 2-(methylthio-methoxymethyl)benzoate esters (MTMT-OR).

Carbonate protective groups are, for example, methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMSEC-OR), 2-(phenylsulphonyl)ethyl carbonate (Psec-OR), 2-(triphenylphosphonio)ethyl carbonate (Peoc-OR), tert-butyl carbonate (Boc-OR), isobutyl carbonate, vinyl carbonate, allyl carbonate (Alloc-OR), para-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)ethyl carbonate (Npeoc-OR), 2-(2,4-dinitrophenyl)ethyl carbonate (Dnpeoc). Protective groups of the sulphate type which may be mentioned are, for example: allylsulphonate (Als-OR), methanesulphonate (Ms-OR), benzylsulphonate or tosylate (Ts-OR), 2-[(4-nitrophenyl)ethyl]sulphonate (Npes-OR).

Preferred protective groups for carrying out the preparation process according to the invention are those which have a say' radical, such as, for example, an SiMe$_2$-tert-Bu radical.

Some of the compounds of the formula (IV) are known and can be obtained by methods of the prior art. Known from the literature are, for example, the following compounds in which SG=SiMe$_2$-tert-Bu and in which
a) —C$_{22}$R$^1$-A-C$_{23}$R$^2$— represents —HC═CH$_2$— and R$^3$ represents sec-butyl (Ch. Bliard et al., J. Chem. Soc., Chem. Commun. (1987), 5, 368-370; U.S. Pat. No. 5,229,416; Y. Tsukamoto et al, Bioorg. Med. Chem. Lett. (2000) 8, 19-26, WO 2002012248, WO 2005021569) or R$^3$ represents isopropyl (EP 0 411 897 A2), WO 2005/021569); and
b) —C$_{22}$R$^1$-A-C$_{23}$R$^2$— represents —H$_2$C—CH$_2$— and R$^3$ represents sec-butyl (WO 2002/012 248, EP 0 411 997 A2) or R$^3$ represents isopropyl (U.S. Pat. No. 5,229,415) or R$^3$ represents cyclohexyl (U.S. Pat. No. 5,981,500, WO 94/015944, B. J. Banks et al., Bioorg. Med. Chem. Lett. (2000), 8, 2017-2025).

Suitable compounds of the formula (V) are carboxylic acids which are commercially available or can be prepared by methods known from the literature. General paths for preparing carboxylic acids of the formula (V) are described in reaction scheme III below:

Reaction scheme III

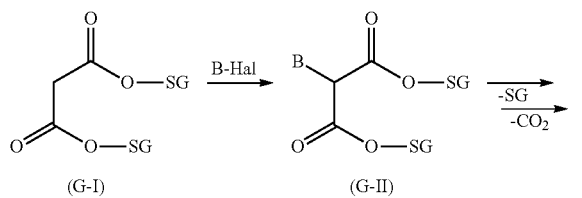

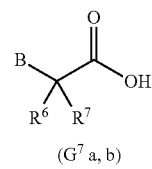

(R$^6$, R$^7$ = H)
B: optionally substituted (a) aryl, (b) hetaryl
O—SG: protective group, such as O-Me, O-tert-Bu, O-benzyl etc

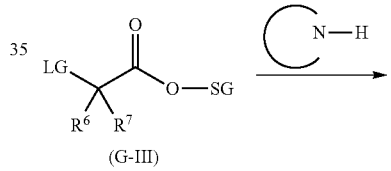

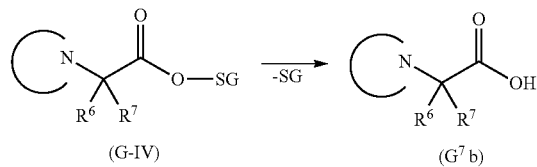

B = ⟨N—H⟩ h (b) Hetaryl (5-, 6- or 7-membered ring system) m)
LG = leaving group, such as halogen, O-Mes, O-Tos, O-Tf etc.
O—SG: protective group, such as O-Me, O-tert-Bu, O-benzyl etc

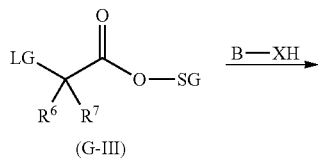

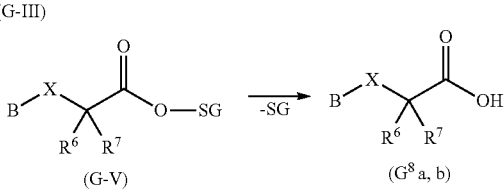

B: (a) aryl, (b) hetaryl (5-, 6- or 7- membered ring system)
LG: leaving group, such as Hal, O-Mes, O-Tos, O-Tf etc.
O—SG: protective group, e.g. B. OMe, O-tert-Bu, O-benzyl etc.

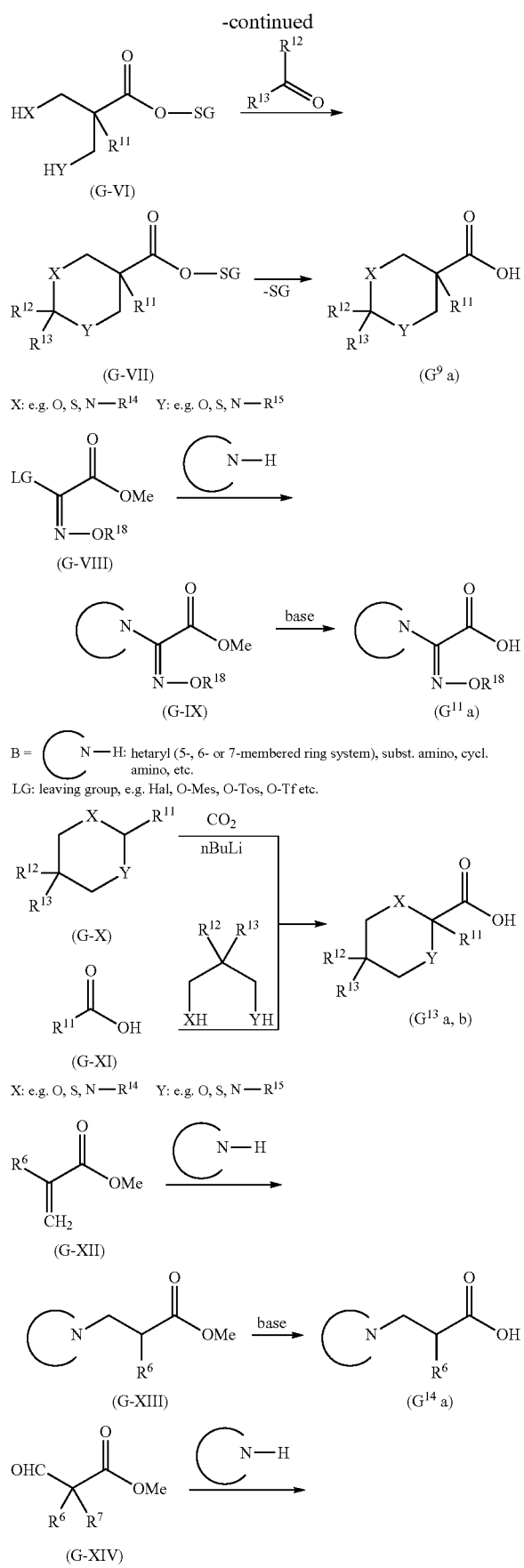
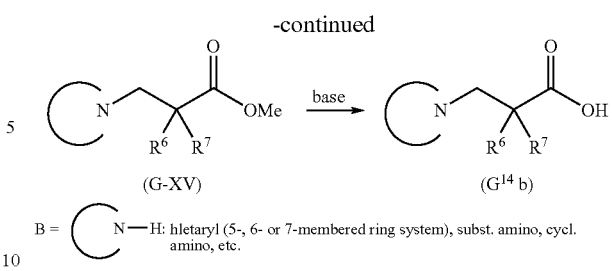

A general route for preparing (het)aryl-substituted carboxylic acids (G⁷a, b) consists, for example, in (het)arylating optionally protected malonic acid derivatives (G-I) and then O-deblocking the (het)arylmalonic acids (G-II) formed, followed by decarboxylation (for example (G⁷a): $R^6$, $R^7$=H, B=Phenyl: Synth. Commun (2000) 30, 2099-2104; (G⁷b): $R^6$, $R^7$=H, B=N-pyrazolyl: DE 19503827 A1). The N-hetaryl-substituted carboxylic acids (G⁷b) and (het)aryl-substituted carboxylic acids (G⁸a, b) can be obtained from the compounds (G-III). The protective group in the compounds (G-IV) or (G-V) is then removed by a procedure known from the literature (cf., for example, (G⁸a): $R^6$=H, $R^7$=Me, X=O, B=4-CF₃-phenyl: D. Kato et al., J. Org. Chem. (2003), 68, 7234-7242; (G⁸b): $R^6$=H, $R^7$=Me, X=O, B=3-Cl-pyrid-2-yl: D. Heilmann, G. Kempter, Wiss. Zeitschrift Paedag. Hochschule Karl Liebknecht Potsdam (1981), 25, 35-8).

To prepare the carboxylic acids (G⁹a), the compounds (G-VI) are cyclized with suitable carbonyl compounds (for example aldehydes if $R^{12}$ and/or $R^{13}$=H; ketones if $R^{12}$ or $R^{13}$=aryl, hetaryl, alkyl etc.) to give the functionalized ring systems (G-VII), which are then O-deblocked. If appropriate, the reaction may also be carried out without employing a protective group, for example if X, Y=O and SG=OH, (cf., for example, (G⁹a): $R^8$=Me, $R^{12}$, $R^{13}$=H: DE 1900202; $R^8$=Me, $R^{12}$=H, $R^{13}$=Ph: T. Parkkari et al., Bioorg. Med. Chem. Lett. (2004), 14, 3231-3234).

The use of the radicals (G¹⁰) and their preparation is sufficiently known (cf., for example, $R^{16}$, $R^{17}$=Me: S. Julia et al., Bull. Soc. Chim. Franc. (1966), 11, 3499-507; $R^{16}$, $R^{17}$=Cl: DE 2439177; $R^{16}$=Cl, $R^{17}$=CF₃: DE 2802962; $R^{16}$, $R^{17}$=Br: M. Elliott et al., Pest. Sci. (1975), 6, 537-42).

The use of the radicals (G¹¹) and their preparation is known, for example, from WO 2002/059078 A1. The use of methyl chloromethoximino acetate (G-VIII), in which LG=Cl and $R^{18}$=Me (cf. WO 98/12179, WO 99/67209), for preparing the radicals (G¹¹) is known (cf., for example, the reaction of 4-nitro-1H-imidazole with methyl chloromethoximino acetate and the subsequent ester hydrolysis in G. Elitropi et al. J. het. Chem. (1979), 16, 1545-1550).

For preparing the radicals G¹³, compounds of the formula (G-X) in which, for example, X, Y=S and $R^{11}$=Me can, after deprotonation at the carbon atom, be reacted with carbon dioxide (E. Capito et al., Tetrahedron: Asymmetry (2003), 16, 3232-3240). Alternatively, the radicals G¹³ in which, for example, X, Y=O and $R^{11}$=Me can also be formed from suitable alpha-ketocarboxylic acids (G-XI) and dialcohols (cf. D. J. Wardrop et al., Org. Lett. (2001), 3, 2261-2264; D. J. Wardrop et al., Tetrahedron: Asymmetry (2003), 14, 929-940).

To prepare the radicals (G¹⁴a,b), it is possible, for example, to react suitable alpha-methylenecarboxylic esters (G-XII), such as methyl methacrylate ($R^6$=Me), with amino compounds according to an aza-Michael addition, to give compounds of the formula (G-XIII) (cf. B. C. Ranu et al., Tetrahedron Lett. (2006), 48, 141-143; K. R. Reddy et al., Synlett (2006), 2246-2250) or 2-formylcarboxylic esters of the formula (G-XIV), for example methyl 2-formyl-2-methylpropionate ($R^6$,$R^7$=Me; US 2005/239838) can be converted by reductive amination into compounds of the formula (G-XV). The ester group is then hydrolysed according to a procedure known from the literature.

According to scheme IV, substituted 1H-1,2,4-triazole-3-acetic esters can also be prepared, for example, from corresponding substituted esters of (triphenylphosphoranylidene) alkanoic acids in the presence of alkylisocyanato carbonates and aryl hydrazines (Capuano et al., Liebigs Annalen der Chemie (1985), 12, 2305-2312).

Reaction scheme IV

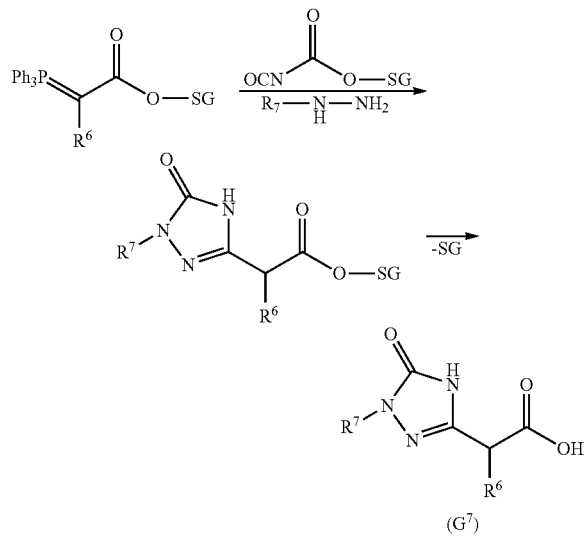

O—SG: protective group, such as OMe, O-tert-Bu, O-benzyl etc.

Other carboxylic acids of the formula (V) which can be used as starting materials if B represents optionally substituted amino are natural or synthetic amino acids. If chiral, these can be present in the (S)- or (R)-form (or L- or D-form).

By way of example, the following natural or synthetic amino acids may be mentioned: Aad, Abu, j-abu, Abz, 2Abz, ε-aca, Acp, Adpd, Ahb, Aib, β-aib, Ala, β-ala, Δ-ala, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, hLeu, hLys, hMet, hPhe, Pro, hSer, hThr, hTrp, hTyr, HyI, Hyp, 3Hyp, Ile, Ise, Iva, Kyn, Lant, Lcn, Leu, Lsg, Lys, β-Lys, Δ-Lys, Met, Mim, MM, nArg, Nle, Nva, Oly, Orn, Pan, Pec, Pen, Phe, Phg, Pic, Pro, Δ-Pro, Pse, Pya, Pyr, Pza, Qin, Ros, Sar, Sec, Sem, Ser, Thi, β-Thi, Thr, Thy, Thx, Tia, Tle, Tly, Trp, Trta, Tyr, Val, Nal, Tbg, Npg, Chg, Thia (cf., for example, Houben-Weyl, Methoden der Organischen Chemie [Methods of organic chemistry], Volume XV/1 and 2, Stuttgart, 1974).

Some of the natural or synthetic amino acids are commercially available, or they can be obtained by methods known from the literature (cf., for example, N-methylamino acids: R. Bowmann et al., J. Chem. Soc. (1950), p. 1346; J. R. McDermott et al., Can. J. Chem. (1973) 51, p. 1915; H. Wurziger et al., Kontakte (Merck, Darmstadt) (1987) 3, p. 8).

In general, it is advantageous to carry out the preparation process according to the invention in the presence of diluents.

Diluents are advantageously employed in such an amount that the reaction mixture is readily stirrable during the entire process. Suitable diluents are known to the person skilled in the art. Suitable diluents for carrying out the process according to the invention are in particular inert organic solvents, on their own or as mixtures.

Examples which may be mentioned are: halogenated hydrocarbons, in particular chlorinated hydrocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisol, phenetol, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methylmorpholine, pyridine and tetramethylenediamine; nitrated hydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and technical-grade hydrocarbons, for example white spirits with components having boiling points in the range of, for example, from 40° C. to 250° C., cymene, petroleum fractions within a boiling point interval of from 70° C. to 190° C., cyclohexane, methylcyclohexane, petrol ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octyl-caprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

Preferred diluents for carrying out the second reaction step of the preparation process according to the invention are methanol, ethanol, isopropanol or butanol, in particular methanol.

Preferred diluents for carrying out the third reaction step of the preparation process according to the invention are halogenated hydrocarbons, in particular chlorinated hydrocarbons, such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene or trichlorobenzene, particularly preferably dichloropropane, methylene chloride, dichlorobutane or chloroform.

Suitable basic reaction auxiliaries for use in the preparation process according to the invention are all suitable acid binders, such as, for example, amines, in particular tertiary amines, and also alkali metal and alkaline earth metal compounds.

Examples which may be mentioned are the hydroxides, hydrides, oxides and carbonates of lithium, sodium, potassium, magnesium, calcium and/or barium, furthermore further basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo-[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidino-pyridine, 4-dimethylaminopyridine, quinoline, α-picoline, β-picoline, isoquinoline, pyrimidine, acridine, N,N,N',N'-tetramethylenediamine, N,N',N'-tetraethylenediamine, quinoxaline, N-propyl-diisopropylamine, N-ethyldiisopropylamine, N,N'-dimethylcyclohexylamine, 2,6-lutidine, 2,4-lutidine or triethyldiamine.

Preference is given to using tertiary amines, such as triethylamine, trimethylamine, triisopropylamine, tributylamine, tricyclohexylamine, N,N-dimethyl-p-aminopyridine, N-methylpyrrolidine, N-methylpiperidine or N-methylimidazole, and particular preference is given to using triethylamine and N,N-dimethyl-p-aminopyridine.

The reaction according to the invention of compounds of the formula (IV) is carried out by reacting, in the third reaction step, the compounds of the formula (IV), which are protected in the 5-position, in the presence of a basic reaction auxiliary, for example triethylamine or N,N-dimethyl-p-aminopyridine, in one of the stated diluents with an activated carboxylic acid as compound of the formula (V), if appropriate in the presence of a coupling agent.

Suitable coupling agents for carrying out the preparation process are all coupling agents suitable for forming an ester or amide bond (cf., for example, Houben-Weyl, Methoden der Organischen Chemie, Volume 15/2; Bodansky et al., Peptide Synthesis 2nd ed. (Wiley & Sons, New York 1976) or Gross, Meienhofer, The Peptides: Analysis, Synthesis, Biology (Academic Press, New York 1979). Preference is given to using the following methods: activated ester method using pentachlorophenol (Pcp) or pentafluorophenol (Pfp), N-hydroxysuccinimide (HOSu), N-hydroxy-5-norbornene-2,3-dicarboxamide (HONB), 1-hydroxylbenzotriazole (HOBt) or 3-hydroxy-4-oxo-3,4-dihydro-1,2,3-benzotriazine as alcohol component, coupling with carbodiimides, such as dicyclohexyl-carbodiimide (DCCI), by the DCC additive process, or with n-propanephosphonic anhydride (PPA) and the mixed anhydride method with pivaloyl chloride, ethyl chloroformate (EEDQ) or isobutyl chloroformate) (IIDQ) or coupling with phosphonium reagents, such as benzotriazol-1-yl-oxytris(dimethylamino-phosphonium)hexafluorophosphate (BOP), bis(2-oxo-3-oxazolidinyl)-phosphonic chloride (BOP-Cl), benzotriazol-1-yltrispyrrolidinophosphonium hexafluorophosphate, (PyBOP®), bromotrispyrrolidinophosphonium hexafluorophosphate (PyBroP®), or with phosphonic acid reagents, such as diethyl cyanophosphonate (DEPC) and diphenylphosphoryl azide (DPPA), uronium reagents, such as 2-(1H-benzotriazol-1-yl)-1,1,3,3-tetramethyluronium tetrafluoroborate (TNTU), 2-(2-oxo-1(2H)-pyridyl)-1,1,3,3-bispentamethylenetetramethyluronium tetrafluoroborate (TOPPipU), O—(N-succinimidyl-1,1,3,3-tetramethyluronium tetrafluoroborate (TSTU), or such as 2-(1H-benzotriazol-1-yl)-1,1,3,3-tetramethyluronium hexafluorophosphate (HBTU), or reagents of the onium type, such as, for example, 1-ethyl-2-fluoropyridinium tetrafluoroborate (FEP).

A preferred activating agent for the carboxylic acids which can be used according to the invention is, for example, N-(3-dimethylaminopropyl)-N'-ethylcarbodiimide Depending on the reaction step, the reaction time in the preparation process according to the invention may be from 5 minutes to 48 hours. In the preparation process according to the invention, the respective reactions are carried out at temperatures between −100° C. and +200° C., preferably between −50° C. and 150° C., particularly preferably at room temperature. In principle, the reaction steps according to the invention of the preparation process can be carried out at atmospheric pressure, preferably at pressures of up to 15 bar and, if appropriate, under an atmosphere of protective gas (for example nitrogen, helium or argon).

For carrying out the third reaction step, from 0.5 to 4.0 mol, preferably from 0.7 to 3.0 mol, particularly preferably from 2.0 to 3.0 mol, of compound of the formula (V), such as, for example, an activated carboxylic acid, are employed per mole of the compound of the formula (IV).

After the reaction has ended, the entire reaction mixture is concentrated. The products of the formula (VI) obtained after work-up can be purified in a customary manner, for example by recrystallization, distillation under reduced pressure or column chromatography, or else they can be reacted further without purification.

The fourth reaction step of the preparation process according to the invention is preferably carried out in the presence of benzenesulphonic acid or para-toluenesulphonic acid. The practice in the presence of para-toluenesulphonic acid is particularly preferred.

For carrying out the fourth reaction step of the preparation process according to the invention, in general from 0.1 to 4.0 mol, preferably from 0.1 to 1.0 mol, particularly preferably from 0.1 to 1.0 mol, of para-toluenesulphonic acid are employed per mole of the compound of the formula (VI).

After the reaction has ended, the entire reaction mixture is concentrated. The products of the formula (I) obtained after work-up can be purified in a customary manner, for example by recrystallization, distillation under reduced pressure or column chromatography, in particular preparative HPLC.

Furthermore, it has been found that the avermectin derivatives of the formula (I) according to the invention in which $R^4$ represents a radical from group ($G^7$) or ($G^8$) in which the grouping B has the meaning mentioned further above and B comprises the grouping H—N either as part of the ring or as part of a substituent, are obtained by reacting compounds of the formula (I) in which $R^4$ represents a radical from group ($G^7$) or ($G^8$) and in which B comprises a nitrogen-containing grouping SG-N either as part of a ring or substituents and where SG represents a suitable protective group, in a fifth reaction step under the reaction conditions of a protective group deblocking, if appropriate in the presence of a diluent and if appropriate in the presence of a suitable acidic or basic reaction auxiliary (reaction scheme V).

Reaction scheme V

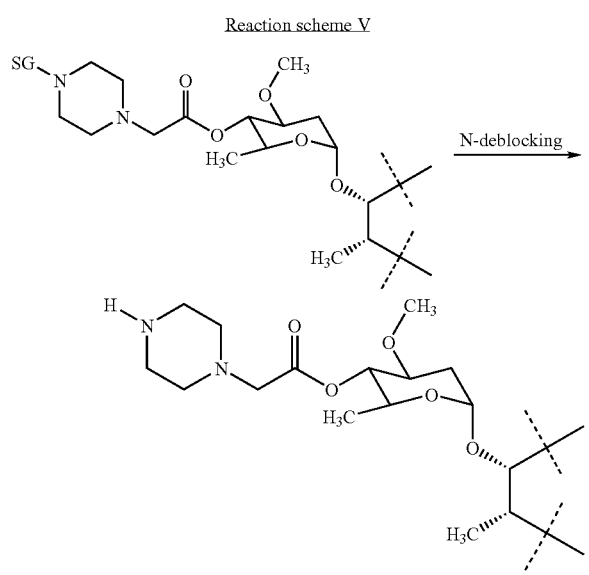

SG = suitable protective group, for example tert-butyloxycarbonyl (BOC)

In this case, for preparing compounds of the formula (I), suitable protective groups for amino groups which may be used are, for example, substituted carbamates, amides, N-alkylamines, N-arylamines, imine derivatives, enamine derivatives, N-sulphenyl derivatives, N-sulphonyl derivatives or N-diaryl-phosphinyl derivatives (cf. Greene T. W., Wuts P. G. W. in Protective Groups in Organic Synthesis; John Wiley & Sons, Inc. 1999, "Protection for the Amino Group").

Preference is given to using protective groups of the carbamate type.

For deblocking protective groups, suitable acidic or basic reaction auxiliaries may be used in a procedure known from the literature. When protective groups of the carbamate type are used for amino groups, preference is given to using acidic reaction auxiliaries. When the t-butylcarbamate (BOC) protective group is employed, use is made, for example, of mixtures of mineral acids, such as hydrochloric acid, hydrobromic acid, nitric acid, sulphur acid, phosphoric acid, or organic acids, such as benzoic acid, formic acid, acetic acid, trifluoroacetic acid, methanesulphonic acid, benzenesulphonic acid or toluenesulphonic acid and a suitable diluent, such as water and/or an organic solvent, such as tetrahydrofuran, dioxane, dichloromethane, chloroform, ethyl acetate, ethanol or methanol. Preference is given to mixtures of hydrochloric acid or acetic acid with water and/or an organic solvent, such as ethyl acetate.

The avermectin derivatives according to the invention can be present in different polymorphic forms or as a mixture of different polymorphic forms. Both the pure polymorphs and the polymorph mixtures are provided by the invention and can be used according to the invention.

The avermectin derivatives according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp.,

*Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., Loa Loa, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aoni-diella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the avermectin derivatives according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:
Inhibitors of Nucleic Acid Synthesis
   benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid
Inhibitors of Mitosis and Cell Division
   benomyl, carbendazim, diethofencarb, fuberidazole, pencycuron, thiabendazole, thiophanate-methyl, zoxamide
Inhibitors of Respiratory Chain Complex I
   diflumetorim
Inhibitors of Respiratory Chain Complex II
   boscalid, carboxin, fenfuram, flutolanil, furametpyr, mepronil, oxycarboxin, penthiopyrad, thifluzamide
Inhibitors of Respiratory Chain Complex III
   azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin
Decouplers
   dinocap, fluazinam
Inhibitors of ATP Production
   fentin acetate, fentin chloride, fentin hydroxide, silthiofam
Inhibitors of Amino Acid Biosynthesis and Protein Biosynthesis
   andoprim, blasticidin-S, cyprodinil, kasugamycin, kasugamycin hydrochloride hydrate, mepanipyrim, pyrimethanil
Inhibitors of Signal Transduction
   fenpiclonil, fludioxonil, quinoxyfen
Inhibitors of Lipid and Membrane Synthesis
   chlozolinate, iprodione, procymidone, vinclozolin
   ampropylfos, potassium-ampropylfos, edifenphos, iprobenfos (IBP), isoprothiolane, pyrazophos
   tolclofos-methyl, biphenyl
   iodocarb, propamocarb, propamocarb hydrochloride Inhibitors of Ergosterol Biosynthesis
fenhexamid,
azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
aldimorph, dodemorph, dodemorph acetate, fenpropimorph, tridemorph, fenpropidin, spiroxamine,
naftifine, pyributicarb, terbinafine Inhibitors of Cell Wall Synthesis
benthiavalicarb, bialaphos, dimethomorph, flumorph, iprovalicarb, polyoxins, polyoxorim, validamycin A Inhibitors of Melanin Biosynthesis
carpropamid, diclocymet, fenoxanil, phthalide, pyroquilon, tricyclazole Resistance Inductors
acibenzolar-S-methyl, probenazole, tiadinil Multisite
captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzene-sulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy) phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl) [1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)-imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl]-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methyl-acetamide Bactericides:
Bronopol, dichlorophen, nitrapyrin, nickel dimethyl dithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-dependent Sodium Channel Blockers
  pyrethroids,
    for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin OR isomer), tralomethrin, transfluthrin, ZXI 8901, pyrethrins (pyrethrum)
  DDT
  oxadiazines,
    for example indoxacarb
  semicarbazones,
    for example metaflumizone (BAS3201)

Acetylcholine Receptor Agonists/Antagonists
  chloronicotinyls,
    for example acetamiprid, clothianidin, dinotefuran, imidacloprid, nitenpyram, nithiazine, thiacloprid, thiamethoxam, AKD-1022, imidaclotiz
  nicotine, bensultap, cartap Acetylcholine Receptor Modulators
  spinosyns,
    for example spinosad and spinetoram GABA-controlled Chloride Channel Antagonists
  organochlorines,
    for example camphechlor, chlordane, endosulfan, gamma-HCH, HCH, heptachlor, lindane, methoxychlor
  fiproles,
    for example acetoprole, ethiprole, fipronil, pyrafluprole, pyriprole, vaniliprole Chloride Channel Activators
  mectins,
    for example abamectin, emamectin, emamectin-benzoate, ivermectin, lepimectin, milbemycin, latidectin, selamectin, doramectin, eprinomectin, moxidectin Latrophilin Receptor Agonists
  depsipeptides, such as, for example, cycl. depsipeptide, for example, emodepside Juvenile Hormone Mimetics,
    for example diofenolan, epofenonane, fenoxycarb, hydroprene, kinoprene, methoprene, pyriproxifen, triprene Ecdysone Agonists/Disruptors
  diacylhydrazines,
    for example chromafenozide, halofenozide, methoxyfenozide, tebufenozide Chitin Biosynthesis Inhibitors
  benzoylureas,
    for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  buprofezin
  cyromazine Oxidative Phosphorylation Inhibitors, ATP Disruptors
  diafenthiuron
  organotin compounds,
    for example azocyclotin, cyhexatin, fenbutatin-oxide Oxidative Phosphorylation Decouplers Acting by Interrupting the H-proton Gradient
  pyrroles,
    for example chlorfenapyr
  dinitrophenols,
    for example binapacryl, dinobuton, dinocap, DNOC Site-I Electron Transport Inhibitors
  METIs,
    for example fenazaquin, fenpyroximate, pyrimidifen, pyridaben, tebufenpyrad, tolfenpyrad hydramethylnon
  dicofol Site-II Electron Transport Inhibitors
  rotenone Site-III Electron Transport Inhibitors
  acequinocyl, fluacrypyrim Microbial Disruptors of the Insect Gut Membrane
  *Bacillus thuringiensis* strains Lipid Synthesis Inhibitors
  tetronic acids,
    for example spirodiclofen, spiromesifen
  tetramic acids,
    for example spirotetramat, cis-3-(2,5-dimethylphenyl)-4-hydroxy-8-methoxy-1-azaspiro-[4.5]dec-3-en-2-one
  carboxamides,
    for example flonicamid
  octopaminergic agonists,
    for example amitraz Inhibitors of Magnesium-stimulated ATPase,
  propargite
  nereistoxin analogues,
    for example thiocyclam hydrogen oxalate, thiosultap-sodium Ryanodin receptor agonists
  benzoic acid dicarboxamides,
    for example flubendiamid
  anthranilamides,
    for example rynaxypyr (3-bromo-N-{4-chloro-2-methyl-6-[(methylamino)carbonyl]phenyl}-1-(3-chloropyridin-2-yl)-1H-pyrazole-5-carboxamide)

Biologicals, Hormones or Pheromones
  azadirachtin, *Bacillus* spec., *Beauveria* spec., codlemone, *Metarrhizium* spec., *Paecilomyces* spec., thuringiensin, *Verticillium* spec.

Active Compounds with Unknown or Unspecific Mechanisms of Action
  fumigants,
    for example aluminium phosphide, methyl bromide, sulphuryl fluoride
  antifeedants,
    for example cryolite, flonicamid, pymetrozine
  mite growth inhibitors,
    for example clofentezine, etoxazole, hexythiazox
  amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize) Herbicide-resistant plants (plants bred in a conventional manner for herbicide tolerance) which may be mentioned include the varieties sold under the name Clearfield® (for example maize) Of course, these statements also apply to plant cultivars having these genetic traits or genetic traits still to be developed, which plant cultivars will be developed and/or marketed in the future.

The plants listed can be treated according to the invention in a particularly advantageous manner with the avermectin derivatives and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored-product pests, but also in the veterinary medicine sector. They are particularly effective against animal parasites (ecto- and endoparasites), such as hard ticks, soft ticks, mange mites, leaf mites, flies (biting and licking), parasitic fly larvae, lice, hair lice, feather lice and fleas.

These animal parasites include:

From the order of the Anoplurida, for example, *Haematopinus* spp., *Linognathus* spp., *Pediculus* spp., *Phtirus* spp. or *Solenopotes* spp. In particular *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus puto* or *Solenopotes capillatus.*

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. or *Felicola* spp. In particular *Bovicola bovis, Bovicola ovis, Bovicola limbata, Damalina bovis, Trichodectes canis, Felicola subrostratus, Bovicola caprae, Lepikentron ovis* or *Werneckiella equi.*

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp. *Rhinoestrus* spp., or *Tipula* spp. In particular *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderrma bovis, Hypoderrma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca.*

From the order of the Siphonapterida, for example, *Pulex* spp., *Ctenocephalides* spp., *Tunga* spp., *Xenopsylla* spp. or *Ceratophyllus* spp. In particular *Ctenocephalides canis, Ctenocephalides felis, Pulex irritans, Tunga penetrans* or *Xenopsylla cheopis.*

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp. or *Supella longipalpa.*

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Rhipicephalus* (Boophilus) spp., *Dermacentor* spp., *Haemophysalis* spp., *Hyalomma* spp., *Rhipicephalus* spp., *Dermanyssus* spp., *Ornithonyssus* spp., *Pneumonyssus* spp., *Raillietia* spp., *Sternostoma* spp., *Varroa* spp. or *Acarapis* spp. In particular *Argas persicus, Argas reflexus, Ornithodorus moubata, Otobius megnini, Rhipicephalus* (Boophilus) *microplus, Rhipicephalus* (Boophilus) *decoloratus, Rhipicephalus* (Boophilus) *annulatus, Rhipicephalus* (Boophilus) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicandus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum* or *Varroa jacobsoni.*

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., or *Laminosioptes* spp. In particular *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic Mange, Pneumonyssoides caninum* or *Acarapis woodi.*

The avermectin derivatives according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis*, *Ctenocephalides felis*, *Pulex irritans*, *Tunga penetrans*, *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example, *Pediculus humanus capitis*, *Pediculus humanus corporis*, *Pemphigus* spp., *Phylloera vastatrix*, *Phthirus pubis*.

From the order of the Heteroptera, for example, *Cimex hemipterus*, *Cimex lectularius*, *Rhodinus prolixus*, *Triatoma infestans*.

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

Treatment according to the invention of the plants and plant parts with the active compound combinations is carried out directly or by allowing the compounds to act on their surroundings, habitat or storage space by the customary treatment methods, for example by immersion, spraying, evaporation, fogging, scattering, painting on and, in the case of propagation material, in particular in the case of seed, also by applying one or more coats.

The mixtures according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resulting plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the insecticidal individual active compound, which exceeds the activity to be expected of the two active compounds when applied individually. Also advantageous is the synergistically increased fungicidal activity of the compositions according to the invention in comparison with the fungicidal individual active compound, which exceeds the activity to be expected of the active compound when applied individually. This makes possible an optimization of the amount of active compounds employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus*, *Rhizobium*, *Pseudomonas*, *Serratia*, *Trichoderma*, *Clavibacter*, *Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

PREPARATION EXAMPLES

Avermectin $B_1$ monosaccharide (III-1) (—$C_{22}R^1$-A-$C_{23}R^2$— : —HC=CH—)

A solution of 13.52 g of abamectin (II-1) in 170 ml of 2-propanol and 1.7 ml of conc. sulphuric acid is stirred at room temperature for 20 hours. After addition of saturated sodium bicarbonate solution, the mixture is extracted with dichloromethane, the organic phase is dried over sodium sulphate and the solvent is removed under reduced pressure. The residue is purified on silica gel (silica gel 60—Merck, particle size: 0.04 to 0.063 mm) using cyclohexane/ethyl acetate (5:2). This gives 6.83 g of avermectin $B_1$ monosaccharide (III-1) as a colourless solid.

5-O-tert-Butyldimethylsilyl-avermectin $B_1$ monosaccharide (IV-1) (—$C_{22}R^1$-A-$C_{23}R^2$— : —HC=CH—)

4.1 g of imidazole and 2.2 g of tert-butyldimethylsilyl chloride are added to a solution of 6.8 g of avermectin $B_1$ monosaccharide (III-1) in 31 ml of N,N-dimethylformamide, and the mixture is stirred at room temperature for 2 hours. After addition of cyclohexane and ethyl acetate (1:1), the mixture is washed with water and saturated sodium chloride solution, the organic phase is dried over sodium sulphate and the solvent is removed under reduced pressure. The residue is purified on silica gel (silica gel 60—Merck, particle size: 0.04 to 0.063 mm) using cyclohexane/ethyl acetate (4:1). This gives 4.4 g of 5-O-tert-butyldimethylsilyl-avermectin $B_1$ monosaccharide (IV-1) as a colourless solid.

5-O-tert-Butyldimethylsilyl-4'-O-(cyclopropylcarbonyl)-avermectin $B_1$ monosaccharide (VI-1) (—$C_{22}R^1$-A-$C_{23}R^2$— : —HC=CH—)

150 mg of 5-O-tert-butyldimethylsilyl-avermectin $B_1$ monosaccharide (IV-1) are dissolved in 15 ml of dichloromethane. Under argon, 102 mg of N-(3-dimethylaminopropyl)-N'-ethylcarbodiimide, 65 mg of 4-dimethylaminopyridine (DMAP), 46 mg of cyclopropanecarboxylic acid and a little molecular sieve are added, and the mixture is stirred at room temperature for 2 hours. After addition of saturated sodium bicarbonate solution, the mixture is extracted with dichloromethane, the organic phase is dried over sodium sulphate and the solvent is removed under reduced pressure. The residue is filtered through silica gel (silica gel 60—Merck, particle size: 0.04 to 0.063 mm) using cyclohexane/ethyl:acetate (4:1). This gives 150 mg of 5-O-tert-butyldimethylsilyl-4'-O-(cyclopropylcarbonyl)-avermectin $B_1$ monosaccharide (VI-1).

LC-MS: 933.6 (M+Na, 80%) $C_{51}H_{78}O_{12}Si$ (911.251)
Retention time: 20.5 min (22 min)
Method A:

Example 1

4'-O-(cyclopropylcarbonyl)-avermectin $B_1$ monosaccharide (—$C_{22}R^1$-A-$C_{23}R^2$— : —HC=CH—)

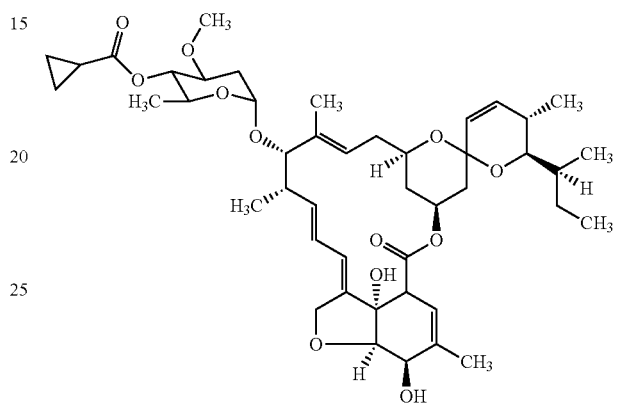

6 mg of 4-toluenesulphonic acid are added to a solution of 150 mg of 5-O-tert-butyldimethylsilyl-4'-O-(cyclopropylcarbonyl)-avermectin $B_1$ monosaccharide (VI-1) in absolute methanol, and the mixture is stirred at room temperature for 4 hours. After addition of saturated sodium bicarbonate solution, the mixture is extracted with ethyl acetate, the organic phase is dried over sodium sulphate and the solvent is removed under reduced pressure. The residue is purified by preparative HPLC (Waters 2996 photodiode array detector, 245 nm, x Terra Prep MS C18 column 5 μm 19×100 mm, flow 20 ml/min water/acetonitrile). This gives 47 mg of 4'-O-(cyclopropylcarbonyl)-avermectin $B_1$ monosaccharide.

LC-MS: 797.6 (M+H, 60%) $C_{45}H_{64}O_{12}$, MW: 796.989
Retention time: 15.70 min (22 min)
$^1$H-NMR (600 MHz, CDCl$_3$): δ (ppm)=0.85-0.96 (m, 11H), 1.05 (m, sym, 2H), 1.13 (d, J=6.3, 3H), 1.17 (d, J=7.0, 3H), 1.45-1.71 (m, 10H), 1.78 (m, sym, 1H), 1.88 (s, 3H), 2.02 (ddd, J=12.1, 4.8, 1.6, 1H), 2.21-2-38 (m, 5H), 2.54 (m, sym., 1H), 3.30 (q, J=2.2, 1H), 3.45 (s, 3H), 3.49 (dd, J=11.4, 1.5, 1H), 3.68 (m, sym, 1H), 3.88 (m, sym, 1H), 3.92-3.96 (m, 2H), 3.98 (d, J=6.3, 1H), 4.06 (s, 1H), 4.30 (s, broad, 1H), 4.65-4.73 (m, 3H), 4.82 (d, J=3.4, 1H), 4.99 (d, J=8.8, 1H), 5.38-5.44 (m, 2H), 5.55 (dd, J=9.9, 2.6, 1H), 5.73-5.79 (m, 3H), 5.88 (m, sym, 1H).
$^{13}$C-NMR (150 MHz, CDCl$_3$): δ (ppm)=8.41, 8.54, 12.03, 12.93, 12.96, 15.11, 16.36, 17.38, 19.98, 20.20, 27.49, 30.55, 34.23, 34.85, 35.11, 36.61, 39.70, 40.42, 45.66, 57.32, 66.57, 67.68, 68.29, 68.32, 68.45, 74.89, 75.81, 76.14, 79.00, 80.35, 81.95, 94.94, 95.73, 118.00, 118.33, 120.35, 124.80, 127.67, 134.99, 136.34, 137.88, 137.96, 139.69, 173.76, 174.29.

The avermectin derivatives of the formula (I) (where $R^5$=H) listed in the table below (Table 2) can be prepared analogously.

TABLE 2

| Ex. No. | —C$_{22}$R$^1$—A—C$_{23}$R$^2$— | R$^3$ | R$^4$ | Physical data$^a)$ |
|---|---|---|---|---|
| 2 | —HC=CH— | sec-Butyl | phenyl | 7.47 (t, J = 7.5, 2H), 7.59 (t, J = 7.4, 1H), 8.10 (d, J = 7.1, 2H); m/z = 833.6 (M + H, 80); R$_t$ = 16.75 (22) |
| 3 | —HC=CH— | sec-Bu | 1-ethyl-1,2,3-triazole | 5.27 (d, J = 5.0, 2H), 7.77 (d, J = 7.9, 2H); m/z = 838.6 (M + H, 70); R$_t$ = 13.86 (22) |
| 4 | —HC=CH— | sec-Bu | sec-butylmethyl (H$_3$C-CH(CH$_3$)-CH$_2$CH$_2$-) | 0.99 (dd, J = 6.6, 1.3 6H), 2.10-2.21 (m, 1H), 2.23-2.36 (m, 7H); m/z = 813.6 (M + H, 100); R$_t$ = 16.89 (22) |
| 5 | —HC=CH— | sec-Bu | neopentyl ((CH$_3$)$_3$C-CH$_2$-) | 1.24 (s, 9H); m/z = 813.6 (M + H, 80); R$_t$ = 16.80 (22) |
| 6 | —HC=CH— | sec-Bu | n-propyl | 1.12-1.21 (m, 9H), 2.21-2.43 (m, 7H); m/z = 785.6 (M + H, 100); R$_t$ = 15.61 (22) |
| 7 | —HC=CH— | sec-Bu | 2,2-dimethylbutyl | 1.07 (s, 9H), 2.22-2.36 (m, 7H); m/z = 827.6 (M + H, 70); R$_t$ = 17.46 (22) |
| 8 | —HC=CH— | sec-Bu | 3-methylpentyl / isohexyl | 0.90-0.97 (m, 15H), 2.20-2.36 (m, 6H); m/z = 827.6 (M + H, 50), 849.6 (M + Na, 20); R$_t$ = 17.45 (22) |
| 9 | —HC=CH— | sec-Bu | isobutyl (H$_3$C)$_2$CH-CH$_2$- | 0.89-0.98 (m, 12H), 1.10-1.20 (m, 9H), 2.36-2.48 (m, 1H); m/z = 813.6 (M + H, 80); R$_t$ = 16.84 (22) |
| 10 | —HC=CH— | sec-Bu | H$_3$C-O-CH$_2$CH$_2$-O-CH$_2$- | 3.40 (s, 3H), 3.60-3.62 (m, 2H), 3.74-3.77 (m, 2H), 4.22 (d, J = 0.7, 2H); m/z = 867 (M + Na, 40); R$_t$ = 14.89 (22) |
| 11 | —HC=CH— | sec-Bu | F$_3$C-CH$_2$- | 3.25 (q, J = 10.1, 2H); m/z = 839.5 (M + H, 50); R$_t$ = 15.99 (22) |
| 12 | —HC=CH— | sec-Bu | 3-thienylmethyl | 3.71 (s, 2H), 7.07 (dd, J = 5.0, 1.2, 1H), 7.19-7.20 (m, 1H), 7.26-7.30 (m, 1H); m/z = 853.5 (M + H, 70), 870.5 (M + NH4, 100); R$_t$ = 16.26 (22) |
| 13 | —HC=CH— | sec-Bu | 2-thienylmethyl | 3.89 (s, 2H), 6.93,6.99 (m, 2H), 7.22 (dd, J = 5.0, 1.3, 1H); m/z = 853 (M + H, 80); R$_t$ = 16.26 (22) |
| 14 | —HC=CH— | sec-Bu | (4-methyl-1,3-dioxan-4-yl)methyl | 1.20 (s, 3H), 3.56-3.62 (m, 2H), 4.30-4.33 (m, 2H), 4.75-4.77 (m, 1H), 4.89 (d, J = 6.3, 1H); m/z = 879.6 (M + Na, 50); R$_t$ = 15.39 (27) |
| 15 | —HC=CH— | sec-Bu | (1-methylcyclopropyl)methyl | 0.69-0.73 (m, 2H), 1.25-1.29 (m, 2H), 1.3 (s, 3H); m/z = 811.6 (M + H, 40); R$_t$ = 16.51 (27) |

TABLE 2-continued

| Ex. No. | —C22R1—A—C23R2— | R3 | R4 | Physical data*a*) |
|---|---|---|---|---|
| 16 | —HC=CH— | sec-Bu | 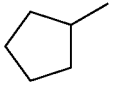 | 2.79 (q, J = 8, 1H); m/z = 825.6 (M + H, 40); R*t* = 17.25 (27) |
| 17 | —H2C—CH2— | sec-Bu | 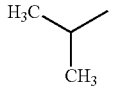 | 1.20 (d, J = 7.0, 3H), 1.21 (d, J = 7.0, 3H), 2.60 (q, J = 7.0, 1H); m/z = 824.6 (M + Na, 20); R*t* = 18.07 (27) |
| 18 | —H2C—CH2— | sec-Bu |  | 5.27 (d, J = 5.3, 2H), 7.77 (dd, J = 8.3, 1.1 2H); m/z = 840.6 (M + H, 70); R*t* = 15.82 (27) |
| 19 | —HC=CH— | sec-Bu | 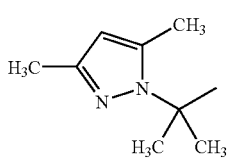 | 1.83, 1.87, 2.22, 2.25 (s, je 3H), 5.86 (s, 1H); m/z = 893.7 (M + H, 100); R*t* = 16.70 (27) |
| 20 | —HC=CH— | sec-Bu | 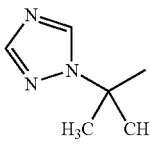 | 1.92 (s, 3H), 1.93 (s, 3H), 7.96 (s, 1H), 8.27 (s, 1H); m/z = 866.6 (M + H, 100); R*t* = 14.76 (27) |
| 21 | —H2C—CH2— | sec-Bu | 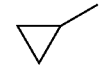 | 1.03-1.05 (m, 2H); m/z = 801 (M + H, 70); R*t* = 17.59 (27) |
| 22 | —H2C—CH2— | sec-Bu | 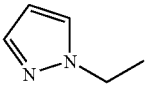 | 4.99 (d, J = 2.3, 2H), 6.34 (t, J = 2.1, 1H), 7.52 (d, J = 2.3, 1H), 7.56 (d, J = 1.6, 1H); m/z = 840 (M + H, 10); R*t* = 16.41 (22) |
| 23 | —H2C—CH2— | sec-Bu | 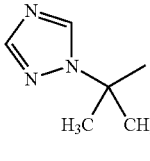 | 1.92 (s, 3H), 1.93 (s, 3H), 7.96 (s, 1H), 8.28 (s, 1H); m/z = 868.7 (M + H, 100); R*t* 16.56 (22) |
| 24 | —H2C—CH2— | sec-Bu | 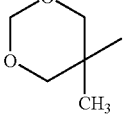 | 1.20 (s, 3H), 3.56-3.62 (m, 2H), 4.30-4.33 (m, 2H), 4.74-4.77 (m, 1H), 4.89 (d, J = 6.0, 1H); m/z = 882.8 (M + Na, 80); R*t* = 17.11 (22) |
| 25 | —HC=CH— | sec-Bu | 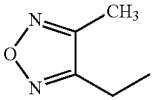 | 2.41 (s, 3H), 3.90 (d, J = 1.1, 2H); m/z = 853.7 (M + H, 100); R*t* = 15.98 (27) |
| 26 | —HC=CH— | sec-Bu | 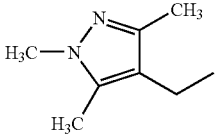 | 2.20 (s, 3H), 2.20 (s, 3H), 3.33 (s, 2H), 3.70 (s, 3H); m/z = 879.9 (M + H, 100); R*t* = 14.48 (27) |
| 27 | —HC=CH— | sec-Bu | 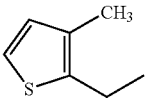 | 2.21 (d, J = 1.1, 3H), 3.78 (d, J = 1.1, 2H), 6.82 (dd, J = 5.1, 0.8, 1H), 7.11 (dd, J = 5.1, 0.9, 1H); m/z = 867.8 (M + H, 60); R*t* = 16.90 (27) |
| 28 | —HC=CH— | sec-Bu | 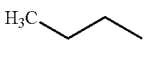 | 0.98 (t, J = 7.4, 3H), 2.21-2.37 (m, 7H); m/z = 799.6 (M + H, 100); R*t* = 16.27 (22) |

TABLE 2-continued

| Ex. No. | —C22R1—A—C23R2— | R3 | R4 | Physical data[a] |
|---|---|---|---|---|
| 29 | —HC=CH— | sec-Bu | 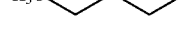 | 0.89-0.96 (m, 12H), 1.39 (sxt., J = 7.6, 2H), 2.22-2.39 (m, 7H); m/z = 813.6 (M + H, 70); $R_t$ = 16.89 (22) |
| 30 | —HC=CH— | sec-Bu | 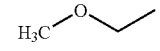 | 3.48 (s, 3H), 4.09 (s, 2H); m/z = 3.48 (s, 3H), 4.09 (s, 2H); $R_t$ = 14.72 (22) |
| 31 | —HC=CH— | sec-Bu | 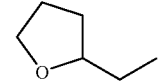 | 1.86-1.98 (m, 6H), 2.06-2.17 (m, 1H), 2.49-2.56 (m, 2H), 2.67 (ddd, J = 21.4, 10.8, 6.7, 1H), 3.75 (q, J = 7.6, 1H), 3.83-3.99 (m, 5H), 4.24-4.32 (m, 2H); m/z = 841 (M + H, 10), 858.6 (M + NH4, 100); $R_t$ = 15.38 (22) |
| 32 | —HC=CH— | sec-Bu | 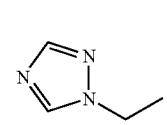 | 5.04 (s, 2H), 7.99 (s, 1H), 8.25 (s, 1H); m/z = 838.5 (M + H, 100); $R_t$ = 13.46 (22) |
| 33 | —HC=CH— | sec-Bu | 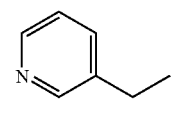 | 3.69 (s, 2H), 7.28 (dd, J = 4.9, 3.0, 1H), 7.69 (dt, J = 7.9, 2.2, 1H), 8.53 (dd, 4.8, 2.0, 1H), 8.45 (d, J = 1.8, 1H); m/z = 848.6 (M + H, 100); $R_t$ = 12.50 (22) |
| 34 | —HC=CH— | sec-Bu | 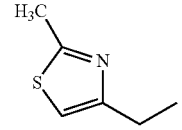 | 3.68 (s, 2H), 6.93-6.99 (m, 1H), 7.04-7.12 (m, 2H), 7.25-7.32 (m, 1H); m/z = 865.5 (M + H, 90); $R_t$ = 16.53 (22) |
| 35 | —HC=CH— | sec-Bu | 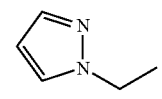 | 4.99 (s, 2H), 6.34 (t, J = 2.2, 1H), 7.52 (d, J = 2.3, 1H), 7.56 (d, J = 1.9); m/z = 837 (M + H, 10); $R_t$ = 14.43 (22) |
| 36 | —HC=CH— | sec-Bu | 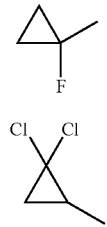 | 0.85-0.90 (m, 2H); m/z = 815.6 (M + H, 50); $R_t$ = 16.05 (27) |
| 37 | —HC=CH— | sec-Bu |  | 1.92 (dd, J = 9.7, 7.3, 1H), 2.13 (t, J = 7.3, 1H), 2.62 (dd, J = 9.6, 7.9, 1H); m/z = 865.5 (M + H, 40); $R_t$ = 16.89 (27) |
| 38 | —HC=CH— | sec-Bu | 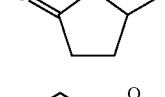 | 2.50-2.58 (m, 2H), 4.27-4.33 (m, 2H); m/z = 862.5 (M + Na, 5); $R_t$ = 13.32 (27) |
| 39 | —HC=CH— | sec-Bu | 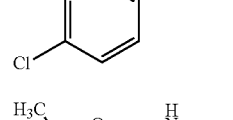 | 4.67-4.70 (m, 5H), 6.87 (d, J = 9.0, 2H), 7.25 (d, J = 8.7, 2H); m/z = 897.6 (M + H, 40); $R_t$ = 17.13 (27) |
| 40 | —HC=CH— | sec-Bu | 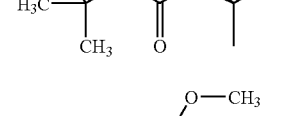 | 1.44 (s, 9H), 1.50 (s, 3H), 4.26-4.35 (m, 1H); m/z = 922.7 (M + H, 20); $R_t$ = 16.36 (27) |
| 41 | —HC=CH— | sec-Bu | 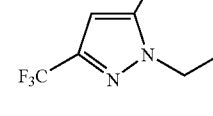 | 3.41 (s, 3H), 4.83 (s, 2H), 5.83 (s, 1H); m/z = 957.6 (M + Na, 20); $R_t$ = 16.36 (27) |
| 42 | —HC=CH— | sec-Bu | 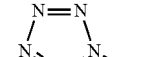 | 5.32 (d, J = 2.8, 2H), 8.86 (s, 1H); m/z = 861.6 (M + Na, 10); $R_t$ = 14.28 (27) |

TABLE 2-continued

| Ex. No. | —C22R1—A—C23R2— | R3 | R4 | Physical data[a] |
|---|---|---|---|---|
| 43 | —HC=CH— | sec-Bu | 4-ethyl-3,5-dimethylisoxazole | 2.25 (s, 3H), 2.37 (s, 3H), 3.34 (s, 2H); m/z = 864 (M − H, 100); R_t = 864 (M − H, 100) |
| 44 | —HC=CH— | sec-Bu | 1-ethyl-2,5-dimethylpyrrole | 2.19 (s, 6H), 4.54 (s, 2H), 5.80 (s, 2H); m/z = 846 (M − 18, 100); R_t = 16.80 (27) |
| 45 | —HC=CH— | sec-Bu | 1-ethyl-2,5-dioxopyrrolidine | 2.81 (s, 4H), 4.24 (d, 1H), 4.38 (d, 1H); m/z = 868 (M + H, 40); R_t = 14.27 (27) |
| 46 | —HC=CH— | sec-Bu | 4-ethyl-2-(pyridin-4-yl)thiazole | 3.93-3.99 (m, 5H), 7.80 (dd, J = 4.6, 1.5, 2H), 8.69 (d, J = 6.0, 2H); m/z = 931.8 (M + H, 100); R_t = 14.39 (27) |
| 47 | —HC=CH— | sec-Bu | 4-ethyl-2,5-dimethylthiazole | 2.37 (s, 3H), 2.60 (s, 3H), 3.75 (s, 2H); m/z = 882 (M + H, 40); R_t = 15.64 (27) |
| 48 | —HC=CH— | sec-Bu | 1-(isopropyl)pyrazole | 1.83 (d, J = 7.1, 3H), 5.18 (q, J = 7.3, 1H), 6.32 (t, J = 2.2, 1H), 7.54 (dd, J = 1.3, 0.5, 1H), 7.59 (d, J = 2.3, 1H); m/z = 851 (M + H, 10); R_t = 15.22 (27) |
| 49 | —HC=CH— | sec-Bu | 1-ethylimidazole | 4.75 (s, 2H), 6.99 (t, J = 1.3, 1H), 7.11 (t, J = 1.0, 1H), 7.54 (s, 1H); m/z = 837 (M + H, 100); R_t = 10.32 (27) |
| 50 | —HC=CH— | sec-Bu | 1-ethylpiperidine | 2.49-2.59 (m, 5H), 3.25 (d, J = 4.6, 2H); m/z = 854.4 (M + H, 100); R_t = 10.51 (27) |
| 51 | —HC=CH— | sec-Bu | tert-butyl (1-ethylpiperidin-4-yl)carbamate | 1.44 (s, 9H), 1.90-1.99 (m, 2H), 2.86-2.97 (m, 2H), 4.40-4.47 (m, 1H); m/z = 969.5 (M + H, 100); R_t = 11.15 (27) |
| 52 | —HC=CH— | sec-Bu | 4-(isopropyl)morpholine | 1.31-1.38 (m, 3H), 2.60-2.71 (m, 4H), 3.26-3.33 (m, 2H), 3.63-3.78 (m, 5H); m/z = 870.4 (M + H, 100); R_t = 11.66 (27) |

TABLE 2-continued

| Ex. No. | —C₂₂R¹—A—C₂₃R²— | R³ | R⁴ | Physical data[a] |
|---|---|---|---|---|
| 53 | —HC=CH— | sec-Bu | tert-butyl 4-ethylpiperazine-1-carboxylate | 1.46 (s, 9H), 2.49-2.60 (m, 5H), 3.28-3.32 (m, 3H), 3.46-3.52 (m, 5H); m/z = 955.6 (M + H, 100); R_t = 14.18 (27) |
| 54 | —HC=CH— | sec-Bu | N-((S)-1-methylethyl)acetamide | 2.02 (s, 3H), 4.60-4.73 (m, 4H), 6.05 and 6.12 (d, d, together 1H); m/z = 842 (M + H, 2); R_t = 13.48 (27) |
| 55 | —HC=CH— | sec-Bu | tert-butyl ethyl(methyl)carbamate | 1.44 (s, 9H), 2.95 (d, J = 4.4, 3H), 4.03-4.04 (m, 2H); m/z = 900 (M + H, 5), 917 (M + 18, 30); R_t = 16.61 (27) |
| 56 | —HC=CH— | sec-Bu | 1-((S)-1-methylethyl)-1H-1,2,3-triazole | 1.87-1.92 (m, 6H), 5.50-5.62 (m, 2H), 7.76 (d, J = 1.1, 1H), 7.77 (d, J = 1.1, 1H); m/z = 852 (M + H, 50); Rt = 14.47 (27) |
| 57 | —HC=CH— | sec-Bu | N,N-dimethylethylamine | 2.38 (s, 6H), 3.24 (d, J = 6.3, 2H); m/z = 814.5 (M + H, 100); Rt = 10.54 (27) |
| 58 | —HC=CH— | sec-Bu | 1-(1-methylethyl)-1H-imidazole | 1.79 (d, J = 7.3, 3H), 4.92 (q, J = 7.3, 1H), 7.06 (s, 1H), 7.10 (s, 1H), 7.61 (s, 1H); m/z = 851.5 (M + H, 100); Rt = 11.01 (27) |
| 59 | —HC=CH— | sec-Bu | 1-ethyl-3-(trifluoromethyl)-1H-pyrazole | 5.02 (s, 2H), 6.61 (d, J = 2.1, 1H), 7.59 (dd, J = 2.4, 0.9, 1H); m/z = 905.4 (M + H, 60); R_t = 16.25 (27) |
| 60 | —HC=CH— | sec-Bu | 5-ethyl-2,4-dimethyl-2,4-dihydro-3H-1,2,4-triazol-3-one | 3.26 (s, 3H), 3.45 (s, 3H), 3.66 (s, 2H); m/z = 864.5 (M − 18, 20), 883 (M + H, 5); R_t = 13.55 (27) |
| 61 | —HC=CH— | sec-Bu | 1-(1-methylethyl)-1H-1,2,3-triazole | 1.87-1.9 (m, 6H), 5.51-5.62 (m, 2H), 7.76-7.77 (m, 2H); m/z = 852.4 (M + H, 100); R_t = 14.43 (27) |
| 62 | —HC=CH— | sec-Bu | 1-((S)-1-methylethyl)-1H-pyrazole | 1.83 (d, J = 10.4, 3H), 5.18 (q, J = 7.3, 1H), 6.32 (dd, J = 2.3, 1.9, 1H), 7.54 (dd, J = 1.8, 0.5, 1H), 7.56 (dd, J = 2.3, 0.4, 1H); m/z = 833.4 (M − 18, 100), 852 (M + H, 5); R_t = 15.17 (27) |
| 63 | —HC=CH— | sec-Bu | 2-ethyl-3,4-dimethyl-2,4-dihydro-3H-1,2,4-triazol-3-one | 2.23 (s, 3H), 3.23 (s, 3H), 4.58 (d, J = 4.1, 2H); m/z = 899 (M + 18, 20); R_t = 13.41 (27) |

TABLE 2-continued

| Ex. No. | —C$_{22}$R$^1$—A—C$_{23}$R$^2$— | R$^3$ | R$^4$ | Physical data$^{a)}$ |
|---|---|---|---|---|
| 64 | —HC=CH— | sec-Bu | 3-methoxy-4-methyl-1-ethyl-1,2,4-triazol-5(4H)-one | 3.14 (s, 3H), 3.96 (s, 3H), 4.52 (s, 2H); m/z = 915 (M + 18, 15); R$_t$ = 13.98 (27) |
| 65 | —HC=CH— | sec-Bu | 2-ethylpyridine | m/z = 830 (M − 18, 100); R$_t$ = 13.91 (27) |
| 66 | —HC=CH— | sec-Bu | 1-methylcyclopent-1-enyl | 1.93-2.05 (m, 3H), 2.50-2.58 (m, 3H), 2.58-2.65 (m, 2H), 6.85 (d, J = 2H, 1H); m/z = 919 (M + H, 20); R$_t$ = 16.76 (27) |
| 67 | —HC=CH— | sec-Bu | 5-ethyl-5-methyl-1,3-dioxane | 0.90-0.98 (m, 15H), 3.60-3.70 (m, 3H), 4.28-4.37 (m, 2H), 4.71-4.80 (m, 2H); m/z = 870 (M + H, 30); R$_t$ = 15.86 (27) |
| 68 | —HC=CH— | sec-Bu | 2-(2-methoxyethyl)-5-methyl-1,3-dioxane | m/z = 915 (M + H, 20); R$_t$ = 16.51 (27) |
| 69 | —HC=CH— | sec-Bu | 2-chloro-5-isopropylpyridine | m/z = 897 (M + H, 50); R$_t$ = 16.52 (27) |
| 70 | —HC=CH— | sec-Bu | 1-cyanocyclopropyl | m/z = 821 (M + H, 60); R$_t$ = 15.70 (27) |
| 71 | —HC=CH— | sec-Bu | 1-methyl-2-ethylpyrrole | 3.60 (s, 3H), 3.67 (s, 2H), 6.04-6.08 (m, 2H), 6.59 (t, J = 2.3, 1H); m/z = 850 (M + H, 20); R$_t$ = 8.74 (12) |
| 72 | —HC=CH— | sec-Bu | 2-cyanopropyl | 1.64 (dd, J = 7.4, 2.6, 3H), 3.61 (quint., J = 7.6, 1H); m/z = 809 (M + H, 80); R$_t$ = 15.49 (27) |
| 73 | —HC=CH— | sec-Bu | 4-(sec-butyl)morpholine | m/z = 884 (M + H, 100); R$_t$ = 9.79 (27) |
| 74 | —HC=CH— | sec-Bu | N,N,1-trimethylcyclopropylamine | 0.96-0.99 (m, 2H), 1.29-1.33 (m, 2H), 2.57 (s, 6H); m/z = 840 (M + H, 100); R$_t$ = 11.68 (27) |
| 75 | —HC=CH— | sec-Bu | 4-ethylmorpholin-3-one | m/z = 853 (M − 18, 30); R$_t$ = 13.60 (27) |

TABLE 2-continued

| Ex. No. | —C22R1—A—C23R2— | R3 | R4 | Physical dataa) |
|---|---|---|---|---|
| 76 | —HC=CH— | sec-Bu | 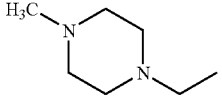 | 2.40 (s, 3H), 2.46-2.80 (m, 13H), 3.27-3.31 (m, 3H); m/z = 867 (M − H, 80); $R_t$ = 10.19 (27) |
| 77 | —HC=CH— | sec-Bu | 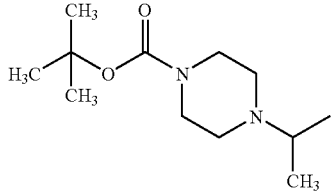 | m/z = 969 (M + H, 100); $R_t$ = 14.63 and 15.05 (27) |
| 78 | —HC=CH— | sec-Bu | 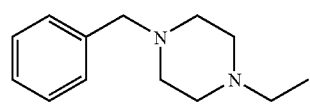 | 2.48-2.69 (m, 8H), 3.27 (d, J = 2.7, 2H), 3.52 (s, 2H), 7.24-7.32 (m, 5H); m/z = 945 (M + H, 100); $R_t$ = 11.33 (27) |
| 79 | —HC=CH— | sec-Bu | 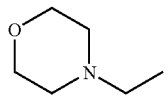 | 2.58-2.67 (m, 4H), 3.27 (d, J = 2.6, 2H), 3.77 (t, J = 4.6, 4H); m/z = 856 (M + H, 100); $R_t$ = 10.83 (27) |
| 80 | —HC=CH— | sec-Bu | 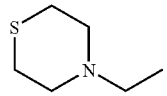 | m/z = 872 (M + H, 100); $R_t$ = 11.96 (27) |
| 81 | —HC=CH— | sec-Bu | 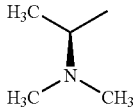 | 1.35 (d, J = 7.0, 3H), 2.38 (s, 6H), 3.66-3.78 (m, 2H); m/z = 828 (M + H, 100); $R_t$ = 10.90 (27) |
| 82 | —HC=CH— | sec-Bu | 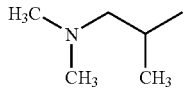 | 1.88 (s, 3H), 2.26 (s, 6H), 3.29-3.32 (m, 2H); m/z = 842 (M + H, 100); $R_t$ = 10.52 (27) |
| 83 | —HC=CH— | sec-Bu | 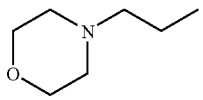 | m/z = 870 (M + H, 100); $R_t$ = 10.88 (27) |
| 84 | —HC=CH— | sec-Bu | 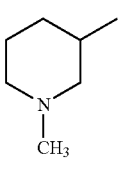 | m/z = 854 (M + H, 100); $R_t$ = 10.79 (27) |
| 85 | —HC=CH— | sec-Bu | 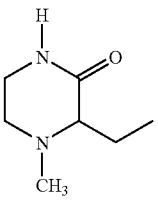 | 2.40 (s, 3H), 2.60-2.66 (m, 1H), 2.89-3.11 (m, 3H), 3.22-3.31 (m, 2H) 3.48 (d, J = 8.5, 1H); m/z = 883 (M + H, 5); $R_t$ = 10.13 (27) |
| 86 | —HC=CH— | sec-Bu | 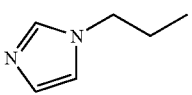 | 2.80-2.88 (m, 2H), 4.27-4.35 (m, 3H), 6.99 (s broad, 1H), 7.07 (s broad, 1H), 7.54 (s broad, 1H); m/z = 852 (M + H, 100); $R_t$ = 10.31 (27) |

TABLE 2-continued

| Ex. No. | —C$_{22}$R$^1$—A—C$_{23}$R$^2$— | R$^3$ | R$^4$ | Physical data$^{a)}$ |
|---|---|---|---|---|
| 87 | —HC═CH— | sec-Bu | (N-propylpiperidine) | 2.49-2.75 (m, 7H), 2.82-2.90 (m, 2H); m/z = 868 (M + H, 100); R$_t$ = 11.03 (27) |
| 88 | —HC═CH— | sec-Bu | (4-methyl-1-propylpiperazine) | 2.21-2.40 (m, 11H), 2.59-2.65 (m, 2H), 2.72-2.80 (m, 2H); m/z = 883.5 (M + H, 100); R$_t$ = 10.22 (27) |
| 89 | —HC═CH— | sec-Bu | (dichlorovinyl dimethyl methylcyclopropane) | 1.22 (s, 3H), 1.29 (s, 3H), 1.68 (d, J = 5.3, 1H), 2.22-2.38 (m, 6H), 5.65 (d, J = 8.1, 1H); m/z = 919.5 (M + H, 80); R$_t$ = 18.49 (22) |
| 90 | —HC═CH— | sec-Bu | (2,4-dichlorophenyl methyl ketone O-methyloxime) | 4.08 (s, 3H), 7.17 (d, J = 8.3, 1H), 7.32 (dd, J = 8.3, 2.0, 1H), 7.46 (d, J = 2.0, 1H); m/z = 958 (M + H, 80); R$_t$ = 17.81 (27) |
| 91 | —HC═CH— | sec-Bu | (2-thienyl-4-methyl-5-ethylthiazole) | 2.43 (s, 3H), 3.81 (s, 2H), 7.04 (dd, J = 5.1, 3.7, 1H), 7.33 (dd, J = 5.1, 1.1, 1H), 7.39 (dd, J = 3.7, 1.1, 1H); m/z = 951 (M + H, 15); R$_t$ = 17.19 (27) |
| 92 | —HC═CH— | sec-Bu | (Boc-protected amine) | 1.46 (s, 9H), 1.88 (s, 3H), 2.85 (s, 3H), 4.62-4.75 (m, 4H); m/z = 931.5 (M + 18, 20); R$_t$ = 17.18 (27) |
| 93 | —HC═CH— | sec-Bu | (3-pyridyl-4-methyl-5-thiazole) | 2.49 (s, 3H), 3.86 (s, 2H), 7.34 (dd, J = 8.0, 4.8, 1H), 8.16 (d, J = 8.0, 1H), 8.61 (dd, J = 4.8, 1.6, 1H), 9.06 (d, J = 1.6, 1H); m/z = 945.5 (M + H, 100); R$_t$ = 15.48 (27) |
| 94 | —HC═CH— | sec-Bu | (4-chlorobenzyl ethyl) | 3.64 (s, 2H), 7.25-7.32 (m, 4H); m/z = 881 (M + H, 100); R$_t$ = 17.21 (27) |
| 95 | —HC═CH— | sec-Bu | (2,2,5-trimethyl-1,3-dioxane) | 1.59 (s, 3H), 1.60 (s, 3H), 7.28-7.34 (m, 4H); m/z = 909 (M + H, 100) |
| 96 | —HC═CH— | sec-Bu | (phenyl methyl ketone O-methyloxime) | 4.07 (s, 3H), 7.41-7.42 (m, 3H), 7.49-7.52 (m, 2H); m/z = 890 (M + H, 30); R$_t$ = 9.01 (12) |
| 97 | —HC═CH— | sec-Bu | (4-trifluoromethoxyphenyl methyl) | 7.29 (t, J = 8.1, 2H), 8.15 (dd, J = 6.9, 2.0, 2H); m/z = 917.5 (M + H, 100); R$_t$ = 17.87 (22) |

$^{a)}$For LC-MS, the retention time (R$_t$) and, in brackets, the total run time of the chromatogram in minutes is stated; the percentage of the mass found refers to the relative intensity, standardized to 100. The abbreviations used for describing the $^1$H-NMR signals are as follows: s (singlet), d (doublet), t (triplet), q (quartet), sym (symmetrical).

Method B:

5-O-tert-Butyldimethylsilyl-4'-O-isobutyryl-avermectin B$_1$ monosaccharide (VI-2) (—C$_{22}$R$^1$-A-C$_{23}$R$^2$— : —HC=CH—)

120 mg of 5-O-tert-butyldimethylsilyl-avermectin B1 monosaccharide are dissolved in about 15 ml of dichloromethane. Under argon, 1.7 mg of 4-dimethylaminopyridine, 43 mg of triethylamine and 15 mg of isobutyryl chloride are added, and the mixture is stirred at room temperature for 2 hours. A further 1.7 mg of 4-dimethylaminopyridine, 8 mg of triethylamine and 3 mg of isobutyryl chloride are added, and the mixture is stirred for 2 hours. After addition of saturated sodium bicarbonate solution, the mixture is extracted with dichloromethane, the organic phase is dried over sodium sulphate and the solvent is removed under reduced pressure. The residue is filtered through silica gel using cyclohexane/ethyl acetate (4:1). This gives 139 mg of 5-O-tert-butyldimethylsilyl-4'-O-isobutyryl-avermectin B1 monosaccharide (VI-2).

LC-MS: 935.6 (M+Na, 100%) C$_{51}$H$_{80}$O$_{12}$Si (913.267)
Retention time: 11.75 min (12 min)

Example 98

4'-O-Isobutyryl-avermectin B1 monosaccharide

—C$_{22}$R$^1$-A-C$_{23}$R$^2$— : —HC=CH—

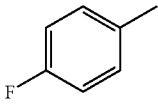

6 mg of 4-toluenesulphonic acid are added to a solution of 139 mg of 5-O-tert-butyldimethylsilyl-4'-O-isobutyryl-avermectin B1 monosaccharide (VI-2) in absolute methanol, and the mixture is stirred at room temperature for 2 hours. After addition of saturated sodium bicarbonate solution, the mixture is extracted with ethyl acetate, the organic phase is dried over sodium sulphate and the solvent is removed under reduced pressure. The residue is purified by preparative HPLC. This gives 34 mg of 4'-O-isobutyryl-avermectin B1 monosaccharide (Example 98).

LC-MS: 799.6 (M+H, 100%) C$_{45}$H$_{66}$O$_{12}$ (799.004)
Retention time: 8.84 min (12 min)
$^1$H-NMR (400 MHz, CDCl$_3$) selected signals: δ (ppm)= 1.21 (d, J=7.0, 3H), 1.22 (d, J=7.0, 3H), 2.58-2.63 (m, 1H).

The compounds of the formula (I) where R$^5$=H listed in the table below (Table 3) can be prepared analogously.

TABLE 3

| Ex. No. | —C$_{22}$R$^1$—A—C$_{23}$R$^2$— | R$^3$ | R$^4$ | Physical data[a] |
|---|---|---|---|---|
| 99 | —HC=CH— | sec-Bu | 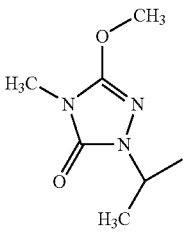 | δ (ppm) = 7.14 (t, J = 8.7, 2H), 8.11 (symmetr. m, 2H); m/z = 851.6 (M + H, 100); R$_t$ = 16.88 (22) |
| 100 | —HC=CH— | sec-Bu | | δ (ppm) = 1.66 and 1.68 (d, J = 7.4, together 3H), 3.12 (s, 3H), 3.95 and 3.97 (s, together 3H), 4.91-4.99 (m, 2H); m/z = 929.4 (M + 18, 15%); R$_t$ = 14.53, 14.72 (27) |

[a] For LC-MS, the retention time (R$_t$) and, in brackets, the total run time of the chromatogram in minutes is stated; the percentage of the mass found refers to the relative intensity, standardized to 100.
The abbreviations used for describing the $^1$H—NMR signals (selected signals) are as follows: s (singlet), d (doublet), t (triplet), q (quartet), sym (symmetrical).

Method C:

Example 101

4'-O-(piperazin-1-ylacetyl)-avermectin B1 monosaccharide (—$C_{22}R^1$-A-$C_{23}R^2$— : —HC=CH—)

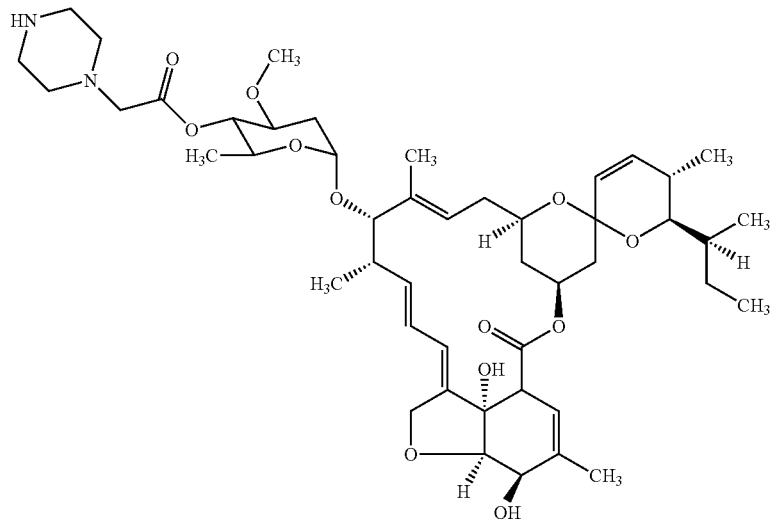

163 mg of 4'-O-{[4-(tert-butoxycarbonyl)piperazin-1-yl]acetyl}-avermectin B1 monosaccharide (compound from Ex. 103) are dissolved in 0.7 ml of ethyl acetate. Over a period of 3 hours, 2.1 ml of 3N hydrochloric acid are added in three portions to this solution, and the mixture is stirred for another 2 hours. After addition of saturated sodium bicarbonate solution, the mixture is extracted with ethyl acetate, the organic phase is separated off and dried over sodium sulphate and the solvent is removed under reduced pressure. The residue (154 mg) is purified by preparative HPLC (Waters 2996 photodiode array detector, 245 nm, x Terra Prep MS C18 Column 5 μm 19×100 mm, flow 20 ml/min water/acetonitrile). This gives 53 mg of 4'-O-(piperazin-1-ylacetyl)-avermectin B1 monosaccharide.

LC-MS: 855.5 (M+H, 100%) $C_{47}H_{70}N_2O_{12}$ (855.072)

Retention time: 10.57 min (27 min)

$^1$H-NMR (400 MHz, CDCl$_3$) selected signals: δ (ppm)= 2.73-2.87 (m, 4H), 3.10-3.18 (m, 4H).

Example 53

4'-O-{[4-(tert-Butoxycarbonyl)piperazin-1-yl]acetyl}-avermectin B1 monosaccharide (—$C_{22}R^1$-A-$C_{23}R^2$— : —HC=CH—)

At intervals of 3-4 hours, 48 mg of 4-toluenesulphonic acid are added in three portions to a solution of 221 mg of 5-O-tert-butyldimethylsilyl-4'-O-{[4-(tert-butoxycarbonyl)piperazin-1-yl]acetyl}-avermectin B1 monosaccharide (VI-3) in absolute methanol, and the mixture is stirred at room temperature until the reaction has gone to completion. After addition of saturated sodium bicarbonate solution, the mixture is extracted with ethyl acetate, the organic phase is separated off and dried over sodium sulphate and the solvent is removed under reduced pressure. This gives 163 mg of 4'-O-{[4-(tert-butoxycarbonyl)piperazin-1-yl]acetyl}-avermectin B1 monosaccharide.

LC-MS: 955.6 (M+H, 100%) $C_{52}H_{78}N_2O_{14}$, MW: 955.188

Retention time: 14.18 min (27 min)

$^1$H-NMR (400 MHz, CDCl$_3$) selected signals: δ (ppm)= 1.46 (s, 9H), 2.49-2.60 (m, 5H), 3.28-3.32 (m, 3H), 3.46-3.52 (m, 5H).

5-O-tert-Butyldimethylsilyl-4'-O-{[4-(tert-butoxycarbonyl)piperazin-1-yl]acetyl}-avermectin B1 monosaccharide (—$C_{22}R^1$-A-$C_{23}R^2$— : —HC=CH—) (VI-3)

200 mg of 5-O-tert-butyldimethylsilyl-avermectin B$_1$ monosaccharide (IV-1) are dissolved in 5 ml of dichloromethane. Under argon, 136 mg of N-(3-dimethylaminopropyl)-N'-ethylcarbodiimide, 87 mg of 4-dimethylaminopyridine (DMAP), 199 mg of 2-(1-tert-butoxycarbonylpiperazin-4-yl)acetic acid and a little molecular sieve are added, and the mixture is stirred at room temperature for 4 hours. After addition of saturated sodium bicarbonate solution, the org. phase is separated on a semipermeable cartridge from the aqueous phase and then filtered through a sodium sulphate/silica gel cartridge, and the solvent is removed under reduced pressure. This gives 221 mg of 5-O-tert-butyldimethylsilyl-4'-O-{[4-(tert-butoxycarbonyl)piperazin-1-yl]acetyl}-avermectin B1 monosaccharide (VI-3).

LC-MS: 1069.6 (M+H, 100%) $C_{58}H_{92}N_2O_{14}Si$ (1069.45)

Retention time: 20.18 min (27 min)

The compounds of the formula (I) where $R^5$=H listed in the table below (Table 4) can be prepared analogously.

TABLE 4

| Ex. No | —C$_{22}$R$^1$—A—C$_{23}$R$^2$— | R$^3$ | R$^4$ | Physical data[a] |
|---|---|---|---|---|
| 103 | —H$_2$C—CH$_2$— | sec-Bu | H$_2$N—CH$_2$—CH$_3$ | δ (ppm) = 3.49 (d, J = 5.5, 2H), 4.1 (broad, 1-2H); m/z = 770.5 (M − 18, 100), 788 (M + H, 10); R$_t$ = 10.66 (27) |
| 104 | —HC=CH— | sec-Bu | H$_3$C—NH—CH$_2$—CH$_3$ | δ (ppm) = 2.47 (s, 3H), 3.39-3.45 (m, 5H); m/z = 800.2 (M + H, 100); R$_t$ = 10.43 (27) |
| 105 | —HC=CH— | sec-Bu | 1-isopropyl-piperazinyl (CH$_3$, CH) | m/z = 869 (M + H, 100); R$_t$ = 9.67 (27) |

[a])For LC-MS, the retention time (R$_t$) and, in brackets, the total run time of the chromatogram in minutes is stated; the percentage of the mass found refers to the relative intensity, standardized to 100.
The abbreviations used for describing the $^1$H—NMR signals (selected signals) are as follows: s (singlet), d (doublet), t (triplet), q (quartet), sym (symmetrical).

Method D:

Example 106

4'-O-(2-Morpholin-4-ylpropanoyl)-avermectin B1 monosaccharide benzoate (—C$_{22}$R$^1$-A-C$_{23}$R$^2$—: —HC=CH—)

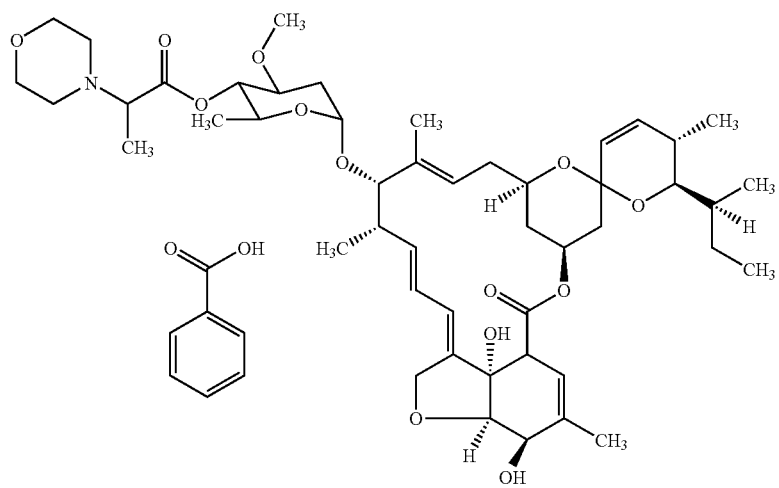

4 mg of benzoic acid are dissolved in 3 ml of dichloromethane. After addition of 30 mg of 4'-O-(2-morpholin-4-ylpropanoyl)-avermectin B1 monosaccharide (compound from Ex. 52, prepared according to Method A), the mixture is stirred briefly, the solvent is removed under reduced pressure and the residue is dried under high vacuum. This gives 33 mg of 4'-O-(2-morpholin-4-ylpropanoyl)-avermectin B1 monosaccharide benzoate.

LC-MS: 870 (M+H, 100) $C_{48}H_{71}NO_{13}$*$C_7H_6O_2$ (992.205)
Retention time: 12.02 min (27 min)
$^1$H-NMR (400 MHz, CDCl$_3$) selected signals: δ (ppm)= 2.61-2.72 (m, 4H), 3.27-3.33 (m, 2H), 3.64-3.79 (m, 5H), 7.45-7.51 (m, 2H), 7.58-7.62 (m, 1H), 8.10 (dd, J=8.3, 1.3, 2H).

The compound of the formula (I, $R^5$=H) shown below can be prepared analogously:

Example 107

4'-O-(piperazin-1-ylacetyl)-avermectin B1 monosaccharide dibenzoate

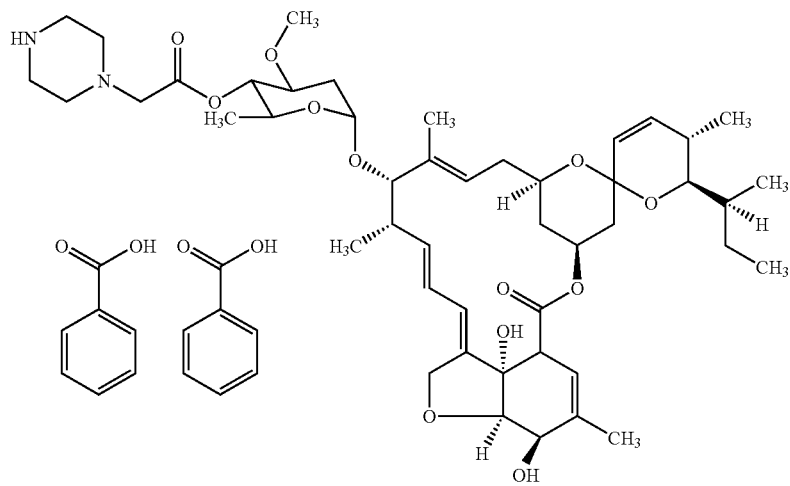

LC-MS: 855 (M+H, 100) $C_{47}H_{70}N_2O_{12}$*2 $C_7H_6O_2$ (1099.32)
Retention time: 10.04 min (27 min)
Preparation of the Starting Material of the Formula (V)

V-1 (2S)-2-(1H-Pyrazol-1-yl)propanoic acid a) 200 mg of N-ethyldiisopropylamine ("Hünig's base") are added to a solution of 82 mg of pyrazole in 5 ml of dichloromethane, and 300 mg of ethyl (2R)-2-{[(trifluoromethyl)-sulphonyl]oxy}propanoate in 2 ml of dichloromethane are added dropwise. The mixture is stirred at room temperature for a further 16 hours. After addition of saturated sodium bicarbonate solution, the mixture is extracted with ethyl acetate, the organic phase is dried over sodium sulphate and the solvent is removed under reduced pressure. This gives 250 mg of ethyl (2S)-2-(1H-pyrazol-1-yl)-propanoate in a purity of 96% (LC-MS).
LC-MS: 169.1 (M+H, 100%). $C_8H_{12}N_2O_2$ (168.195)
Retention time: 3.13 min (12 min)
$^1$H-NMR (400 MHz, CD$_3$CN): δ (ppm)=1.19 (t, J=7.1, 3H), 1.70 (d, J=7.3, 3H), 4.13 (dq, J=7.1, 2.1, 2H), 5.10 (q, J=7.3, 1H), 6.28 (t, J=2.3, 1H), 7.46 (d, J=1.4, 1H), 7.62 (dd, J=2.3, 0.4, 1H).

b) 62 mg of lithium hydroxide and 1 ml of water are added to a solution of 250 mg of ethyl (2S)-2-(1H-pyrazol-1-yl)propanoate in 3 ml of tetrahydrofuran. The mixture is stirred at room temperature for 4 hours. After addition of 1N aqueous hydrochloric acid, the mixture is extracted with ethyl acetate, the organic phase is dried over sodium sulphate and the solvent is removed under reduced pressure. This gives 195 mg of (2S)-2-(1H-Pyrazol-1-yl)propanoic acid (V-1) in a purity of 93% (LC-MS).

LC-MS: 141.1 (M+H, 100%) $C_6H_8N_2O_2$ (140.141)
Retention time: 1.12 min (12 min)
$^1$H-NMR (400 MHz, DMSO-d$_6$): δ (ppm)=1.64 (d, J=7.3, 3H), 5.12 (q, J=7.3, 1H), 6.26 (t, J=2.2, 1H), 7.44 (dd, J=1.2, 0.5, 1H), 7.79 (dd, J=1.8, 0.5, 1H), 12.9 (s, broad, 1H).

The compounds of the formula (V) where LG=OH listed in the table below (Table 5) can be prepared analogously.

TABLE 5

| Ex. No. | $R^4$ | Physical data[a] |
|---|---|---|
| V-2 | (triazolyl, S) | LC-MS: m/z = 142.1 (M + H, 100%)<br>R$_t$: 0.85 min (12 min)<br>$C_5H_7N_3O_2$ (141.129) |
| V-3 | (imidazolyl, S) | LC-MS: m/z = 141.1 (M + H, 100%)<br>R$_t$: 0.41 min (12 min)<br>$C_6H_8N_2O_2$ (140.141) |
| V-4 | (triazolyl, R) | LC-MS: m/z = 142.1 (M + H, 100%)<br>R$_t$: 0.50 min (12 min)<br>$C_5H_7N_3O_2$ (141.129) |

TABLE 5-continued

| Ex. No. | R⁴ | Physical data[a] |
|---|---|---|
| V-5 | 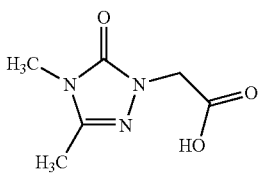 | LC-MS: m/z = 141.1 (M + H, 100%)<br>$R_t$: 0.96 min (12 min)<br>$C_6H_8N_2O_2$ (140.141) |

[a] For LC-MS, the retention time ($R_t$) and, in brackets, the total run time of the chromatogram in minutes is stated; the percentage of the mass found refers to the relative intensity, standardized to 100.

V-6 (3,4-Dimethyl-5-oxo-4,5-dihydro-1H-1,2,4-triazol-1-yl)acetic acid 593 mg of methyl (3,4-dimethyl-5-oxo-4,5-dihydro-1H-1,2,4-triazol-1-yl)acetate (Va-6) are dissolved in 5 ml of tetrahydrofuran, and 134 mg of lithium hydroxide in 2 ml of water are added. The mixture is stirred at room temperature for 16 hours, acidified with 1N hydrochloric acid and extracted with ethyl acetate. The organic phase is dried over sodium sulphate and the solvent is removed under reduced pressure. This gives 167 mg of (3,4-dimethyl-5-oxo-4,5-dihydro-1H-1,2,4-triazol-1-yl)acetic acid.

LC-MS: 172 (M+H, 100%) $C_6H_9N_3O_3$ (171.155)
Retention time: 0.45 min (12 min)

Va-6 Methyl (3,4-dimethyl-5-oxo-4,5-dihydro-1H-1,2,4-triazol-1-yl)acetate 1222 mg of potassium carbonate are added to a solution of 500 mg of 4,5-dimethyl-2,4-dihydro-3H-1,2,4-triazol-3-one in 15 ml of acetonitrile, and the mixture is warmed to 50° C. After addition of 879 mg of methyl bromoacetate, the mixture is heated at reflux for 16 hours. The mixture is concentrated under reduced pressure, the residue is taken up in dichloromethane, washed with diluted hydrochloric acid (pH 2) and dried over sodium sulphate, and the solvent is removed under reduced pressure. This gives 593 mg of methyl (3,4-dimethyl-5-oxo-4,5-dihydro-1H-1,2,4-triazol-1-yl)acetate (Va-6) in a purity of 93% (LCMS).

LC-MS: 186 (M+H, 100%) $C_7H_{11}N_3O_3$ (185.182)
Retention time: 0.58 min (12 min)

The compounds of the formula (V) with LG=OH listed in the table below (Table 6) can be prepared analogously.

TABLE 6

| Ex. No. | R⁴ | Physical data |
|---|---|---|
| V-7 | 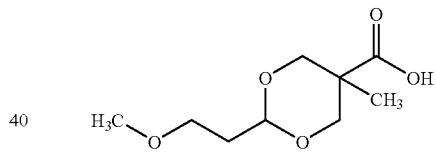 | LC-MS: m/z = 198 (M + H)<br>$R_t$: 0.81 min (12 min)<br>$C_8H_{11}N_3O_3$ (197.193) |
| V-8 | | LC-MS: m/z = 188 (M + H)<br>$R_t$: 0.71 min (12 min)<br>$C_6H_9N_3O_4$ (187.154) |

[a] For LC-MS, the retention time ($R_t$) and, in brackets, the total run time of the chromatogram in minutes is stated; the percentage of the mass found refers to the relative intensity, standardized to 100.

V-9 2-(2-Methoxyethyl)-5-methyl-1,3-dioxane-5-carboxylic acid 478 mg of methyl 2-(2-methoxyethyl)-5-methyl-1,3-dioxane-5-carboxylate (Va-9) are dissolved in 8 ml of tetrahydrofuran, and 92 mg of lithium hydroxide in 2 ml of water are added. The mixture is stirred at room temperature for 16 hours, 92 mg of lithium hydroxide, dissolved in 2 ml of water, are added, and the mixture is stirred for 24 hours. The mixture is acidified with 1N hydrochloric acid and extracted with ethyl acetate, and the solvent of the organic phase is removed under reduced pressure. Water is added to the residue, and the mixture is made basic using 1N aqueous sodium hydroxide solution and extracted with ethyl acetate. The aqueous phase is acidified with 1N hydrochloric acid and extracted with ethyl acetate, the organic phase is separated off and dried over sodium sulphate and the solvent is removed under reduced pressure. This gives 261 mg of 2-(2-methoxyethyl)-5-methyl-1,3-dioxane-5-carboxylic acid as a mixture of two isomeric forms in a purity of about 78% (LCMS).

LC-MS: 205 (M+H, 100%) $C_9H_{16}O_5$ (204.22)
Retention time: 2.27 min and 2.70 min (12 min)

Va-9 Methyl 2-(2-methoxyethyl)-5-methyl-1,3-dioxane-5-carboxylate 51 mg of 4-toluenesulphonic acid are added to a solution of 400 mg of methyl 3-hydroxyl-2-(hydroxymethyl)-2-methylpropanoate and 362 mg of 1,1,3-trimethoxypropane in toluene, and the mixture is stirred at 80° C. for 4 hours. After addition of saturated sodium bicarbonate solution, the organic phase is separated off and dried over sodium sulphate, and the solvent is removed under reduced pressure. The residue is filtered through silica gel (mobile phase cyclohexane/ethyl acetate 4:1). This gives 478 mg of methyl 2-(2-methoxyethyl)-5-methyl-1,3-dioxane-5-carboxylate as a mixture of two isomeric forms in a purity of about 38% (LCMS).

LC-MS: 219 (M+H, 100%) $C_{10}H_{18}O_5$ (218.247)

Retention time: 3.39 min and 4.16 min (12 min)

V-10 4-(Ethoxycarbonyl)-3-(trifluoromethyl)-1H-pyrazol-1-yl acetic acid

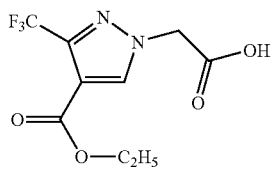

0.35 ml of trifluoroacetic acid is added to a solution of 742 mg of ethyl 1-(2-tert-butoxy-2-oxoethyl)-3-(trifluoromethyl)-1H-pyrazole-4-carboxylate (Va-10) in 0.35 ml of dichloromethane, and the mixture is stirred at room temperature for 90 min. After addition of 0.2 ml of dichloromethane and 0.2 ml of trifluoroacetic acid, the mixture is stirred for 5 hours and the solvent is removed under reduced pressure. The oily residue solidifies on standing to give a solid. This gives 780 mg of 4-(ethoxycarbonyl)-3-(trifluoromethyl)-1H-pyrazol-1-yl acetic acid in a purity of about 50% (LCMS).

LC-MS: 267 (M+H, 100%) $C_9H_9F_3N_2O_4$ (266.174)

Retention time: 2.01 min (6 min)

$^1$H-NMR (400 MHz, $D_6$-DMSO): δ (ppm)=1.28 (t, J=7.1, 3H), 4.26 (q, J=7.1, 2H), 5.10 (s, 2H), 8.53 (d, J=0.9, 1H).

Va-10 Ethyl 1-(2-tert-butoxy-2-oxoethyl)-3-(trifluoromethyl)-1H-pyrazole-4-carboxylate 404 mg of Hünig-base and 469 mg of tert-butyl bromoacetate, dissolved in 2 ml of dichloromethane, are added to a solution of 50 mg of ethyl 3-(trifluoromethyl)-1H-pyrazole-4-carboxylate in 10 ml of dichloromethane. The mixture is stirred at room temperature for 16 hours. After addition of saturated sodium bicarbonate solution, the mixture is extracted with ethyl acetate, the organic phase is separated off and dried over sodium sulphate and the solvent is removed under reduced pressure. This gives 742 mg of ethyl 1-(2-tert-butoxy-2-oxoethyl)-3-(trifluoromethyl)-1H-pyrazole-4-carboxylate (Va-10) in a purity of about 78% (LCMS).

LC-MS: 267 (M-tert-butyl, 100%) $C_{13}H_{17}F_3N_2O_4$ (322.281)

Retention time: 3.27 min (6 min)

BIOLOGICAL COMPARATIVE EXAMPLES

I) Compounds of the Formula (I); $—C_{22}R^1-A-C_{23}R^2—$ Represents a —HC=CH— Grouping Example A

*Lucilia cuprina* Test (LUCICU)
Description for Examples A and B
Solvent: Dimethyl sulphoxide To produce a suitable preparation of active compound, 1 part by weight of active compound is mixed with the stated amount of water and the concentrate is diluted with water to the desired concentration.

Containers containing horsemeat treated with the active compound preparation of the desired concentration are populated with *Lucilia cuprina* larvae.

After the desired period of time, the kill in % is determined. 100% means that all larvae have been killed; 0% means that none of the larvae have been killed.

In this test, for example, the following compounds of the preparation examples show good activity: see table

*Lucilia cuprina* Test (LUCICU)

| Example No. | Concentration of active compound in ppm | Kill rate in % after 2 days |
| --- | --- | --- |
| 4'-O-acetyl-4'-O-de(2,6-dideoxy-3-O-methyl-α-L-arabino-hexopyrano-syl)-5-O-demethyl-avermectin A1a[a] | 0.8 | 30 |
| 1 | 0.8 | 100 |
| 4 | 0.8 | 100 |
| 5 | 0.8 | 100 |
| 6 | 0.8 | 98 |
| 7 | 0.8 | 98 |
| 8 | 0.8 | 100 |
| 9 | 0.8 | 100 |
| 11 | 0.8 | 100 |
| 12 | 0.8 | 100 |
| 14 | 0.8 | 100 |
| 15 | 0.8 | 100 |
| 16 | 0.8 | 100 |
| 20 | 0.8 | 100 |
| 25 | 0.8 | 95 |
| 26 | 0.8 | 100 |
| 27 | 0.8 | 100 |
| 48 | 0.8 | 100 |
| 50 | 0.8 | 100 |
| 52 | 0.8 | 100 |
| 54 | 0.8 | 80 |
| 55 | 0.8 | 90 |
| 57 | 0.8 | 100 |
| 60 | 0.8 | 90 |
| 98 | 0.8 | 95 |
| 100 | 0.8 | 100 |

[a] known from U.S. Pat. No. 4,201,861 and JP 54-06197

Example B

*Lucilia cuprina* Test (LUCICU)

| Example No. | Concentration of active compound in ppm | Kill rate in % after 2 days |
| --- | --- | --- |
| 4'-O-acetyl-4'-O-de(2,6-dideoxy-3-O-methyl-α-L-arabino-hexopyrano-syl)-5- | 0.16 | 0 |

-continued

| Example No. | Concentration of active compound in ppm | Kill rate in % after 2 days |
|---|---|---|
| O-demethyl-avermectin A1a[a] | | |
| 18 | 0.16 | 100 |
| 19 | 0.16 | 100 |

[a]known from U.S. Pat. No. 4,201,861 and JP 54-06197

Example C

*Musca domestica* Test (MUSCDO)
Solvent: Dimethyl sulphoxide

To produce a suitable preparation of active compound, 1 part by weight of active compound is mixed with the stated amount of water, and the concentrate is diluted with water to the desired concentration.

Containers containing a sponge treated with the preparation of active compound of the desired concentration are populated with adult *Musca domestica*.

After the desired period of time, the kill in % is determined. 100% means that all flies have been killed; 0% means that none of the flies have been killed.

In this test, for example, the following compounds of the preparation examples show good activity: see table
*Musca domestica* Test (MUSCDO)

| Example No. | Concentration of active compound in ppm | Kill rate in % after 2 days |
|---|---|---|
| 4'-O-acetyl-4'-O-de(2,6-dideoxy-3-O-methyl-α-L-arabino-hexopyrano-syl)-5-O-demethyl-avermectin A1a[a] | 100 | 60 |
| 48 | 100 | 100 |
| 50 | 100 | 90 |
| 57 | 100 | 90 |
| 60 | 100 | 100 |
| 55 | 100 | 90 |
| 89 | 100 | 100 |
| 90 | 100 | 100 |
| 91 | 100 | 90 |
| 92 | 100 | 90 |
| 93 | 100 | 100 |
| 94 | 100 | 80 |
| 95 | 100 | 80 |
| 4'-O-acetyl-4'-O-de(2,6-dideoxy-3-O-methyl-α-L-arabino-hexopyrano-syl)-5-O-demethyl-avermectin A1a[a] | 0.8 | 0 |
| 13 | 0.8 | 50 |

[a] known from U.S. Pat. No. 4,201,861 and JP 54-06197

Example D

Phaedon Test (PHAECO Spray Treatment)
Solvents: 78 parts by weight of acetone
1.5 parts by weight of dimethylformamide
Emulsifier: 0.5 part by weight of alkylaryl polyglyycol ether To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the preparation examples show good activity: see table
Phaedon Test (PHAECO Spray Treatment)

| Example No. | Concentration of active compound in ppm | Kill rate in % after 7 days |
|---|---|---|
| 4'-O-acetyl-4'-O-de(2,6-dideoxy-3-O-methyl-α-L-arabino-hexopyrano-syl)-5-O-demethyl-avermectin A1a[a] | 4 | 0 |
| 1 | 4 | 90 |
| 3 | 4 | 80 |
| 20 | 4 | 80 |

[a]known from U.S. Pat. No. 4,201,861 and JP 54-06197

Example E

*Bemisia tabaci* Test, Normally Sensitive Strains, (BEMITA)
Solvent: 7 parts by weight of dimethylformamide
Emulsifier: 10 parts by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Cotton plants (*Gossypium hirsutum*) infected by eggs, larvae and pupae of the whitefly (*Bemisia tabaci*) are treated by being sprayed with the preparation of active compound at the desired concentration.

After the desired period of time, the kill in % is determined 100% means that all animals have been killed; 0% means that none of the animals have been killed.

In this test, for example, the following compounds of the preparation examples show good activity: see table
*Bemisia tabaci* Test, Normally Sensitive Strain, (BEMITA)

| Example No. | Concentration of active compound in ppm | Kill rate in % after 7 days |
|---|---|---|
| 4'-O-acetyl-4'-O-de(2,6-dideoxy-3-O-methyl-α-L-arabino-hexopyrano-syl)-5-O-demethyl-avermectin A1a[a] | 0.8 | 0 |
| 14 | 0.8 | 80 |

[a]known from U.S. Pat. No. 4,201,861 and JP 54-06197

Example F

*Tetranychus* Test, OP-resistant (TETRUR Spray Treatment)
Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) heavily infested by all stages of the greenhouse red spider mite (*Tetranychus urticae*) are sprayed with a preparation of active compound of the desired concentration.

After the desired period of time, the effect in % is determined 100% means that all spider mites have been killed; 0% means that none of the spider mites have been killed.

In this test, for example, the following compounds of the preparation examples show good activity: see table
*Tetranychus* Test, OP-Resistant (TETRUR Spray Treatment)

| Example No. | Concentration of active compound in ppm | Kill rate in % after 5 days |
|---|---|---|
| 4'-O-acetyl-4'-O-de(2,6-dideoxy-3-O-methyl-α-L-arabino-hexopyrano-syl)-5-O-demethyl-avermectin A1a[a] | 0.00128 | 0 |
| 2 | 0.00128 | 80 |

[a]known from U.S. Pat. No. 4,201,861 and JP 54-06197

II) Compounds of the Formula (I); —$C_{22}R^1$-A-$C_{23}R^2$— Represents a —$H_2C$—$CH_2$— Grouping Example G Phaedon Test (PHAECO Spray Treatment)
Solvents: 78 parts by weight of acetone
　1.5 parts by weight of dimethylformamide
Emulsifier: 0.5 part by weight of alkylaryl polyglyycol ether
　To produce a suitable preparation of active compound, 1 part by weight of active compound is mixed with the stated amount of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the preparation examples show good activity: see table
Phaedon Test (PHAECO Spray Treatment)

| Example No. | Concentration of active compound in ppm | Kill rate in % after 7 days |
|---|---|---|
| 4'-O-acetyl-4'-O-de(2,6-dideoxy-3-O-methyl-α-L-arabino-hexopyranosyl)-5-O-demethyl-25-de(1-methylpropyl)-22,23-dihydro-25-(1-methylethyl)-avermectin A1a[a] | 4 | 0 |
| 17 | 4 | 100 |
| 18 | 4 | 100 |
| 21 | 4 | 83 |
| 22 | 4 | 100 |
| 23 | 4 | 100 |
| 24 | 4 | 83 |
| 28 | 4 | 100 |
| 29 | 4 | 100 |
| 31 | 4 | 100 |
| 32 | 4 | 100 |
| 33 | 4 | 100 |
| 34 | 4 | 100 |
| 35 | 4 | 100 |
| 36 | 4 | 100 |
| 37 | 4 | 100 |
| 40 | 4 | 100 |
| 41 | 4 | 83 |
| 42 | 4 | 83 |
| 43 | 4 | 100 |
| 44 | 4 | 100 |
| 45 | 4 | 100 |
| 48 | 4 | 100 |
| 50 | 4 | 83 |
| 51 | 4 | 100 |
| 52 | 4 | 100 |
| 53 | 4 | 100 |
| 54 | 4 | 100 |
| 56 | 4 | 100 |
| 57 | 4 | 100 |
| 58 | 4 | 100 |
| 59 | 4 | 100 |
| 60 | 4 | 100 |
| 61 | 4 | 100 |
| 62 | 4 | 100 |
| 63 | 4 | 100 |
| 64 | 4 | 100 |
| 65 | 4 | 100 |
| 66 | 4 | 100 |
| 67 | 4 | 100 |
| 68 | 4 | 100 |
| 69 | 4 | 100 |
| 70 | 4 | 100 |
| 71 | 4 | 100 |
| 72 | 4 | 100 |
| 73 | 4 | 100 |
| 74 | 4 | 100 |
| 75 | 4 | 100 |
| 76 | 4 | 100 |
| 77 | 4 | 100 |
| 78 | 4 | 100 |
| 79 | 4 | 100 |
| 80 | 4 | 100 |
| 81 | 4 | 100 |
| 82 | 4 | 100 |
| 83 | 4 | 100 |
| 84 | 4 | 100 |
| 85 | 4 | 83 |
| 87 | 4 | 100 |
| 88 | 4 | 100 |
| 96 | 4 | 83 |
| 101 | 4 | 100 |
| 103 | 4 | 100 |
| 104 | 4 | 100 |
| 105 | 4 | 100 |
| 106 | 4 | 100 |
| 107 | 4 | 100 |

[a]known from EP 0 235 085 A1

Example H

*Tetranychus* Test, OP-resistant (TETRUR Spray Treatment)
Solvents: 78 parts by weight of acetone
　1.5 parts by weight of dimethylformamide
Emulsifier: 0.5 part by weight of alkylaryl polyglycol ether
　To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) heavily infested by all stages of the greenhouse red spider mite (*Tetranychus urticae*) are sprayed with a preparation of active compound of the desired concentration.

After the desired period of time, the effect in % is determined. 100% means that all spider mites have been killed; 0% means that none of the spider mites have been killed.

In this test, for example, the following compounds of the preparation examples show good activity: see table

*Tetranychus* Test, OP-resistant (TETRUR Spray Treatment)

| Example No. | Concentration of active compound in ppm | Kill rate in % after 5 days |
|---|---|---|
| 4'-O-acetyl-4'-O-de(2,6-dideoxy-3-O-methyl-α-L-arabino-hexopyranosyl)-5-O-demethyl-25-de(1-methylpropyl)-22,23-dihydro-25-(1-methylethyl)-avermectin A1a[a] | 0.032 | 0 |
| 17 | 0.032 | 70 |
| 21 | 0.032 | 70 |
| 23 | 0.032 | 70 |

[a] known from EP 0 235 085 A1

Example I

*Spodoptera frugiperda* Test (SPODFR Spray Treatment)
Solvents: 78.0 parts by weight of acetone
1.5 parts by weight of dimethylformamide
Emulsifier: 0.5 part by weight of alkylaryl polyglyycol ether To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after drying, populated with caterpillars of the army worm (*Spodoptera frugiperda*).

After the desired period of time, the effect in % is determined. 100% means that all caterpillars have been killed; 0% means that none of the caterpillars have been killed.

In this test, for example, the following compounds of the preparation examples show good activity: see table

| Example No. | Concentration of active compound in ppm | Kill rate in % after 5 days |
|---|---|---|
| 4'-O-acetyl-4'-O-de(2,6-dideoxy-3-O-methyl-α-L-arabino-hexopyranosyl)-5-O-demethyl-25-de(1-methylpropyl)-22,23-dihydro-25-(1-methylethyl)-avermectin A1a[a] | 4 | 0 |
| 28 | 4 | 100 |
| 29 | 4 | 100 |
| 30 | 4 | 100 |
| 32 | 4 | 100 |
| 33 | 4 | 100 |
| 34 | 4 | 100 |
| 35 | 4 | 100 |
| 36 | 4 | 83 |
| 38 | 4 | 100 |
| 39 | 4 | 100 |
| 40 | 4 | 100 |
| 42 | 4 | 100 |
| 45 | 4 | 100 |
| 46 | 4 | 100 |
| 47 | 4 | 100 |
| 48 | 4 | 100 |
| 49 | 4 | 100 |
| 50 | 4 | 100 |
| 52 | 4 | 100 |
| 59 | 4 | 100 |
| 66 | 4 | 100 |
| 67 | 4 | 100 |
| 68 | 4 | 100 |
| 69 | 4 | 100 |
| 70 | 4 | 100 |
| 71 | 4 | 100 |
| 72 | 4 | 100 |
| 74 | 4 | 100 |
| 75 | 4 | 100 |
| 76 | 4 | 100 |
| 78 | 4 | 100 |
| 80 | 4 | 100 |
| 81 | 4 | 100 |
| 82 | 4 | 100 |
| 83 | 4 | 100 |
| 84 | 4 | 100 |
| 85 | 4 | 100 |
| 86 | 4 | 100 |
| 87 | 4 | 100 |
| 88 | 4 | 100 |
| 99 | 4 | 100 |
| 103 | 4 | 100 |
| 105 | 4 | 100 |
| 106 | 4 | 100 |
| 107 | 4 | 100 |
| 4'-O-(4-chlorobenzoyl)-4'-O-de(2,6-dideoxy-3-O-methyl-α-L-arabino-hexopyranosyl)-5-O-demethyl-avermectin A1a[b] | 4 | 0 |
| 97 | 4 | 33 |

[a] cf. EP 0 235 085 A1, [b] known from U.S. Pat. No. 4,201,861 and JP 54-06197

Example J

*Ctenocephalides felis*; Oral (CTECFE)

Solvent: Dimethyl sulphoxide

To produce a suitable preparation of active compound, 1 part by weight of active compound is mixed with the stated amount of solvent. Part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. The blood is warmed to 37° C., but the flea chamber is at room temperature.

After the desired period of time, the kill in % is determined. 100% means that all fleas have been killed; 0% means that none of the fleas have been killed.

In this test, for example, the following compounds of the preparation examples show good activity: see table

| Example No. | Concentration of active compound in ppm | Kill rate in % after 2 days |
|---|---|---|
| 4'-O-acetyl-4'-O-de(2,6-dideoxy-3-O-methyl-α-L-arabino-hexopyranosyl)-5-O-demethyl-25-de(1-methylpropyl)-22,23-dihydro-25-(1-methylethyl)-avermectin A1a[a)] | 4 | 20 |
| 50 | 4 | 50 |
| 52 | 4 | 50 |
| 57 | 4 | 40 |
| 60 | 4 | 50 |

The invention claimed is:

1. An Avermectin derivative of formula (I)

(I)

in which the grouping —$C_{22}R^1$-A-$C_{23}R^2$— represents —HC=CH—, —$H_2$C—CH(OH)— or —$H_2$C—$CH_2$—, $R^3$ represents sec-butyl, isopropyl or cyclohexyl, $R^5$ represents hydrogen, methyl or $C_{1-4}$-alkylcarbonyl, and $R^4$ represents optionally substituted $C_{2-6}$-alkyl, $C_{2-6}$-alkenyl, $C_{2-6}$-alkynyl, $C_{1-6}$-alkoxy-$C_{1-4}$-alkyl, $C_{1-4}$-alkoxy-$C_{1-4}$-alkoxy-$C_{1-4}$-alkyl, cycloalkyl, cycloalkenyl, cycloalkyl-$C_{1-4}$-alkyl, aryl except for 4-chlorophenyl, aryl-$C_{1-4}$-alkyl, hetaryl, hetaryl-$C_{1-4}$-alkyl, heterocyclyl or heterocyclyl-$C_{1-4}$-alkyl, or represents a radical selected from the radicals ($G^7$) to ($G^{14}$)

(G7)

(G8)

(G9)

(G10)

(G11)

(G12)

(G13)

(G14)

in which

B represents optionally $R^8$-, $R^9$- and $R^{10}$-substituted aryl, cycloalkyl, heterocyclyl, hetaryl or $NR^{19}R^{20}$, D represents optionally $R^8$-, $R^9$- and $R^{10}$-substituted aryl, cycloalkyl, heterocyclyl, hetaryl or $NR^{19}R^{20}$, $R^6$ represents hydrogen, halogen, in particular fluorine, cyano, optionally substituted alkyl, alkenyl, alkynyl, cycloalkyl or heterocyclyl, $R^7$ represents hydrogen, halogen, in particular fluorine, cyano, optionally substituted alkyl, alkenyl, alkynyl or $R^6$ and $R^7$ together with the atom to which they are attached represent a 3-, 4-, 5-, 6- or 7-membered ring which is optionally substituted and/or optionally interrupted by oxygen, sulphur, nitrogen, sulphinyl or sulphonyl, or $R^6$ and $R^7$ together with the atom to which they are attached represent an optionally substituted exo-methylene bond, $R^8$ represents hydrogen, optionally substituted $C_{1-4}$-alkyl, $C_{3-6}$-cycloalkyl, $C_{1-4}$-haloalkyl, $C_{1-4}$-alkoxy, $C_{1-4}$-alkoxy-$C_{1-4}$-alkoxy, $C_{1-4}$-haloalkoxy, $C_{1-4}$-alkylthio, $C_{1-4}$-haloalkylthio, $C_{1-4}$-alkyl-sulphinyl, $C_{1-4}$-haloalkylsulphinyl, $C_{1-4}$-alkylsulphonyl, $C_{1-4}$-haloalkylsulphonyl, hetaryl, halogen, nitro, cyano, amino, $C_{1-4}$-alkylamino, di-($C_{1-4}$-alkyl)-amino, or represents a radical selected from the group consisting of CO—OH, COO[(−)], COO—$C_{1-6}$-alkyl, NH—CHO, NH—CO—$C_{1-4}$-alkoxy, N($C_{1-4}$-alkyl)-CO—$C_{1-4}$-alkoxy, P(O)(OH)$_2$, P(O)O[(−)]$_2$, CO—$NH_2$, CS—$NH_2$, C(=NH)—$NH_2$, C(=N—OH)—$NH_2$, CO—NH—$C_{1-4}$-alkyl, CO—N—($C_{1-4}$-alkyl)$_2$, CO—NH—$C_{1-4}$-alkoxy, CO—NH—CO—$C_{1-4}$-alkyl, CO—NH—CO—$C_{1-4}$-haloalkyl, CO—NH—CO—$C_{3-7}$-cycloalkyl, CO—NH—CO—$C_{1-4}$-alkoxy, CO—NH—CO-(aryl- $C_{1-2}$-alkyloxy), $SO_2$—OH, $SO_2$—$O^{(-)}$, $SO_2$—$NH_2$, $SO_2$—NH—$C_{1-4}$-alkyl, $SO_2$—N—$(C_{1-4}$-alkyl$)_2$, CO—NH—$SO_2$—NH—$C_{1-4}$-alkyl, CO—NH—$SO_2$—N[di($C_{1-4}$-alkyl), and CO—O—$C_{1-6}$-alkyl, $R^9$ represents hydrogen or optionally substituted $C_{1-4}$-alkyl, $C_{1-4}$-haloalkyl, $C_{1-4}$-alkoxy, $C_{1-4}$-haloalkoxy, $C_{1-4}$-alkylthio, $C_{1-4}$-alkylsulphinyl, $C_{1-4}$-alkylsulphonyl, halogen, nitro, cyano, formyl, $C_{1-4}$-alkylcarbonyl, amino, $C_{1-4}$-alkylamino, di-($C_{1-4}$-alkyl)-amino, optionally substituted aryl, optionally substituted hetaryl or optionally substituted heterocyclyl, $R^{10}$ represents hydrogen or optionally substituted $C_{1-4}$-alkyl, $C_{2-4}$-alkenyl, $C_{2-4}$-alkynyl, $C_{1-4}$-haloalkyl, $C_{1-4}$-alkylcarbonyl, $C_{1-4}$-alkoxycarbonyl, $R^{11}$ represents hydrogen, cyano or optionally substituted $C_{1-6}$-alkyl, $R^{12}$ and $R^{13}$ independently of one another represents hydrogen, hydroxyl, or optionally substituted $C_{1-4}$-alkyl, $C_{2-4}$-alkenyl, $C_{2-4}$-alkynyl, $C_{1-6}$-alkylcarbonyl, $C_{1-6}$-alkylamino, di-($C_{1-6}$-alkyl)-amino, $C_{1-6}$-alkylamino-$C_{1-4}$-alkyl, di-($C_{1-6}$-alkyl)-amino-$C_{1-4}$-alkyl, $C_{1-6}$-alkoxy-$C_{1-4}$-alkyl, amino-$C_{1-4}$-alkyl, $C_{3-6}$-cycloalkyl, aryl, aryl-$C_{1-4}$-alkyl, hetaryl-$C_{1-4}$-alkyl, heterocyclyl, heterocyclyl-$C_{1-4}$-alkyl or hetaryl, or $R^{12}$ and $R^{13}$ together with the atom to which they are attached represent an optionally substituted 3-, 4-, 5-, 6- or 7-membered ring which may optionally be interrupted by oxygen, sulphur, nitrogen, sulphinyl or sulphonyl, or $R^{12}$ and $R^{13}$ together with the atom to which they are attached represent

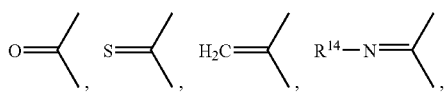

X represents oxygen, sulphur, sulphinyl, sulphonyl or N—$R^{14}$, where $R^{14}$ represents hydrogen or optionally substituted $C_{1-4}$-alkyl, Y represents oxygen, sulphur, sulphinyl, sulphonyl or N—$R^{15}$, where $R^{15}$ represents hydrogen, optionally substituted $C_{1-4}$-alkyl, $R^{16}$ represents methyl, chlorine, bromine or trifluoromethyl, $R^{17}$ represents methyl, chlorine or bromine, $R^{18}$ represents hydrogen or optionally substituted $C_{1-4}$-alkyl, aryl-$C_{1-4}$-alkyl or hetaryl-$C_{1-4}$-alkyl, $R^{19}$ and $R^{20}$ independently of one another represent hydrogen or optionally substituted $C_{1-4}$-alkyl, $C_{1-4}$-haloalkyl, $C_{1-4}$-alkoxycarbonyl, $C_{1-4}$-alkylcarbonyl, $C_{1-6}$-alkoxy-$C_{1-4}$-alkyl, $C_{1-6}$-alkylamino-$C_{1-4}$-alkyl, di-($C_{1-6}$-alkyl)-amino-$C_{1-4}$-alkyl, $C_{1-4}$-alkoxycarbamoyl, $C_{2-6}$-alkenyl, $C_{2-6}$-alkynyl, aryl-$C_{1-4}$-alkyl, hetaryl-$C_{1-4}$-alkyl, or $R^{19}$ and $R^{20}$ together with the nitrogen atom to which they are attached represent a cyclic amino group or represent a 3-, 4-, 5-, 6- or 7-membered ring which is optionally interrupted by oxygen, sulphur, nitrogen, sulphinyl or sulphonyl and/or which is optionally substituted by at least one radical as defined in $R^8$, $R^9$ and $R^{10}$.

2. A process for the preparation of an avermectin derivative of formula (I) according to claim 1, said process comprising converting a compound of formula (II)

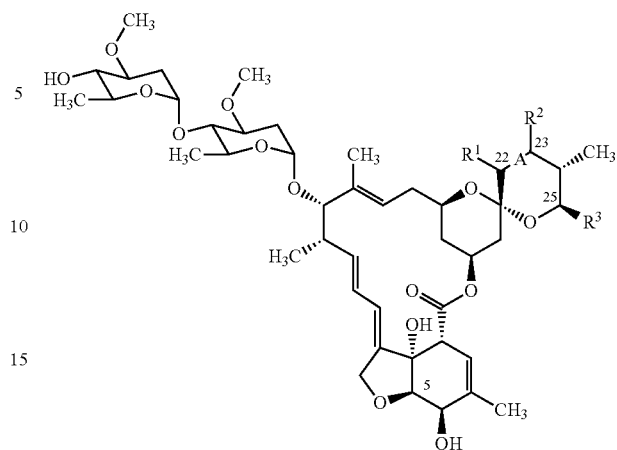

in the presence of a diluent and in the presence of an acidic reaction auxiliary into a compound of formula (III)

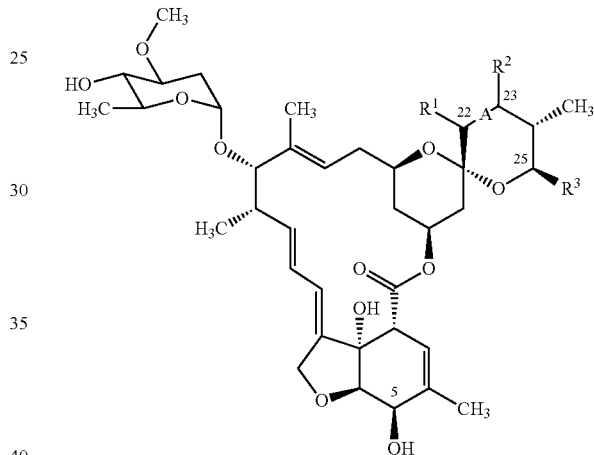

and converting the compound of formula (III) in the presence of a diluent and, if appropriate, in the presence of a basic reaction auxiliary with suitable protective groups into a macrocyclic lactone of formula (IV)

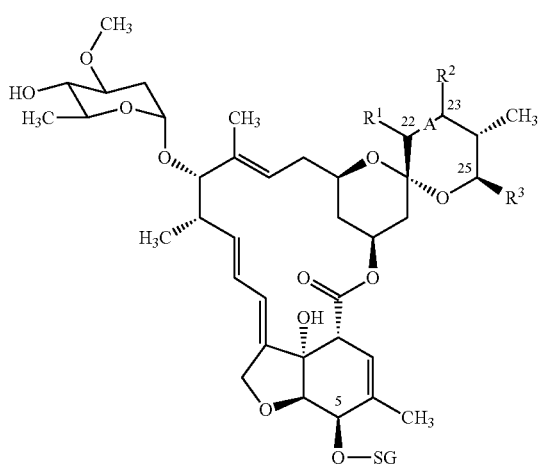

in which SG represents a suitable protective group radical, and reacting the compound of formula (IV), if appropriate in the presence of a diluent and if appropriate in the presence of a basic reaction auxiliary, with a compound of formula (V)

$$R^4-C(=O)-LG \quad (V)$$

in which

LG represents a nucleofugic leaving group which, if appropriate, may be generated in situ, to give a compound of formula (VI)

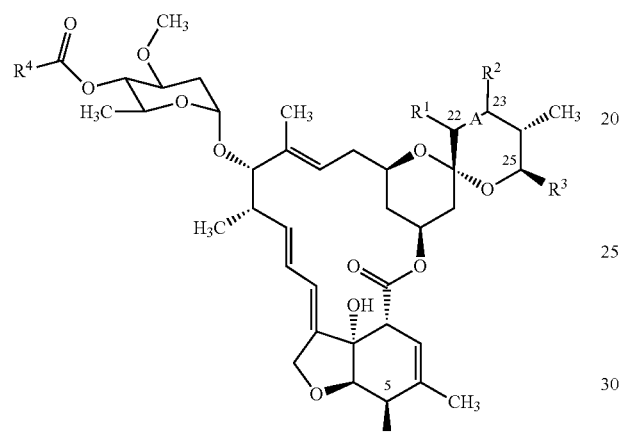

(VI)

and reacting the compound of formula (VI) under reaction conditions of a protective group deblocking, if appropriate in the presence of a diluent and if appropriate in the presence of a suitable acidic or basic reaction auxiliary.

3. A composition for controlling an insect, arachnid, nematode, or mollusc comprising at least one avermectin derivative of the formula (I) according to claim 1.

4. A method for controlling an insect, arachnid, nematode, or mollusc using an avermectin derivative of the formula (I) according to claim 1.

5. A method for controlling an insect, arachnid, nematode, or mollusc comprising applying an avermectin derivative of formula (I) according to claim 1 to animal pests and/or a habitat thereof.

6. A method for preparing a composition for controlling an insect, arachnid, nematode, or mollusc comprising forming said composition with at least one avermectin derivative of claim 1.

7. A method according to claim 5 where the animal parasites are parasitic arthropods.

8. A seed treatment comprising at least one avermectin derivative of formula (I) according to claim 1.

9. A treatment for transgenic plants comprising at least one avermectin derivative of formula (I) according to claim 1.

10. A seed treatment for transgenic plants comprising at least one avermectin derivative of formula (I) according to claim 1.

11. An avermectin derivative of formula (VI)

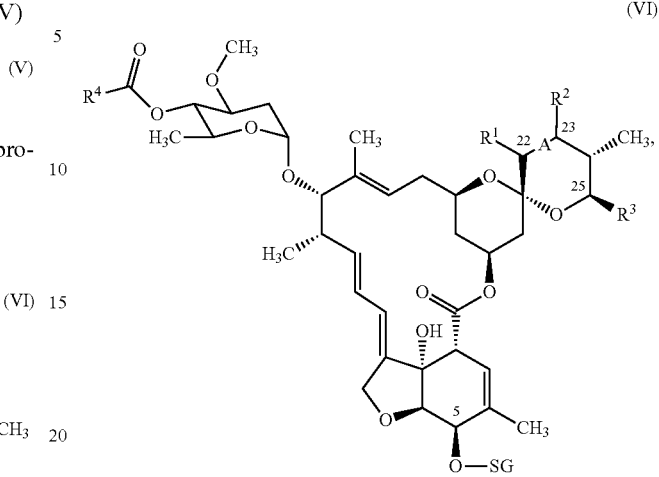

(VI)

in which the grouping $-C_{22}R^1-A-C_{23}R^2-$ represents $-HC=CH-$, $-H_2C-CH(OH)-$ or $-H_2C-CH_2-$, $R^3$ represents sec-butyl, isopropyl or cyclohexyl, and $R^4$ represents optionally substituted $C_{2-6}$-alkyl, $C_{2-6}$-alkenyl, $C_{2-6}$-alkynyl, $C_{1-6}$-alkoxy-$C_{1-4}$-alkyl, $C_{1-4}$-alkoxy-$C_{1-4}$-alkoxy-$C_{1-4}$-alkyl, cycloalkyl, cycloalkenyl, cycloalkyl-$C_{1-4}$-alkyl, aryl except for 4-chlorophenyl, aryl-$C_{1-4}$-alkyl, hetaryl, hetaryl-$C_{1-4}$-alkyl, heterocyclyl or heterocyclyl-$C_{1-4}$-alkyl, or represents a radical selected from the radicals ($G^7$) to ($G^{14}$)

(G⁷)

(G⁸)

(G⁹)

(G¹⁰)

(G¹¹)

(G¹²)

-continued

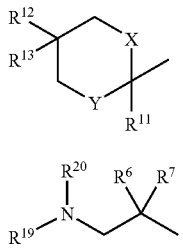

(G13)

(G14)

in which
B represents optionally $R^8$-, $R^9$- and $R^{10}$-substituted aryl, cycloalkyl, heterocyclyl, hetaryl or $NR^{19}R^{20}$,
D represents optionally $R^8$-, $R^9$- and $R^{10}$-substituted aryl, cycloalkyl, heterocyclyl, hetaryl or $NR^{19}R^{20}$,
$R^6$ represents hydrogen, halogen, fluorine, cyano, optionally substituted alkyl, alkenyl, alkynyl, cycloalkyl or heterocyclyl,
$R^7$ represents hydrogen, halogen, fluorine, cyano, optionally substituted alkyl, alkenyl, alkynyl or
$R^6$ and $R^7$ together with the atom to which they are attached represent a 3-, 4-, 5-, 6- or 7-membered ring which is optionally substituted and/or optionally interrupted by oxygen, sulphur, nitrogen, sulphinyl or sulphonyl, or
$R^6$ and $R^7$ together with the atom to which they are attached represent an optionally substituted exo-methylene bond,
$R^8$ represents hydrogen, optionally substituted $C_{1-4}$-alkyl, $C_{3-6}$-cycloalkyl, $C_{1-4}$-haloalkyl, $C_{1-4}$-alkoxy, $C_{1-4}$-alkoxy-$C_{1-4}$-alkoxy, $C_{1-4}$-haloalkoxy, $C_{1-4}$-alkylthio, $C_{1-4}$-haloalkylthio, $C_{1-4}$-alkylsulphinyl, $C_{1-4}$-haloalkylsulphinyl, $C_{1-4}$-alkylsulphonyl, $C_{1-4}$-haloalkylsulphonyl, hetaryl, halogen, nitro, cyano, amino, $C_{1-4}$-alkylamino, di-($C_{1-4}$-alkyl)-amino, or represents a radical selected from the group consisting of CO—OH, COO$^{(-)}$, COO—$C_{1-6}$-alkyl, NH—CHO, NH—CO—$C_{1-4}$-alkoxy, N($C_{1-4}$-alkyl)-CO—$C_{1-4}$-alkoxy, P(O)(OH)$_2$, P(O)O$^{(-)}_2$, CO—NH$_2$, CS—NH$_2$, C(=NH)—NH$_2$, C(=N—OH)—NH$_2$, CO—NH—$C_{1-4}$-alkyl, CO—N—($C_{1-4}$-alkyl)$_2$, CO—NH—$C_{1-4}$-alkoxy, CO—NH—CO—$C_{1-4}$-alkyl, CO—NH—CO—$C_{1-4}$-haloalkyl, CO—NH—CO—$C_{3-7}$-cycloalkyl, CO—NH—CO—$C_{1-4}$-alkoxy, CO—NH—CO-(aryl-$C_{1-2}$-alkyloxy), SO$_2$—OH, SO$_2$—O$^{(-)}$, SO$_2$—NH$_2$, SO$_2$—NH—$C_{1-4}$-alkyl, SO$_2$—N—($C_{1-4}$-alkyl)$_2$, CO—NH—SO$_2$—NH—$C_{1-4}$-alkyl, CO—NH—SO$_2$—N[di($C_{1-4}$-alkyl), and CO—O—$C_{1-6}$-alkyl,
$R^9$ represents hydrogen or optionally substituted $C_{1-4}$-alkyl, $C_{1-4}$-haloalkyl, $C_{1-4}$-alkoxy, $C_{1-4}$-haloalkoxy, $C_{1-4}$-alkylthio, $C_{1-4}$-alkylsulphinyl, $C_{1-4}$-alkylsulphonyl, halogen, nitro, cyano, formyl, $C_{1-4}$-alkylcarbonyl, amino, $C_{1-4}$-alkylamino, di-($C_{1-4}$-alkyl)-amino, optionally substituted aryl, optionally substituted hetaryl or optionally substituted heterocyclyl,
$R^{10}$ represents hydrogen or optionally substituted $C_{1-4}$-alkyl, $C_{2-4}$-alkenyl, $C_{2-4}$-alkynyl, $C_{1-4}$-haloalkyl, $C_{1-4}$-alkylcarbonyl, or $C_{1-4}$-alkoxycarbonyl,
$R^{11}$ represents hydrogen, cyano or optionally substituted $C_{1-6}$-alkyl,
$R^{12}$ and $R^{13}$ independently of one another represent hydrogen, hydroxyl, or optionally substituted $C_{1-4}$-alkyl, $C_{2-4}$-alkenyl, $C_{2-4}$-alkynyl, $C_{1-6}$-alkylcarbonyl, $C_{1-6}$-alkylamino, di-($C_{1-6}$-alkyl)-amino, $C_{1-6}$-alkylamino-$C_{1-4}$-alkyl, di-($C_{1-6}$-alkyl)-amino-$C_{1-4}$-alkyl, $C_{1-6}$-alkoxy-$C_{1-4}$-alkyl, amino-$C_{1-4}$-alkyl, $C_{3-6}$-cycloalkyl, aryl, aryl-$C_{1-4}$-alkyl, hetaryl-$C_{1-4}$-alkyl, heterocyclyl, heterocyclyl-$C_{1-4}$-alkyl or hetaryl,
or
$R^{12}$ and $R^{13}$ together with the atom to which they are attached represent an optionally substituted 3-, 4-, 5-, 6- or 7-membered ring which may optionally be interrupted by oxygen, sulphur, nitrogen, sulphinyl or sulphonyl,
or
$R^{12}$ and $R^{13}$ together with the atom to which they are attached represent

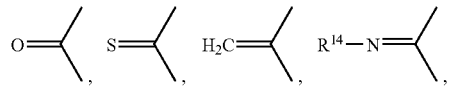

X represents oxygen, sulphur, sulphinyl, sulphonyl or N—$R^{14}$, where $R^{14}$ represents hydrogen or optionally substituted $C_{1-4}$-alkyl,
Y represents oxygen, sulphur, sulphinyl, sulphonyl or N—$R^{15}$, where $R^{15}$ represents hydrogen, optionally substituted $C_{1-4}$-alkyl,
$R^{16}$ represents methyl, chlorine, bromine or trifluoromethyl,
$R^{17}$ represents methyl, chlorine or bromine,
$R^{18}$ represents hydrogen or optionally substituted $C_{1-4}$-alkyl, aryl-$C_{1-4}$-alkyl or hetaryl-$C_{1-4}$-alkyl,
$R^{19}$ and $R^{20}$ independently of one another represent hydrogen or optionally substituted $C_{1-4}$-alkyl, $C_{1-4}$-haloalkyl, $C_{1-4}$-alkoxycarbonyl, $C_{1-4}$-alkylcarbonyl, $C_{1-6}$-alkoxy-$C_{1-4}$-alkyl, $C_{1-6}$-alkylamino-$C_{1-4}$-alkyl, di-($C_{1-6}$-alkyl)-amino-$C_{1-4}$-alkyl, $C_{1-4}$-alkoxycarbamoyl, $C_{2-6}$-alkenyl, $C_{2-6}$-alkynyl, aryl-$C_{1-4}$-alkyl, hetaryl-$C_{1-4}$-alkyl, or
$R^{19}$ and $R^{20}$ together with the nitrogen atom to which they are attached represent a cyclic amino group or represent a 3-, 4-, 5-, 6- or 7-membered ring which is optionally interrupted by oxygen, sulphur, nitrogen, sulphinyl or sulphonyl and/or which is optionally substituted by at least one radical as defined in $R^8$, $R^9$ and $R^{10}$ and
SG is a protective group radical.
12. The avermectin derivative according to claim 1, in which
the grouping —$C_{22}R^1$-A-$C_{23}R^2$— represents —HC═CH— or —H$_2$C—CH$_2$—,
$R^3$ represents sec-butyl or isopropyl,
$R^5$ represents hydrogen, and
$R^4$ represents a radical selected from the group consisting of ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, 2-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl and 2-ethylbutyl; cyclopropyl, 1-methylcyclobutyl, 1-cyanocyclopropyl, 1-fluorocyclopropyl, cyclopentyl, cyclopentenyl, cyclohexyl, methoxymethyl, methoxyethyl, ethoxymethyl, ethoxyethyl, methoxypropyl, ethoxypropyl, methoxybutyl, ethoxybutyl, 2-fluoroethyl, 3,3,3-trifluoroethyl, 2,2-dichlorocyclopropyl, aminomethyl, aminoethyl, aminopropyl, aminobutyl, N-methylaminomethyl, N-methylaminoethyl, N-methylaminopropyl, N-methylaminobutyl, N,N-dimethylaminomethyl, N,N-dimethylaminoethyl, N,N-dimethylaminopropyl, N,N-dimethylaminobutyl, N-ethyl-N-propylaminomethyl, N-ethyl, N-propylaminoethyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, thiazolylmethyl, 1,2,3-triazolyl-1-ylmethyl, 1,2,3-triazoly-1-yl-2-ethyl, N-pyrazolylmethyl, N-pyrrolylmethyl, N-methylpyrrol-2-ylmethyl, furylmethyl, thien-3-ylmethyl, pyrid-2-ylmethyl, pyrid-3-ylmethyl, 1,2,3,4-tetrazol-1-ylmethyl which may optionally be substituted by at least one substituent selected from the group consisting of fluorine, chlorine, bromine, iodine, methyl, ethyl, isopropyl, cyclopropyl, cyclopropoxy, cyclopropylmethoxy, trifluoromethyl, amino, hydroxyl, nitro, cyano, SO$_2$OH, COOH, formyl, methoxy, ethoxy, isopropoxy, methylenedioxy, ethylenedioxy, difluoromethoxy, tetrafluoroethoxy, trifluoromethoxy, methylthio, methylsulphonyl, trifluoromethylthio, trifluoromethylsulphoxyl, methylamino, N,N-dimethylamino, methylcarbonyl, cyclopropyl-carbonyl, methoxycarbonyl, and methoxyethoxymethyl, with the proviso that R$^4$ does not represent 4-chlorophenyl, or R$^4$ represents a radical selected from the radicals below

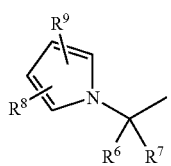
(G$^7$-1)

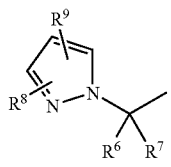
(G$^7$-2)

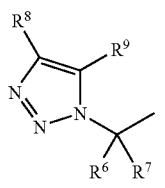
(G$^7$-3)

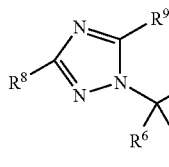
(G$^7$-4)

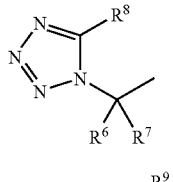
(G$^7$-5)

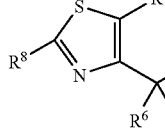
(G$^7$-6)

-continued

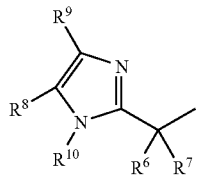
(G$^7$-8)

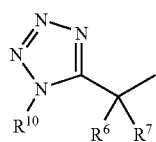
(G$^7$-9)

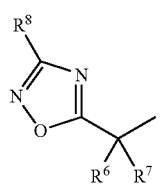
(G$^7$-10)

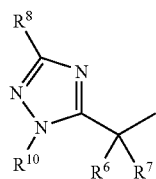
(G$^7$-12)

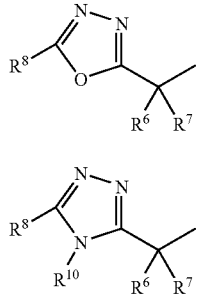
(G$^7$-13)

(G$^7$-15)

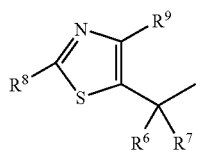
(G$^7$-17)

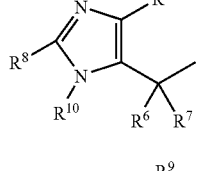
(G$^7$-21)

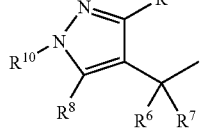
(G$^7$-22)

-continued (G⁷-24) 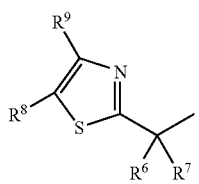

(G⁷-25) 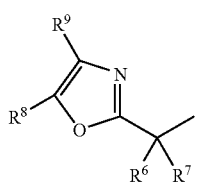

(G⁷-26) 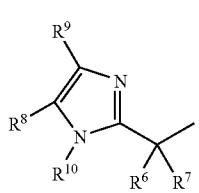

(G⁷-28) 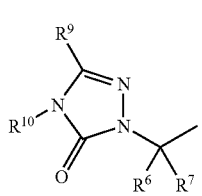

(G⁷-29) 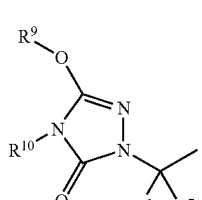

(G⁷-30) 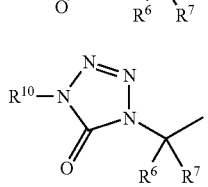

(G⁷-33) 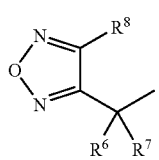

(G⁷-34) 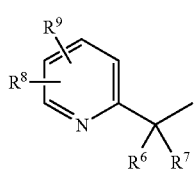

(G⁷-35) 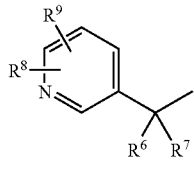

-continued (G⁷-43) 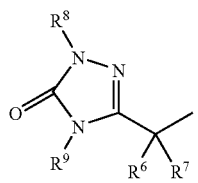

(G⁷-44) 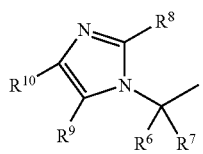

or represents a radical (G¹²-1) or (G¹⁴-1)

(G¹²-1) 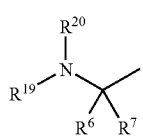

(G¹⁴-1)

$$\underset{R^{19}}{\overset{R^{20}}{N}}\underset{R^{6}\ R^{7}}{\overset{}{\diagdown}}$$

in which
R⁶ and R⁷ together with the carbon to which they are attached are selected from the groupings (B-1), (B-2), (B-3), (B-9) and (B-10)

B-1 

B-2 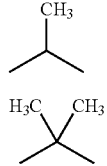

B-3 

B-9 

B-10

$$\underset{}{\overset{CH_2}{\diagdown}}$$ ,

R⁸ represents hydrogen, methyl, trifluoromethyl, difluoromethyl, methoxy, methoxyethoxy, trifluoromethoxy, difluoromethoxy, methylthio, methylsulphinyl, methylsulphonyl, trifluoromethylthio, trifluoromethylsulphinyl, trifluoromethylsulphonyl, cyclopropyl, pyridyl, thienyl, fluorine, chlorine, bromine, iodine, nitro, cyan, amino, methylamino, dimethylamino, diethylamino or is selected from the group consisting of CO—OH, COO⁽⁻⁾, COO—$C_{1-6}$-alkyl, CO—$NH_2$, CS—$NH_2$, C(=NH)—$NH_2$, C(=N—OH)—$NH_2$, CO—$NHCH_3$, CO—$N(CH_3)_2$, CO—$NHOCH_3$, CO—NH—$COCH_3$, CO—NH—COOCH₃, CO—NH—CO—O-benzyl, SO₂—OH, SO₂—O⁻⁾, SO₂—NH₂, SO₂—NHCH₃, SO₂—N(CH₃)₂, CO—NH—SO₂—NHCH₃, or CO—NH—SO₂—N(CH₃)₂;

R⁹ represents hydrogen, methyl, trifluoromethyl, methoxy, trifluoromethoxy, methylthio, methylsulphinyl, methylsulphonyl, fluorine, chlorine, bromine, iodine, nitro, cyano, formyl, acetyl, amino, methylamino, dimethylamino, diethylamino, phenyl, 2-, 3-or 4-chlorophenyl, 3-chloropyrid-2-yl, pyrid-4-yl, or 2-bromopyrid-2-yl; and R¹⁰ represents hydrogen, methyl, ethyl, n-propyl, isopropyl, butyl, trifluoromethyl, difluoromethyl, acetyl, methoxycarbonyl, ethoxycarbonyl or tert-butoxycarbonyl, or R⁴ represents a radical (G⁹-1)

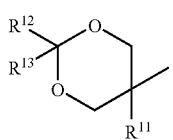

(G⁹-1)

in which R¹¹ represents methyl, and

R¹² and R¹³ independently of one another represent hydrogen, methyl, ethyl, n-propyl, n-butyl, isopropyl, 1-propenyl, methoxyethyl, ethoxyethyl, methylaminomethyl, N,N-dimethylaminomethyl, hydroxymethyl, benzyloxymethyl, acetyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, or thiazolylmethyl which may optionally be substituted by at least one substituent selected from the group consisting of fluorine, chlorine, bromine, iodine, methyl, ethyl, isopropyl, cyclopropyl, cyclopropoxy, cyclopropylmethoxy, trifluoromethyl, amino, hydroxy, nitro, cyano, SO₂OH, COOH, formyl, methoxy, ethoxy, isopropoxy, methylenedioxy, ethylenedioxy, difluoromethoxy, tetrafluoroethoxy, trifluoromethoxy, methylthio, methylsulphonyl, trifluoromethylthio, trifluoromethylsulphoxyl, methylamino, N,N-dimethylamino, methylcarbonyl, cyclopropylcarbonyl, and methoxycarbonyl; and R¹⁹ and R²⁰ independently of one another represent hydrogen or optionally substituted C₁₋₄-alkyl, C₁₋₄-alkoxycarbonyl, or C₁₋₄-alkylcarbonyl, or R¹⁹ and R²⁰ together with the nitrogen atom to which they are attached represent optionally substituted pyrrolidine, morpholine, 2,6-dimethylmorpholine, 3-oxomorpholine, optionally substituted piperidine, tert-butyloxycarbonylamino-substituted piperidine or aminosubstituted piperidine, optionally substituted piperazine, tert-butyloxycarbonyl-substituted piperazine or methyl-substituted piperazine.

13. The avermectin derivative according to claim 1, in which the grouping —C₂₂R¹-A-C₂₃R²— represents —HC=CH— or —H₂C—CH₂—, R³ represents sec-butyl, R⁵ represents hydrogen and R⁴ represents a radical selected from the group consisting of ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, 2-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl and 1-ethylbutyl and 2-ethylbutyl; cyclopropyl, 1-methylcyclobutyl, cyanocyclopropyl, 1-fluorocyclopropyl, aminomethyl, aminoethyl, N-methylaminomethyl, N-methylaminoethyl, N,N-dimethylaminomethyl, N,N-dimethylaminoethyl, cyclohexyl, methoxymethyl, methoxyethyl, 2-fluoroethyl, 3,3,3-trifluoroethyl, 2,2-dichlorocyclopropyl, phenethyl, pyridylmethyl, pyridylethyl, pyrazinylmethyl, pyrimidylmethyl, 1,2,3-triazol-1-ylmethyl, N-pyrazolylmethyl, N-pyrrolylmethyl, N-methylpyrrol-2-yl methyl, and 1,2,3,4-tetrazol-1-ylmethyl, which may optionally be substituted by at least one substituent selected from the group consisting of fluorine, chlorine, bromine, iodine, methyl, trifluoromethyl, amino, hydroxyl, SO₂OH, COOH, formyl, methoxy, trifluoromethoxy, difluoromethoxy, methylamino, N,N-dimethylamino, methylcarbonyl, cyclopropylcarbonyl, and methoxycarbonyl, or R⁴ represents a radical selected from the radicals below

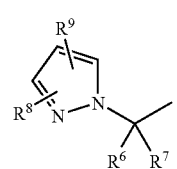

(G⁷-2)

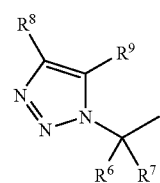

(G⁷-3)

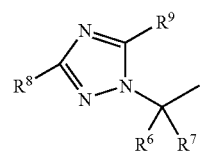

(G⁷-4)

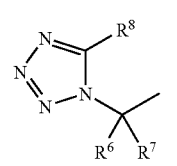

(G⁷-5)

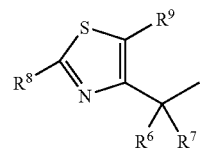

(G⁷-6)

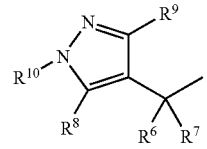

(G⁷-22)

-continued

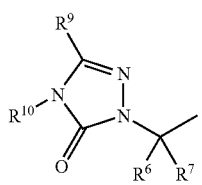
(G⁷-28)

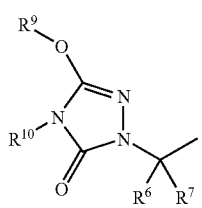
(G⁷-29)

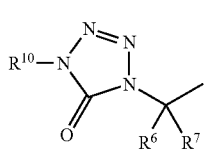
(G⁷-30)

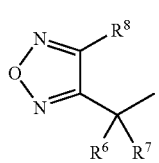
(G⁷-33)

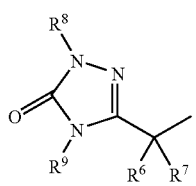
(G⁷-43)

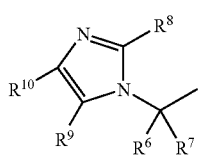
(G⁷-44)

or represents a radical (G¹²-1) or (G¹⁴-1)

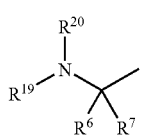
(G¹²-1)

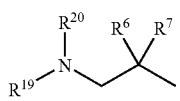
(G¹⁴-1)

in which
R⁶ and R⁷ together with the carbon atom to which they are attached are selected from the groupings (B-1), (B-2), (B-3), and (B-9)

 B-1

 B-2

 B-3

 B-9

R⁸ represents hydrogen, methyl, trifluoromethyl, methoxy, trifluoromethoxy, fluorine, chlorine, bromine, iodine, methylamino or dimethylamino or is selected from the group consisting of CO—NH₂, CO—NHCH₃, CO—N(CH₃)₂, CO—NHOCH₃, CO—NH—COCH₃, CO—NH—COOCH₃, CO—NH—CO—O-benzyl, SO₂—NH₂, SO₂—NHCH₃, SO₂—N(CH₃)₂, CO—NH—SO₂—NHCH₃, and CO—NH—SO₂—N(CH₃)₂;

R⁹ represents hydrogen, methyl, trifluoromethyl, methoxy, trifluoromethoxy, fluorine, chlorine, bromine, iodine, acetyl, methylamino, dimethylamino, diethylamino, phenyl, 4-chlorophenyl, or pyrid-4-yl, R¹⁰ represents methyl, acetyl, methoxycarbonyl, or tert-butoxycarbonyl, or represents a radical from groups (G³) and (G⁹) below

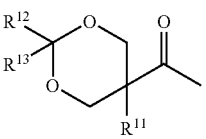
(G³-1)

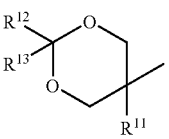
(G⁹-1)

in which
R¹¹ represents methyl, and
R¹² and R¹³ independently of one another represent methyl, methoxyethyl, methylaminomethyl, or
R¹² represents hydrogen, and R¹³ represents methyl, ethyl, n-propyl, 1-propenyl, methoxyethyl, ethoxyethyl, methylaminomethyl, N,N-dimethylaminomethyl, phenyl, benzyl, phenethyl, pyridyl, pyrimidyl, pyrazinyl, pyrazolyl, thiazolyl, thienyl, furyl, pyridylmethyl, pyridylethyl, pyrazinylmethyl, pyrimidylmethyl, or thiazolylmethyl which may optionally be substituted by at least one substituent selected from the group consisting of fluorine, chlorine, bromine, iodine, methyl, ethyl, isopropyl, cyclopropyl, cyclopropoxy, cyclopropylmethoxy, trifluoromethyl, amino, hydroxyl, nitro, cyano, SO₂OH, COOH, formyl, methoxy, isopropoxy, methylenedioxy, ethylenedioxy, difluoromethoxy, tetrafluorethoxy, trifluoromethoxy, difluoromethoxy, methylthio, methylsulphonyl, trifluoromethylthio, trifluoromethylsulphoxyl, methylamino, N,N-dimethylamino, methylcarbonyl, cyclopropylcarbonyl, and methoxycarbonyl.

$R^{19}$ and $R^{20}$ independently of one another represent hydrogen, methyl, ethyl, tert-butyloxycarbonyl, acetyl, or $R^{19}$ and $R^{20}$ together with the nitrogen atom to which they are attached represent pyrrolidine, morpholine, 2,6-dimethylmorpholine, 3-oxomorpholine, piperidine, tert-butyloxycarbonylamino-substituted piperidine or 4-amino-substituted piperidine, piperazine, tert-butyloxycarbonyl-substituted piperazine or 4-methyl-substituted piperazine.

14. A composition according to claim 3, further comprising extender, liquid solvent, solid carrier, surfactant, emulsifier, dispersant, tackifier, and/or colorant.

15. A composition according to claim 3, wherein the avermectin derivative of claim 1 is mixed with insecticide, attractant, sterilizing agent, bactericide, acaricide, nematicide, fungicide, growth-regulating substance, herbicide, safener, fertilizer, and/or semiochemical.

16. A method for treating a seed comprising applying an avermectin derivative of formula (I) according to claim 1 to the seed.

17. A method according to claim 5, wherein the animal pest is *Lucilia cuprina, Musca domestica, Phaedon cochleariae, Bernisia tabaci, Tetranychus urticae, Spodoptera frugiperda*, or *Ctenocephalides felis*.

* * * * *